United States Patent
Wieduwild et al.

(10) Patent No.: US 11,523,990 B2
(45) Date of Patent: *Dec. 13, 2022

(54) NON-COVALENT, SELF-ORGANZING HYDROGEL MATRIX FOR BIOTECHNOLOGICAL APPLICATIONS

(71) Applicant: DENOVOMATRIX GMBH, Dresden (DE)

(72) Inventors: Robert Wieduwild, Dresden (DE); Yixin Zhang, Dresden (DE); Carsten Werner, Dresden (DE); Mikhail Tsurkan, Dresden (DE); Uwe Freudenberg, Dresden (DE)

(73) Assignee: DENOVOMATRIX GMBH, Dresden (DE)

(*) Notice: Subject to any disclaimer, the term of this patent is extended or adjusted under 35 U.S.C. 154(b) by 0 days.

This patent is subject to a terminal disclaimer.

(21) Appl. No.: 16/559,710

(22) Filed: Sep. 4, 2019

(65) Prior Publication Data
US 2020/0179280 A1   Jun. 11, 2020

Related U.S. Application Data

(63) Continuation-in-part of application No. 14/427,870, filed as application No. PCT/DE2013/100327 on Sep. 13, 2013, now abandoned.

(30) Foreign Application Priority Data

Sep. 13, 2012 (DE) .......................... 102012108560.9

(51) Int. Cl.
*A61K 9/14* (2006.01)
*A61K 9/06* (2006.01)
(Continued)

(52) U.S. Cl.
CPC ................. *A61K 9/06* (2013.01); *A61K 45/06* (2013.01); *A61K 47/26* (2013.01); *A61K 47/34* (2013.01); *A61K 47/36* (2013.01); *A61K 47/40* (2013.01)

(58) Field of Classification Search
CPC .......... A61K 9/06; A61K 45/06; A61K 47/26; A61K 47/34; A61K 47/36; A61K 47/40
See application file for complete search history.

(56) References Cited

U.S. PATENT DOCUMENTS

| 5,534,619 A | 7/1996 | Wakefield |
| 6,958,212 B1 | 10/2005 | Hubbell et al. |

(Continued)

FOREIGN PATENT DOCUMENTS

| WO | 94/04176 | 3/1994 |
| WO | 2008/124165 | 10/2008 |

OTHER PUBLICATIONS

Yamaguchi et al., "Rheological Characterization of Polysaccharide-Poly(ethylene glycol) Star Copolymer Hydrogels" Biomacromolecules, vol. 6, No. 4, May 28, 2005 (May 28, 2005), pp. 1931-1940.

(Continued)

*Primary Examiner* — David Browe
(74) *Attorney, Agent, or Firm* — JMB Davis Ben-David

(57) ABSTRACT

The invention relates to a hydrogel matrix comprising a mixture of a covalent peptide-polymer conjugate and an oligosaccharide;
  wherein the oligosaccharide is a highly negatively charged sulfated oligosaccharide selected from the group consisting of heparin, dextran sulfate, α-cyclodextrin sulfate, β-cyclodextrin sulfate and γ-cyclodextrin sulfate;
  wherein said polymer comprised in said peptide-polymer conjugate is a linear or multi-arm polyethylene glycol;
(Continued)

wherein said peptide comprised in said peptide-polymer conjugate is a peptide, which consists of an amino acid sequence selected from the group consisting of SEQ ID NO.4, SEQ ID NO.5, SEQ ID NO. 18 and SEQ ID NO. 19; and wherein said hydrogel matrix is configured in the form of an oligosaccharide/peptide/polymer system, in which said peptide is chemically conjugated to the polymer such that the hydrogel is obtained by mixing the peptide-polymer conjugate and the oligosaccharide.

10 Claims, 33 Drawing Sheets

Specification includes a Sequence Listing.

(51) Int. Cl.

| | | |
|---|---|---|
| A61K 45/06 | (2006.01) | |
| A61K 47/34 | (2017.01) | |
| A61K 47/26 | (2006.01) | |
| A61K 47/36 | (2006.01) | |
| A61K 47/40 | (2006.01) | |

(56) References Cited

U.S. PATENT DOCUMENTS

2010/0317110 A1  12/2010  Kiick et al.
2011/0033543 A1  2/2011  Kiick et al.

OTHER PUBLICATIONS

Yamaguchi et al., "Polysaccharide-poly(ethylene glycol) star copolymer as a scaffold for the production of bioactive hydrogels", Biomacromolecules, vol. 6, No. 4, Jul. 2005 (Jul. 2005), pp. 1921-1930.
Kyung Jae Jeong et al., "Interplay between Covalent and Physical Interactions within Environment Sensitive Hydrogels" Biomacromolecules, vol. 10, No. 5, Mar. 23, 2009 (Mar. 23, 2009), pp. 1090-1099.
Mikhail V. Tsurkan et al., "Enzymatically degradable heparin-polyethylene glycol gels with control led mechanical properties", Chemical Communications, vol. 46, No. 7, Dec. 16, 2009 (Dec. 16, 2009), pp. 1141-1143.
Mikhail V. Tsurkan et al., "Modular Star PEG-Heparin Gels with Bifunctional Peptide Linkers" Macromolecular Rapid Communications, vol. 31, No. 17, Aug. 16, 2010 (Aug. 16, 2010), pp. 1529-1533.
Seal B L et al, "Physical matrices stabilized by enzymatically sensitive covalent crosslinks", Acta Biomaterialia, vol. 2, No. 3, May 1, 2006 (May 1, 2006), pp. 241-251.
Alison B. Pratt et al: "Synthetic extracellular matrices for in situ tissue engineering", Biotechnology and Bioengineering, vol. 86, No. 1, Feb. 12, 2004 (Feb. 12, 2004), pp. 27-36.
Brandon L. Seal et al: "Physical Polymer Matrices Based on Affinity Interactions between Peptides and Polysaccharides", vol. 4, No. 6, Nov. 1, 2003 (Nov. 1, 2003), pp. 1572-1582.
Freudenberg U et al: "A star-PEG-heparin hydrogel platform to aid cell replacement therapies for neurodegenerative diseases" Biomaterials, vol. 30, No. 28, Oct. 1, 2009 (Oct. 1, 2009), pp. 5049-5060.
Nie T et al: "Production of heparin-containing hydrogels for modulating cell responses" Acta Biomaterialia, vol. 5, No. 3, Mar. 2009 (Mar. 2009), 865-875.
Benoit et al, "The effect of heparin-functional i zed PEG hydrogels on three-dimensional human mesenchymal stem cell osteogenic differentiation", Biomaterials, vol. 28, No. 1, Jan. 1, 2007 (Jan. 1, 2007), pp. 66-77.
Brandon L. Seal et al, "Viscoelastic Behavior of Environmentally Sensitive Biomimetic Polymer Matrices", Macromolecules, vol. 39, No. 6, Feb. 23, 2006 (Feb. 23, 2006), pp. 2268-2274.
Kopecek et al. Acta Biomater. 2009; 5(3): 805-816.
Seal et al. Biomacromolecules. 2003; 4: 1572-1582.
Zhang L. et al.: "Manipulation of hydrogel assembly and growth factor delivery via the use of peptide-polysaccharide interactions", J Control Release 2006, 114(2); p. 130-142.
Spinelli, F. et al.: "The role of heparin self-association in the gelation of heparin-functionalized polymers", Biomaterials 2008, vol. 29, p. 1299-1306.
Kiick, K: "Peptide- and protein-mediated assembly of heparinized hydrogels", Soft Matter 2008, vol. 4, p. 29-37.
Zieris, A. et al.: "Analytical approaches to uptake and release of hydrogel-associated FGF-2", J Mater Sci, Mater Med 2010, vol. 21, p. 915-923.
Zieris, A. et al.: "FGF-2 and VEGF functionalization of starPEGeheparin hydrogels to modulate biomolecular and physical cues of angiogenesis", Biomaterials 2010, vol. 31, p. 7985-7994.
Freudenberg, U. et al.: "Using Mean Field Theory to Guide Biofunctional Materials Design", Adv. Fund. Mater. 2012, vol. 22, p. 1391-1398.
Chwalek, K. et al.: "Two-tier hydrogel degradation to boost endothelial cell morphogenesis", Biomaterials 2011, vol. 32, p. 9649-9657.
Shen, W. et al.: Tuning the erosion rate of artificial protein hydrogels through control of network topology', Nature Materials, 2006, vol. 5, p. 153-158.
Soong Ho Urn et al.: "Enzyme-catalysed assembly, of DNA hydrogel", Nature Materials, 2006, vol. 5, p. 797-801.
Tyler-Cross, R. et al.: "Heparin binding domain peptides of antithrombin 111: Analysis by isothermal titration calorimetry and circular dichroism spectroscopy", Protein Science 1994, vol. 3: p. 620-627.
Pace, C.N. et al.: "A Helix Propensity Scale Based on Experimental Studies of Peptides and Proteins", Biophysical Journal 1998, vol. 75, p. 422-427.
Fromm, J. R. et al.: "Pattern and Spacing of Basic Amino Acids in Heparin Binding Sites", Archives of Biochemistry and Biophysics 1997, vol. 343, No. 1, p. 92-100.
Anderson, S. et al.: "The performance of human mesenchymal stem cells encapsulated in cell-degradable polymer-peptide hydrogels" Biomaterials 2011, vol. 32, p. 3564-3574.

Figure 1
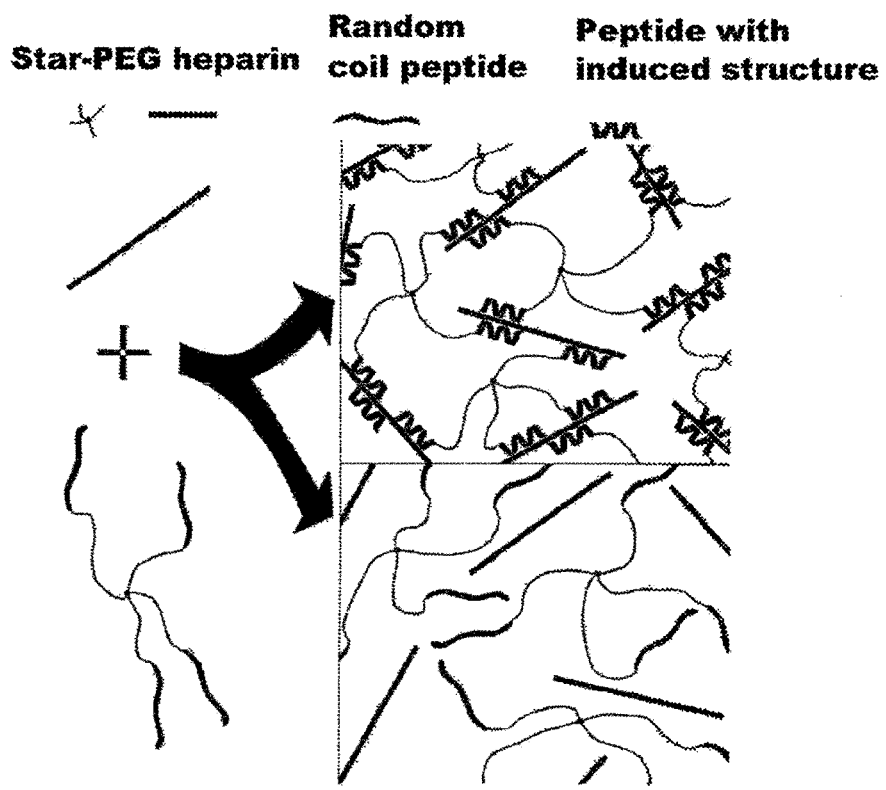
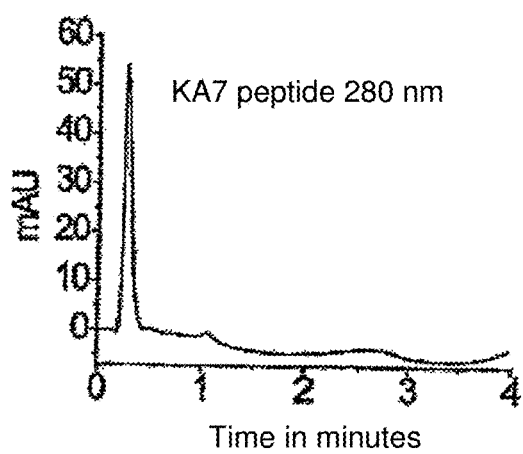
Figure 2A
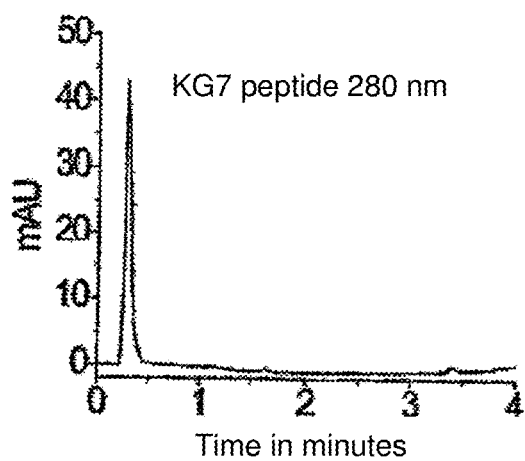
Figure 2B

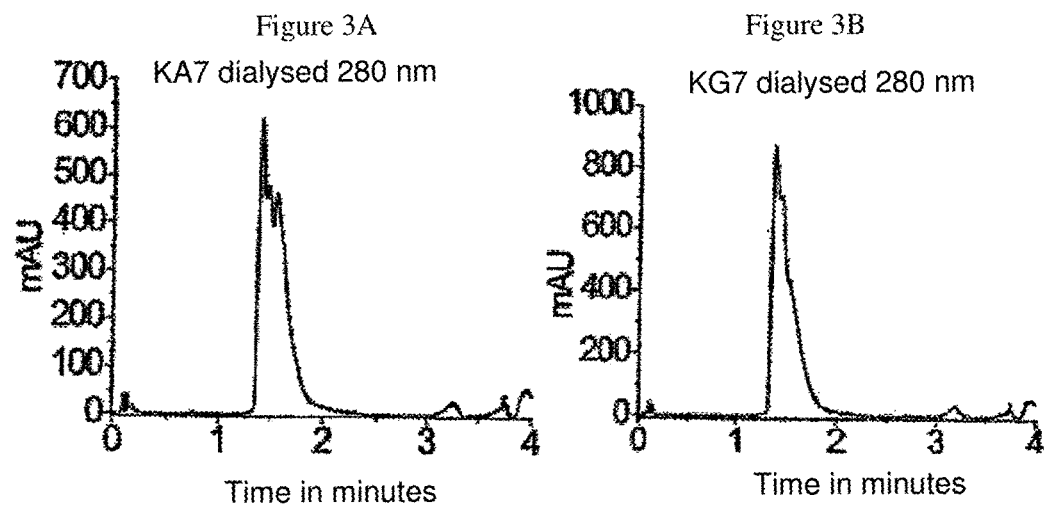
Figure 4A
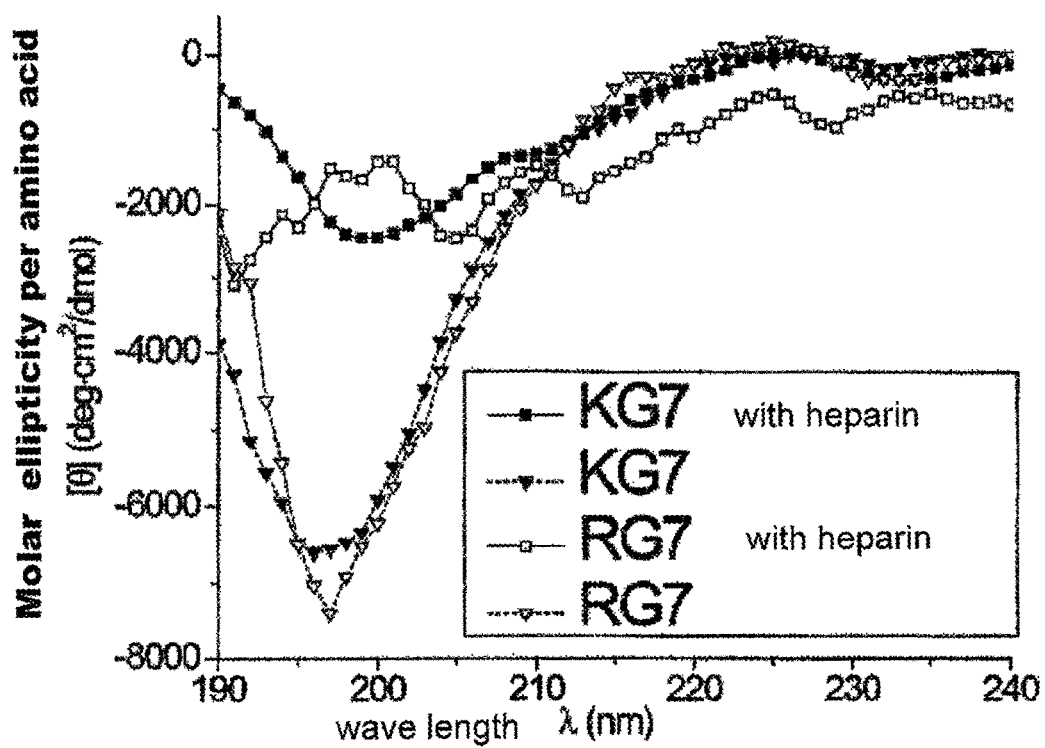

Figures 24A-24F
Fig. 24A
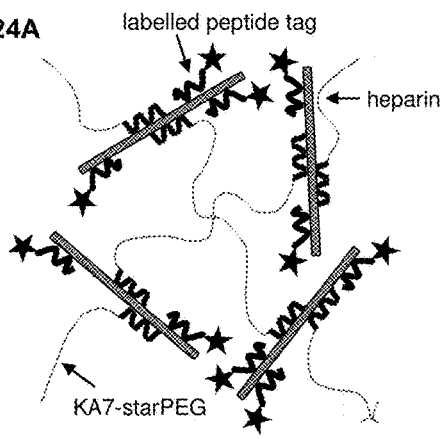
Fig. 24B
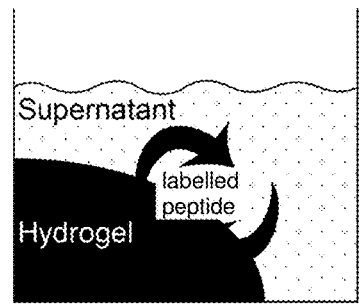
Fig. 24C
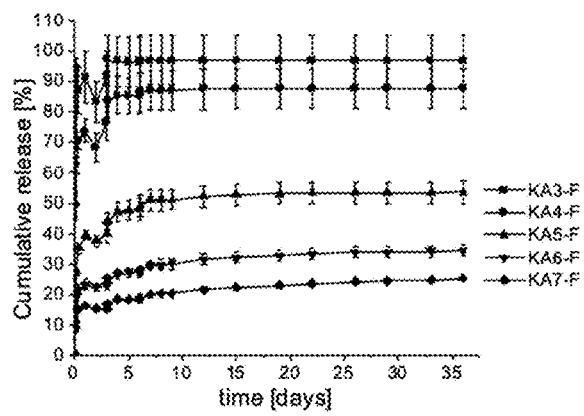
Fig. 24D
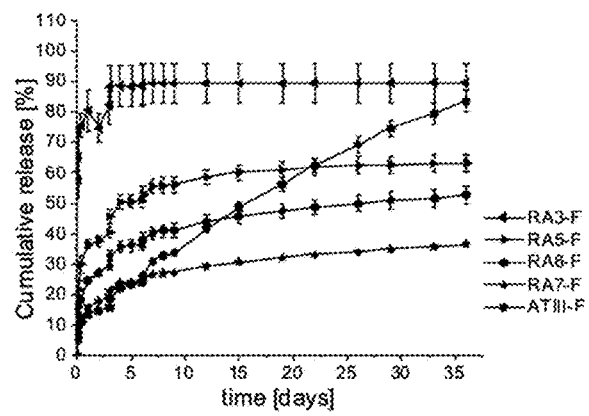
Fig. 24E
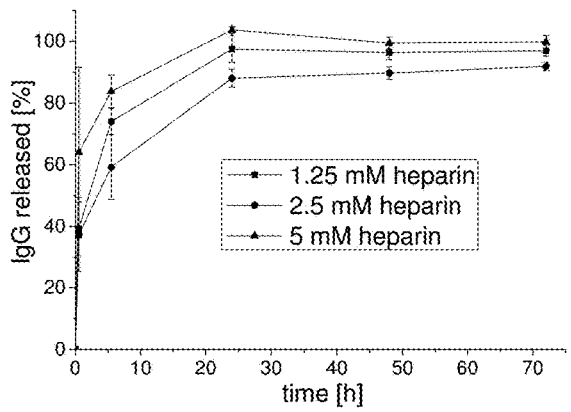
Fig. 24F
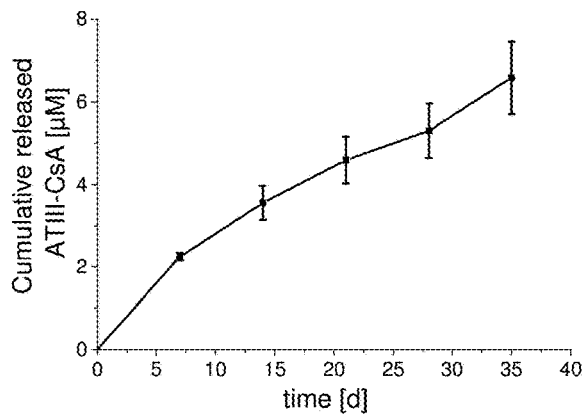

Figures 25A-25D
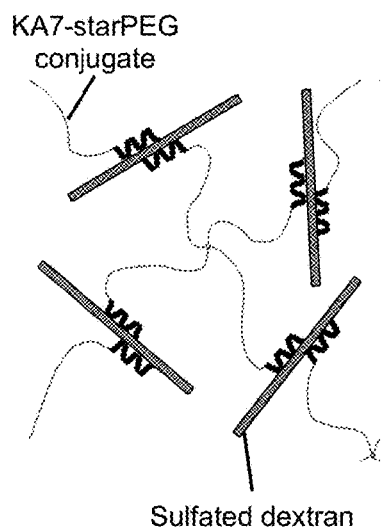
Fig. 25A
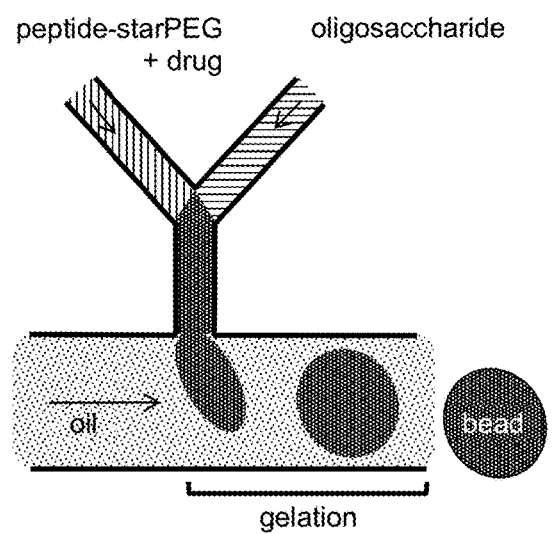
Fig. 25B
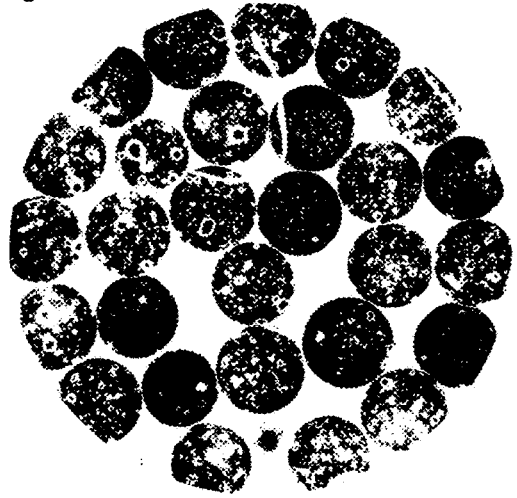
Fig. 25C
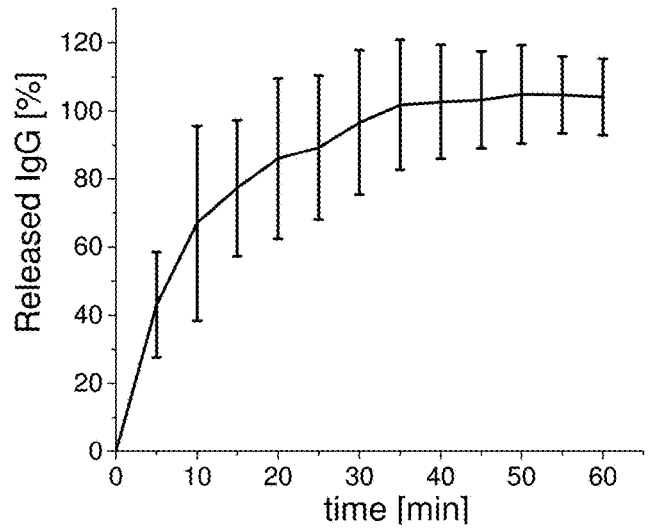
Fig. 25D

NON-COVALENT, SELF-ORGANZING HYDROGEL MATRIX FOR BIOTECHNOLOGICAL APPLICATIONS

CROSS-REFERENCE TO RELATED APPLICATIONS

This is a Continuation-in-Part of U.S. patent application Ser. No. 14/427,870, filed Mar. 12, 2015, which is the national stage of International Patent Application No. PCT/DE2013/100327, filed Sep. 13, 2013. The foregoing patent application is incorporated by reference herein in its entirety.

FIELD

The invention refers to a non-covalent self-organizing hydrogel matrix for biological applications. Furthermore, the invention refers to hydrogel matrix spheres formed from the hydrogel matrix as well as a composite of the hydrogel matrix or the hydrogel matrix spheres with cells imbedded therein. Other aspects of the invention refer to a capsule for the targeted release of therapeutic reagents, a composition from the hydrogel matrix, chemicals and therapeutic reagents as well as a hybrid system from a non-spherical shaped hydrogel matrix and from hydrogel matrix spheres.

BACKGROUND

The design and the synthesis of self-organizing macromolecule systems for application in the area of "life science" and other areas is of great interest for chemistry, material sciences and biomedicine. Various hydrogels have awakened great expectations in their applicability in the biomedical area, such as for example in the area of active substance transport and tissue culture. A series of polymer matrices that are derived from living sources, such as for example tissue extracts and collagen hydrogels have shown to be superior relative to their high biocompatibility in the cell culture as compared to the known synthetic polymers. But biomaterials derived from living sources have no definitive chemical composition, which is inhibiting their broad application in biomedicine.

On the other hand, a system of polymeric matrices having a long shelf life can lead to a great variety of "made-to-measure" structures that are suitable for a variety of applications. In this manner, many properties of the system can be influenced. An example at this point are different physical and biochemical properties for the cultivation of different cell types or different gelation times and degradation speeds for an implantation at various diseased locations. Finally, an ideal synthetic hydrogel system should not only be capable to imitate the biological function of various extracellular matrices (ECM) but also should offer the possibility to control these functions and to optimize them. The design of such adjustable materials for biomedical applications represents a big challenge. In particular this applies to biological investigations about the composition and the functions of the various extracellular matrices (ECM) for polymer- and material scientific reconstruction respectively for construction of such systems as well as chemical investigations about the control of processes.

Synthetic polymers such as polyethyleneglycol (PEG), polyvinylalcohol, poly(N-isopropylacrylamide), poly(lacticacid-co-glycolic acid) (PLGA) and copolymers of these and other polymers provide many useful systems for use in the biomedical area. On the one hand, polymers were developed as chemical structures having minimal interaction with biological systems. For example, the immune system oftentimes does not detect them as antigens, whereby complications of immunogenicity can be avoided. On the other hand, this advantage on the lack of function leads also to a lack of similarity of these polymers with important functions of the living system, primarily relative to the dynamic and the signaling in the extracellular matrix (ECM).

The conjugation of bio-macromolecules and synthetic polymers represents an interesting path in order to design the afore-stated hydrogel systems. The bio-macromolecules of choice can be either of synthetic origin, such as for example, peptides from the solid phase peptide synthesis and DNA from the solid phase-oligonucleotide-synthesis, or of biological origin with well-defined chemical composition. It is very important that the bio-macromolecules exhibit no toxic properties and a low immunogenicity. Covalent as well as non-covalent methods can be used for crosslinking, whereby the non-covalent methods are of special research interest due to the possibility for the production of various gels. In addition, non-covalent, self-organizing systems can realize embedding cells into a matrix-system, without relying on chemical reactions.

Incorporation of polysaccharide molecules in biohybrid material occurs more and more in order to achieve synthetic or semi synthetic materials. In particular, hyaluronic acid and heparin were used in a series of design concepts due to their biological activities and their biological availability. Heparin, a oligosaccharide with the highest anionic charge density, which occurs in a biopolymer is utilized due to its affinity for a multitude of important signal molecules. While heparin is a complex polymer, which can be extracted from a biological source and respective samples differ from each other regarding mass distribution, composition of sugar monomers and the sulfating degree, dextran sulfate and cyclodextrin sulfate are simpler oligosaccharides. In addition, some of these cyclodextrin sulfate compositions are obtained as pure chemical compounds.

The development of biocompatible hydrogel represents an interesting beginning for research in the area of material sciences and also in the area of biomedicine. Non-covalent, self-organizing hydrogels or oligosaccharide containing hydrogels were developed within the last 10 years. In Kiicks et al. (N. Yamaguchi, B.-S. Chae, L. Zhang, K. L. Kiick, E. M/Furst, *Macromolecules* 2005, 6, 1931-1940; N. Yamaguchi, K. L. Kiick, *Journal of Controlled Release* 2006, 114-130-142; K. L. Kiick, *Soft Matter* 2008, 4 29-37; F. J. Spinelli, K. L Kiick, E. M. Furst, *Biomaterials* 2008, 29, 1299-1306), the use of low molecular Heparin-star-PEG-conjugate, that is, heparin coupled to four-armed StarPEG and the use of peptide-starPEG-conjugate, that is a natural derivatives of peptides coupled to four-armed starPEG, is described. After mixing of these two compounds, namely heparin-starPEG and peptide-starPEG, a hydrogel is formed in non-covalent manner. The capacity of heparin with low molecular weight (LMWH) to bind multiple partners was exploited for the attachment or release of growth factors or other desired heparin-binding peptides, respectively proteins, at the non-covalent organized matrices. Thus, also the arrangement of these hydrogels with the dimer heparin-binding growth factors VEGF (vascular endothelial growth factor) were utilized. An interesting result of the hydrogel networks that were mediated through a growth factor, is the ability for a respective receptor mediated gel-erosion. VEGF-networks, in presence of the VEGF receptors, which control the proliferation and migration of vascular endothelial cell, can selectively compete and dissociate.

In the development and synthesis of hydrogels, increasingly bio-orthogonal reactions and photo-induced thiol-ene reactions are utilized. The so-called click chemistry enables very selective and orthogonal reactions, which react with high efficiency under mild conditions. Anseth et al. (S. B. Anderson, .C.-C. Lin, D. V. Kuntzler, K. S. Anseth, *Biomaterials* 2011, 32, 3564-3574) have introduced a reliably functioning synthesis strategy, in which macromolecular precursors react by means of a copper-click-chemistry, which permits the direct encapsulation of cells within click-hydrogels. The mild chemical reaction between thiol and vinyl sulfone was also intensively utilized for producing various hydrogels. Recently, this has led to a synergy of these chemical and biochemical reactions for the design and for the synthesis of a series of multi functionalized hydrogel systems.

In the inventors own work, a modular system of biohybrid hydrogels on the basis of covalent crosslinked heparin and starPEG has been developed. (A. Zieries, S. Prokoph, P. Wenzel, M. Grimmer, K. Leventhal, W. Panyanuwat, U. Freudenberg, C. Werner, *Journal of Materials Science: Materials in Medicine* 2010, 21, 915-923; A. Zieris, S. Prokoph, K. R. Leventhal, P. B. Welzel, M. Grimmer, U. Freudenberg, C. Werner, *Biomaterials* 2010, 31, 7985-7994; U. Freudenberg, J.-U. Sommer, K. R. Leventhal, P. B. Welzel, A. Zieris, K. Chwalek, K. Schneider, S. Prokoph, M. Prewitz, R. Dockhorn, C. Werner, *Advanced Functional Materials* 2012, 22, 1391-1398; U. Freudenberg, A. Hermann, P. B. Welzel, K. Stirl, S. C. Schwartz, M. Grimmer, A. Zieris, W. Panayanuwat, S. Zschoche, D. Meinhold, *Biomaterials* 2009, 30, 5449-5060; M. V. Tzurkan, K. R. Leventhal, U. Freudenberg, C. Werner, *Chemical Communications* 2010, 46, 1141; K. Chwalek, K. R. Leventhal, M. V. Tzurkan, A Ziereis, U. Freudenberg, C. Werner, *Biomaterials* 2011, 32, 9649-9657; M. V. Tzurkan, K. Chwalek, K. R. Leventhal, U. Freudenberg, C. Werner, *Macromol Rapid Commun* 2010, 31, 1529-1533), in which network properties can be gradually varied, while the content of heparin remains constant. As shown, mesh width, swelling and elasticity modus correlate well with the crosslinking degree of the gel components. In addition, the secondary transformation of heparin within the biohybrid gels permits the covalent binding of cell adhesion promoting RGD-peptides. The biohybrid gels were utilized to demonstrate the effect of mechanical and biomolecular signals on the primary nerve cells and neuronal stem cells. The results show the cell specific interaction of synergistic signal giving and the potential of the biohybrid materials to selectively stimulate the cell destiny. Lately, the inventors own work combined the protease sensitive and insensitive cleaving locations for the extensive control about rates of degradation of heparin-starPEG-hydrogel networks with orthogonally modulated elasticity, RGD-peptide presentation and VEGF-release. Enzymatic cleaving was massively accelerated when the protease access of the gels through non-enzymatic cleaving of ester bonds was increased. The effect of the degradation sensitivity of the gels was investigated for the three dimensional growth of human endothelial cells. Gels with accelerated degradation and a release of VEGF-release lead to a noticeable increase of the penetration of endothelial cells in vitro as also in the blood vessel density in chicken chorioallantois-membrane-test (HET-CAM) in vivo. Thus, the combination of protease sensitive and insensitive cleaving sites can reinforce the degradation of bio-responsive gel materials in such a way that increases the morphogenesis of the endothelial cells.

Artificial protein hydrogels, which are synthesized by interaction of leucine-zipper domains have the ability to self-organize through the protein sequences. Tirrel et al. (W. Shen, K. Zhang, J. A. Kornfiled, D. A. Tirrell, *Nature materials* 2006, 5, 153-15) have developed a hydrogel combined through the double helix domain. Investigations of the structural and dynamic properties of AC1OA-hydrogels in closed systems showed that these multidomain protein chains have a strong tendency to form intramolecular loops. This leads to a rapid gel erosion. Thus, the system was improved, wherein it could be shown that the erosion speed of the protein hydrogel though exploitation of a selective molecular recognition, through a determined aggregation number and through orientation discrimination of twin helical domains, can be coordinated. Experiments have shown that the interaction between molecules during the self-organization and gelation function does not function as simple as a "key-in-lock" process. Instead, the dynamics and thermodynamics determines the entire system of physical and biochemical properties of the resulting polymer matrices. Since such physical and chemical parameters cannot be simply investigated and predicted, through the inventors' own work of the present invention, a screening method was applied in order to find an optimal self-organizing system of matrices through the synthesis of many different peptides and the investigation of their structure-function relationship.

The recognition between base pairs from two complementary DNA-sequences is likely the best characterized and most widely applied interaction between biomolecules. This base pair recognition is not only the topic of a multitude of genetic and biochemical research, but is also an increasingly useful tool in the material sciences. For example, the much promising DNA-origami technology was developed for the construction of nanostructures of any form and topology. DNA based hydrogel systems were recently developed that polymerize though DNA-self-organizing and/or enzyme catalyzed DNA ligation. Luo et al. (S. H. Um, J. B. Lee, N. Park, S. Y. Kwon, C. C. Umbach, D. Luo, *Nature materials* 2006, 5, 797-801) have reported on the complete construction of a hydrogel from branched DNA. Since the DNA is an essential component in biology, these DNA-hydrogels are biocompatible, biologically degradable, can be efficiently produced and in simple manner they can be rendered into any desired form and size. Gelation processes of the DNA can be realized under physiological conditions. The coating of proteins and cells can be carried out in situ. In addition, the fine tuning of these hydrogels can be realized by adjusting the starting concentration and kinds of branched DNA monomers. The most important outcome was that the resulting polymer matrices showed highly defined structures in the nanometer range and a good alignment with the prognosis regarding the DNA double helix structure.

Disadvantageously, the hydrogel system based on the peptide-starPEG conjugate and LMWH-starPEG-conjugate has proved to be very soft and thus not suitable for many construction processes. The peptide sequences of the AT-III-Peptide and the HIP-Peptide originate each from heparin binding protein antithrombin III (ATIII) and HIP (HIP=heparin/heparan sulfate interacting protein), each of which exhibit biological activities itself. In similar manner, the growth factor dimer as well as the VEGF-gel have the potential risk to produce an undesired reaction from the cells or from the host. Growth factors are present in the body in only small amounts and also are effective at very low levels. Thus, the gel from the growth factor dimer and the growth factors themselves can be highly toxic. An overdose is very dangerous and can lead from cancer to immediate death.

Various protein-based hydrogels also carry the potential risk to elicit an immune response, since the artificial multi-domain-proteins are recognized through the host immune system as foreign antigens. The DNA-hydrogel for laboratory utilization can be produced at reasonable cost, while the synthesis at a larger scale can become very expensive. While it is chemically possible to incorporate other bioactive functional groups and/or chemical/physical reactive groups into the DNA-hydrogel, it would however raise the production cost considerably. Most chemical networking reactions for the polymerization would lead to a modification of the cell surface molecules and toxic for the cells. The thiol-ene or thiol-maleimide-addition reactions are thus relatively mild, so that the alkene and the maleimide can react with free thiol groups of the cell surface molecules, while the thiol group in the polymer will have a disulfide-binding exchange reaction with the disulfide-bonds containing cell surface protein. Copper-free click chemistry represents the best suitable strategy for the chemical in situ gel formation. However, the cyclooctin structure is very lipophilic and could form a hydrophobic cluster in a polymer matrix. Moreover, the metabolism and the toxicity of the resulting triazole structure are unknown and have to be determined in clinical tests.

Object of the invention is to provide synthetic systems of polymer matrices by means of a rational design concept. With this system, an improvement of properties for biological and clinical applications is to be realized.

SUMMARY

The solution of the object of the present invention consists in a non-covalent self-organizing hydrogel matrix for biotechnological applications comprising a covalent peptide-polymer conjugate, wherein the covalent peptide-polymer comprises two or more peptides, which are coupled to a polymer chain. The peptide sequence includes a repeated dipeptide-motif (BA)n where B is an amino acid with positively charged side chain, A is alanine and n is an integer between 4 to 20, which represents the number of each repeating dipeptide module (BA) within the dipeptide-motif (BA)n. The amino acid B is preferably arginine with a one-letter code R, or Lysine characterized by the one letter code K. The hydrogel according to the invention is suitable for the formation of a non-covalent hydrogel matrix, which exhibits polymer peptide-conjugate properties. The integer n is preferably selected from 4 to 18, 4 to 16 or 4 to 14. More preferably, n is an integer between 4 to 12, 4 to or 4 to 8. Most preferably, n is an integer between 5 and 7. Even most preferably n is an integer selected from 5 and 7. According to the invention, it is especially preferred, when (BA) is selected from (KA) and (RA) and n is 5 or 7. In one most preferred embodiment, (BA)n is therefore (KA)$_5$ or (KA)$_7$. In a further most preferred embodiment, (BA)n is (RA)$_5$ or (RA)$_7$.

With the present invention an in situ self-forming hydrogel system is provided. The polymer matrices can be formed by simple mixing of two components that are completely compatible with cell-embedding experiments. In addition, a series of peptide-polymer conjugates were investigated in order to test their capacity to bond with an oligosaccharide to form a hydrogel. This approach does not only lead to a series of gel systems with various physical, chemical and biological properties, but also gives a view into the structure-function relationship. Thus, chemical, physical, biochemical and biological tests were carried out in relation to the resulting hydrogels. Since the peptide sequences are based on the simple (BA)n motif, investigations on the structure-function relationship have shown that very simple changes in the sequences can lead to a multitude of gel property changes.

BRIEF DESCRIPTION OF THE DRAWINGS

Other features and advantages of the present invention will be more readily apparent upon reading the following description of currently preferred exemplified embodiments of the invention with reference to the accompanying drawing, in which:

FIG. 1 is a schematic illustration of a selective method for detecting the formation of a hydrogel with heparin, FIGS. 2A and 2B show the results of the reverse-phase-ultrahigh pressure fluid chromatography (UPLC) of purified peptides KA7 (FIG. 2A) and KG7 (FIG. 2B), FIGS. 3A and 3B show the results of the reverse-phase-ultrahigh pressure fluid chromatography (UPLC) of purified peptide-four-arm polyethylene glycol-conjugate (peptide-starPEG) containing the peptide KA7 (FIG. 3A) or KG7 (FIG. 3B), FIGS. 4A-4F show an analysis of a heparin-dependent structural change through circular dichroism-spectroscopy of the heparin binding-peptides KG7 (FIG. 4A), KA5 (FIG. 4B), KKA5 (FIG. 4C), dKA7 (FIG. 4D), KA7 (FIG. 4E) as well as ATIII and RA7 (FIG. 4F), FIGS. 5A and 5B show a deformation of the surface of the 50 µl hydrogel in a 0.2 ml reaction tube, more specifically FIG. 5A below the speed required for deforming the surface, and FIG. 5B at the speed required for deforming the surface. FIG. 5C is a schematic representation of the penetration of a small spheres through 50 µl hydrogel in a 0.2 ml reaction tube depending on the force exerted by the 45° centrifuge.

FIG. 7A shows the amplitude course of the pure peptide-starPEG-conjugate and the pure 14-kDa-heparin with a frequency of 1 Hz. FIG. 7B shows the frequency course of the pure peptide-starPEG-conjugate and the pure 14-kDa-heparin with 2% amplitude. FIGS. 7C and 7D show the flow behavior of peptide-starPEG-conjugate as mixture with 14-kDa-heparin.

FIGS. 12A to 12F show the results of the MTT tests for 14-kDa-heparin (FIG. 12 A,) ATIII-starPEG-conjugate (FIG. 12B), KA5-starPEG-conjugate (FIG. 12C), RA5-starPEG-conjugate (FIG. 12D), KA7-starPEG-conjugate (FIG. 12E) and RA7-starPEG-conjugate (FIG. 12F).

FIGS. 13B and 13E show Live/Dead® Assay stained HDFn.

FIGS. 24A-24F show a scheme and measurement results for a controlled release of Fluorescein-tagged peptide tags, antibody and cyclosporin A from heparin-KA7-starPEG hydrogel. FIG. 24A depicts the interaction of the involved hydrogel components of KA7-starPEG conjugate, heparin and fluorescein-tagged peptide. FIG. 24B shows a scheme of the experimental setup. the tagged peptide was mixed with the conjugate precursor solution and the hydrogel was formed after mixing with the oligosaccharide solution. After gelation, cell culture media was added, in which the tagged peptide was released over time. The supernatant was sampled and measurement for fluorescent intensity at indicated time points. FIG. 24C shows calculated cumulative release of KAn peptides with n of 3 to 7 obtained from corresponding fluorescence measurements in relation to a control. FIG. 24D shows calculated cumulative release of RAn peptides with n of 3 to 7 and the ATIII peptide obtained from corresponding fluorescence measurements in relation to a control. FIG. 24E shows the cumulative release of FITC-tagged IgG antibody from heparin-KA7-starPEG hydrogel with different concentrations of heparin used. FIG. 24F shows the cumulative release of ATIII-cyclosporin A (CsA) from heparin-KA7-starPEG hydrogel monitored by PPlase activity assay.

FIGS. 25A-25C show that monodisperse hydrogel beads made of dextran sulfate and rhodamine labelled KA7-starPEG using a microfluidic system can release FITC-labeled IgG antibody. FIG. 25A depicts the interaction of the involved hydrogel components, KA7-starPEG conjugate and dextran sulfate. The microfluidic system is schematically indicated in FIG. 25B. FIG. 25C shows a picture of hydrogel beads made of dextran sulfate and rhodamine labelled KA7-starPEG. Grey values of the fluorescent image were inverted and then converted into binary values. FIG. 25D shows the release profile of FITC-labeled IgG antibody from the hydrogel beads.

DETAILED DESCRIPTION

Figure 4B:
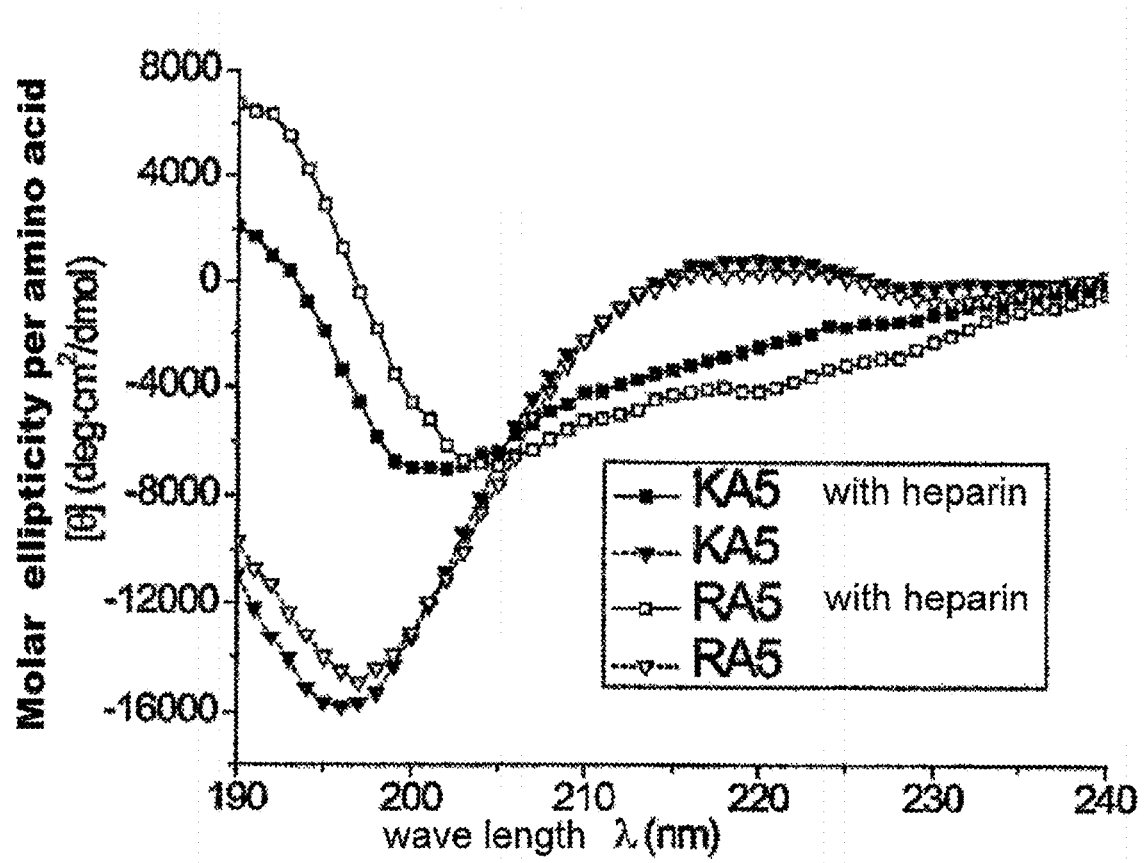

In accordance with the embodiment of the present invention, the polymer chain is formed by a linear multi-arm polyethylene glycol (PEG). Especially preferred is an embodiment where the polymer chain is formed of a four-armed polyethylene glycol (starPEG). Amino acid B is preferably arginine or lysine. Besides L-and D-amino acids of arginine and lysine of the natural amino acids, but principally suitable are all non-natural amino acids that are positively (basic) charged.

Corresponding to a specifically preferred embodiment of the present invention, the hydrogel matrix comprises in addition a highly negatively charged oligosaccharide. According to this embodiment, an oligosaccharide/peptide/polymer-system exists where the peptide is chemically conjugated to the polymer and the gel formation is carried out through mixing the peptide-polymer-conjugate and the oligosaccharide. The non-covalent macromolecular self-organization is also induced by the interaction of the peptide and the oligosaccharide. The choice of the polymer and the oligosaccharide can lead to various gel properties including the flow behavior, the gelation condition and the gelation speed as well as adjustable affinity of peptides interacting with bioactive proteins, for example, growth factors or morphogen. However, the greatest multitude in gel properties is surprisingly realized through changes of a simple and repeating peptide sequence motif. In this manner, the flexible design of the peptide sequence can lead to a broad variety of gel properties, that not only lead to the above-stated rheological properties, the gelation condition, the gelation speed and protein binding properties, but also leads to properties such as for example biological degradation due to proteolytic hydrolysis or other enzymatic activity such as light impact sensitivity.

The highly negatively charged oligosaccharide, according to an advantageous embodiment, is a sulfated or phosphorylated oligosaccharide, preferably selected from a group of oligosaccharides, which comprises heparin, dextran sulfate, α-cyclodextrin sulfate, β-cyclodextrin sulfate, γ-cyclodextrin sulfate, α-cyclodextrin phosphate, β-cyclodextrin phosphate and γ-cyclodextrin phosphate. More preferably, said oligosaccharide is a highly negatively charged sulfated oligosaccharide selected from the group consisting of heparin, dextran sulfate, α-cyclodextrin sulfate, β-cyclodextrin sulfate and γ-cyclodextrin sulfate. In an especially preferred embodiment for an oligosaccharide/peptide/polymer system the hydrogel matrix comprises heparin as oligosaccharide, which originates from the mucosa of pig intestine or bovine lung tissue. Heparin is preferably of pharmaceutical quality. In an alternative embodiment the hydrogel matrix comprises dextran sulfate as oligosaccharide, which preferably has a molecular weight in the range of 4 kDa to 600 kDa. Preferred is the use of dextran sulfate of pharmaceutical quality. If the hydrogel matrix contains cyclodextrin sulfate, then it is preferably α-cyclodextrin sulfate, β-cyclodextrin sulfate, γ-cyclodextrin sulfate of pharmaceutical quality, wherein the sulfation degree is three sulfates per molecule up to a complete sulfation. If the hydrogel matrix contains α-cyclodextrin phosphate, β-cyclodextrin phosphate, γ-cyclodextrin phosphate, then it is of pharmaceutical quality, wherein the degree of phosphorylation comprises three phosphate groups per molecule up to the complete phosphorylation.

According to a most preferred embodiment, the invention provides a hydrogel matrix comprising a mixture of covalent peptide-polymer conjugates and an oligosaccharide;
  wherein said oligosaccharide is a highly negatively charged sulfated oligosaccharide selected from the group consisting of heparin, dextran sulfate, α-cyclodextrin sulfate, β-cyclodextrin sulfate and γ-cyclodextrin sulfate; wherein said polymer comprised in said peptide-polymer conjugates is a linear or multi-arm polyethylene glycol;
  wherein said peptide comprised in said peptide-polymer conjugates is a peptide, which consists of an amino acid sequence selected from the group consisting of SEQ ID NO.4, SEQ ID NO.5, SEQ ID NO. 18 and SEQ ID NO. 19; and
  wherein said hydrogel matrix is configured in the form of an oligosaccharide/peptide/polymer system, in which said peptide is chemically conjugated to the polymer such that the hydrogel is obtained by mixing the peptide-polymer conjugate and the oligosaccharide.

According to a further embodiment of the present invention the hydrogel matrix comprises a chemical group that is light-cleavable between the polymer chain and the peptide sequence, which includes the repeated dipeptide-motif (BA)n. The hydrogel matrix can also comprise the pH sensitive chemical linker between polymer chain and peptide sequence, which includes the repeating dipeptide-motif (BA)n. In accordance with another embodiment of the present invention the hydrogel matrix also comprises an enzymatic cleavable linker between the polymer chain, preferably a PEG molecule, and the peptide sequence, which includes the repeating dipetide-motif (BA)n. The hydrogel comprises as enzymatic cleavable linker also an oligonucleotide sequence, which is a nuclease-active substrate.

The modification of the peptide can lead to a further development of the hydrogel function through the insertion of different markers, for example fluorescence marking for monitoring the matrices in vivo and in vitro and for the further development of the active-compound-conjugation for an active compound release. Also, since the gel formation is induced by two chemically defined components, the matrix-system can be formed layer-by-layer, in order to place a peptide-polymer-conjugate and/or an oligosaccharide with a certain function at predetermined layer with high precision. The layer-by-layer method, in combination with the above-stated embodiment of the light sensitive hydrogel matrix, renders possible a design and construction of sophisticated bioactive and biocompatible nanostructure and nano units.

All components in the hydrogel system according to the present invention can be produced and retained in a comparably inexpensive manner. Heparin, dextran sulfate and cyclodextrin sulfate and also maleimide functionalized PEG-polymer are available at relatively low cost from commercial sellers. Peptides can be synthesized in a solid-phase-peptide-synthesizer in the lab on the scale of grams at relatively low cost. Advantageously, the elasticity of the hydrogel matrix in accordance with the above-described embodiments can be adjusted by using (BA)n linker of different length and different concentrations from low as 0.5 mM to 8 mM. The elasticity modulus can be set to at least 10 Pa until up to 30 kPa. Thus, the hydrogel well represents the natural range of elasticities of human tissue from soft tissue of the brain to rigid properties of bone.

The self-organizing system can be also used in a microfluid system in order to produce hydrogel beads as well as cells to be embedded into the hydrogel beads. A further aspect of the present invention thus refers to hydrogels with a self-organizing matrix forming hydrogel. Into a self-organizing hydrogel matrix formed from the hydrogel according to the present invention or into the hydrogel beads according to the present invention, as already noted, cells can be embedded via a corresponding method resulting in a corresponding composite. Hereby, the cells are preferably selected from a group, which comprises mammalian cells, insect cells, bacteria cells and yeast cells. If the cells are mammalian cells, different cancer cell lines, fibroblast cells, pluripotent stem cells, induced pluripotent stem cells, human T-cells or human B-cells, can be advantageously selected. Cells embedded in a hydrogel matrix or respectively, hydrogel beads can be utilized for the production of proteins, wherein the protein preferably comprises therapeutic monoclonal antibodies.

A further aspect of the present invention refers to capsules for the targeted release of therapeutic reagents, wherein via a corresponding method therapeutic reagents are encapsulated with the above-described hydrogel matrix or the above-described hydrogel beads. The group of each of the utilized therapeutic reagents comprises preferably mammalian cells, insect cells, bacteria, yeast cells, anti-cancer compound, anti-coagulation compounds, anti-inflammatory compounds, immune-suppressive compounds, therapeutic antibodies, diagnostic reagents, hormones, growth factors, cytokine, small molecules as inhibitors for growth factors, small molecules as inhibitors for cytokines, aptamer-inhibitors for growth factors and aptamer-inhibitors for cytokine.

A further aspect of the invention refers to a composition of a non-covalent self-organizing hydrogel matrix in one of the above-described embodiments and chemicals and therapeutic reagents, wherein in the nascent therapeutic hydrogel a gradient of chemicals and reagents is produced. This means, it is possible through a suitable method to produce a gradient of chemicals and reagents in the therapeutic hydrogel matrices respectively the hydrogel beads according to the present invention. Possible therapeutic chemicals and reagents, which form gradients in the hydrogel matrix are preferably anti-coagulation compounds, anti-inflammatory compounds, immune-suppressive compounds, therapeutic antibodies, diagnostic reagents, hormones, growth factors, cytokine, small molecules as inhibitors of growth factors, small molecules as inhibitors for cytokine, aptamer-inhibitors for growth factors as well as aptamer-inhibitors for cytokine.

Finally, a further aspect of the present invention is a hybrid system of a hydrogel matrix according to the present invention, which, on the one hand are not in spherical shape, and hydrogel beads on the other hand. Hereby, the non-spherical hydrogel matrix and the hydrogel beads each exhibit a different chemical composition and one component of the hybrid system is controllable through light, through selective chemical degradation or through enzymatic digestion.

A simple self-repeating peptide motif, which can be simply modified to lead to various binding properties at certain biomolecules is of great interest in biochemistry, biotechnology and in the biomaterial sciences. For example, such a system can be utilized to design adjustable self-organizing non-covalent matrix systems. Heparin was used as a starting compound in order to synthesize a covalent hydrogel platform to support cell replacement therapies. Following is a library of peptides, which are each conjugated to a four-armed polyethylene glycol (starPEG), which serves as polymer chain in the examples of the embodiments. The library leads to the determination of a minimal heparin binding peptide motif (BA)n wherein B is an amino acid residue, for example of arginine or lysine, and wherein A is alanine and n is a number between 4-20. The repetition of this motif or a single amino acid mutation leads to a multitude of physical and biochemical properties of the resulting heparin dependent self-organizing hydrogel.

FIG. 1 shows schematically a selection method for the detection that the specific peptide motif coupled to a four-armed polyethyleneglycol (starPEG) can form a hydrogel with 14 kDa heparin. FIG. 1 makes clear that the hydrogel formation with a heparin induced structural change coincides with the (BA)n-peptide motif.

Table 1 shows first the library of synthesized peptides. Shown are the sequences, the abbreviations and the molecular weight of the peptides.

TABLE 1

| Name | Sequence Identifier (SEQ ID NO) | Peptide Sequence | Molecular weight [$10^{-3}$ kg/mol] |
|---|---|---|---|
| ATIII | 1 | CWGGKAFAKLAARLYRKA | 2010.44 |
| KA1 | 2 | CWGGKA | 670.72 |
| KA3 | 3 | CWGGKAKAKA | 1019.22 |
| KA5 | 4 | CWGGKAKAKAKAKA | 1417.72 |
| KA7 | 5 | CWGGKAKAKAKAKAKAKA | 1816.22 |
| dKdA7 | 6 | cwGGkakakakakakaka | 1816.22 |
| dKA7 | 7 | CWGGkAkAkAkAkAkAkA | 1816.22 |
| KdA7 | 8 | CWGGKaKaKaKaKaKaKa | 1816.22 |
| KA7-1a | 9 | CWGGKAKAKaKAKAKA | 1816.22 |
| KKA5 | 10 | CWGGKKAKKAKKAKKAKKA | 2058.57 |
| KG1 | 11 | CWGGKG | 606.69 |
| KG3 | 12 | CWGGKGKGKG | 977.13 |
| KG5 | 13 | CWGGKGKGKGKGKG | 1347.57 |
| KG7 | 14 | CWGGKGKGKGKGKGKGKG | 1718.01 |
| KKG5 | 15 | CWGKKGKKGKKGKKGKKG | 1988.42 |

TABLE 1-continued

| Name | Sequence Identifier (SEQ ID NO) | Peptide Sequence | Molecular weight [$10^{-3}$ kg/mol] |
|---|---|---|---|
| RA1 | 16 | CWGGRA | 648.74 |
| RA3 | 17 | CWGGRARARA | 1103.28 |
| RA5 | 18 | CWGGRARARARARA | 1557.82 |
| RA7 | 19 | CWGGRARARARARARARA | 2012.36 |
| RRA5 | 20 | CWGGRARRARRARRARRA | 2338.77 |
| RG1 | 21 | CWGGRG | 634.71 |
| RG3 | 22 | CWGGRGRGRG | 1061.19 |
| RG5 | 23 | CWGGRGRGRGRGRG | 1487.67 |
| RG7 | 24 | CWGGRGRGRGRGRGRGRG | 1914.15 |
| RRG5 | 25 | CWGRRGRRGRRGRRGRRG | 2268.62 |

Preferred according to the invention are peptides which have an amino acid sequence selected from the group consisting of SEQ ID NOs: 4, 5, 18 and 19, which comprise the (BA)n peptides selected from the group consisting (KA)$_5$, (KA)$_7$, (RA)$_5$ or (RA)$_7$.

Following are the one letter codes for the respective amino acids and (in parenthesis) opposite thereto their 3-letter codes:
A is the abbreviation for Alanine (Ala)
C for Cysteine (Cys)
F for Phenylalanine (Phe)
G for Glycine (Gly)
K for Lysine (Lys)
L for Leucine (Leu)
R for Arginine (Arg)
W for Tryptophan (Trp) and
Y for Tyrosine (Tyr)

L-amino acids are marked by the use of upper case letters, D-amino acids by lower case letters.

All peptides shown in Table 1 are produced by utilizing a standardized-fluorenylmethoxycarbonyl chemistry (FMOC chemistry) on a solid phase with 2-(1H-benzotriazol-1-yl)-1,1,3,3 tetramethyluronoiumhexafluorophosphate-activation (HBTU-activation) in an automatic solid phase peptide synthesizer (ResPep SL, Intavis, Cologne, Germany). To obtain good peptide quality, each amino acid was coupled two times with the fivefold excess, wherein all non-reacting amino groups were protected with acetic acid anhydride. For cleaving the peptide from the resin, the resin was treated for one and one half hour with a mixture of trifluoroacetic acid (TFA) triisopropylsilane(TIS)/water/dithiothreitol (DTT), wherein these components are present in a ratio of 90 (v/v):2.5 (v/v):2.5 (v/v):2.5 (m/v).

The peptides were dissolved in water, which contained 2 mg/ml tris(2-carboxyethyl)phosphine (TCEP). The peptide purification was carried out by means of reverse-phase high pressure liquid chromatography (UPLC) on a preparative HPLC-device (Prostar™, Agilent Technologies, Santa Clara, USA), which was provided with a preparative C18-column (AXIA™ 1001A grain size 10 μm, 250×30 mM, Phenomenex Torrance, USA). The peptide was eluted from the column by utilizing a gradient of 5% to 100% solvent B at 20 ml/min, wherein solvent A is 0.1% trifluoroacetic acid (TFA) in water and solvent B is 0.1% TFA and 5% water in acetonitril.

The purity was confirmed through analytical reverse-phase ultrahigh pressure liquid chromatography (UPLC Aquity™ with UV detector, Waters, Milford Mass., USA) provided with an analytical C18-column (AQUITY™ UPLC BEH C18, grain size 1.7 μm, 50×2.1 mM, Waters, Milford, Mass., USA) by utilizing an isocratic gradient and an electrospray-ionisation-mass-spectrometry (ESI-MS) (AQUITY™ TQ detector, Waters, Milford, Mass., USA). The peptide was dry frozen into a white powder (CHRIST ALPHA™ 2-4LD plus+Vacuubrand RZ6) and at 4° C. under dry conditions stored for not more than one week prior to further treatment.

FIG. 2 shows the results of the reverse phase ultrahigh pressure liquid chromatography (UPLC) of purified peptides at 280 nm by utilizing an analytical C18 column and an isocratic gradient. The sample peptides from the library shown in FIG. 2 are A) CWGGKAKAKAKAKAKAKA (KA7) and B) CWGGKGKGKGKGKGKG (KG7)

The synthesis of the peptide-starPEG-conjugates for use in the hydrogel self-organization were carried out through Michael-addition-reactions between maleimide-terminal four-armed PEG and cysteine-terminal peptides from the library. Both components were dissolved in physiological phosphate buffer solution (1×PBS) with a pH value of 7.4 in a molar ratio of 1:4.5 (starPEG:peptide) with a total concentration of 80 mg/ml. The reaction mixture was quickly covered and stirred at 750 rpm at room temperature for 18 hours (MR Hei-Standard, Heidolph, Schwabach, Deutschland). The raw products were analyzed through reverse-phase high pressure liquid chromatography (UPLC) (UPLC Aquity™ with UV detector, Waters, Milford, Mass., USA) by using C18 column (AQUITY™ UPLC BEH C18, grain size 1.7 μm, 50×2.1 mM, Waters, Milford, Mass., USA) and an isocratic gradient. The raw product was dialyzed with a dialysis membrane with cut-off limit of 8 kDa for two days against 10 liters of water under constant water exchange to release unbound peptides and salt. Thereafter, the product was again injected into the UPLC in order to examine the purity as compared to the analysis before the dialysis. The dialyzed product was dry frozen in water into a solid.

FIG. 3 shows the results of the reverse-phase high-pressure liquid chromatography (UPLC)-analysis of purified peptide-starPEG by means of UV detection at 280 nm. The results are shown in FIG. 3 for the sample conjugates from the library A) KA7-starPEG and in B) KG-starPEG.

Following is the description of the production of the hydrogel networks. Hereby 14-kDa-heparin (25 mM, 2.5 mM) and peptide-starPEG conjugates (6.25 mM, 3.125 mM) were dissolved in physiologic phosphate buffer solution (1×PBS) water or cell culture medium with 2% fetal bovine serum (FBS). These solutions were dissolved in a ratio of 1:4 heparin:peptide-starPEG-conjugate by obtaining 0.5 mM or 5 mM 14-kDa-heparin and 2.5 mM or 5 mM peptide-starPEG. The ligand/mol ratio was 2:1, 1:1 and 1:5 relative to the mol ratio of 14-kDa-heparin and the peptide-starPEG-conjugate. The mixtures were incubated within a time frame of one hour to overnight at room temperature of 37° C. The gelation time spanned from present up to several hours depending on the applied peptide motif. A hydrogel was confirmed when added phosphate buffer solution (1×PBS) pH 7.4 did not dissolve nor mix with the hydrogel.

Table 2 shows the selected peptides from the library, which reflect best the structural activity relationship of the hydrogel formation with heparin. ATIII is a heparin-binding peptide known from the literature. All peptides are connected to a four-armed, maleimide functionalized 10-kDa-polyethylene glycol (starPEG). The hydrogel formation was tested in a 50 μl mixture, which contains 5 mM 14-kDa-heparin and 5 mM (2.5 mM) peptide-starPEG conjugate in phosphate buffer solution (1×PBS, pH 7.4). The deformation and penetration speed was analyzed through centrifuging the hydrogel in a 45° table centrifuge with 275 μm metal beads added to the surface. The deformation of the surface and the penetration of the metal beads were monitored in dependence on the applied force.

TABLE 2

| Name | Peptide Sequence | Molecular weight [$10^{-3}$ kg/mol] | Peptide amount [$10^{-3}$ mol/l] | Deformation speed [m/s$^2$] | Penetration speed [m/s$^2$] |
| --- | --- | --- | --- | --- | --- |
| Gel created with heparin | | | | | |
| ATIII | CWGGKAFAKLAARLYRKA | 2010.44 | 5 | Not determined, gel shrank | Not determined |
| KA5 | CWGGKAKAKAKAKA | 1417.72 | 5 | 11223 +/- 4768 | 21209 +/- 2188 |
| KA7 | CWGGKAKAKAKAKAKA | 1816.22 | 2.5 | 43998 +/- 3139 | 72780 +/- 6926 |
| KA7 | CWGGKAKAKAKAKAKA | 1816.22 | 5 | >148317 | 138919 +/- 16275 |
| RA5 | CWGGRARARARARA | 1557.82 | 5 | >687 | >687 |
| RA7 | CWGGRARARARARARA | 2012.36 | 5 | 1069 +/- 579 | 1952 +/- 491 |

The heparin-binding domain of antithrombin III (ATIII) and heparin with low molecular weight can form a soft hydrogel if both are conjugated at starPEG as described in N. Yamaguchi, B.-S. Chae, L. Zhang, K L Kiick, E M Furst, Biomacromolecules 2005, 6, 1931-1940. In order to reduce the chemical complexity, the investigations were carried out with 14 kDa-heparin. It was found that in the presence of ATIII peptide, which is conjugated to starPEG (ATIII starPEG) the resulting hydrogel is formed immediately but does not cover the total volume as shown in Table 2. The investigation of ATIII starPEG and heparin showed that a strong interaction between heparin and peptide does not necessarily lead to an optimal hydrogel-network formation.

Therefore, the library of peptide-starPEG-conjugates was developed in order to investigate the peptide sequences of the heparin dependent self-organizing properties.

The (BA)n sequence opens the possibility to change the peptide length and thus to slightly change the properties.

To follow the goal of attaining the greatest possible flexibility regarding properties, various repeats of (BA)n were synthesized, that are given in the Tables 1 and 2. Single repeats were used as (negative) control as the a-helix formations require at least five amino acids (according to Pauling-Corey-Branson). To be able to compare also charge density dependencies besides length-charge-dependencies while recognizing binding to heparin, $(BBA)_5$ was synthesized (Table 1). $(BBA)_5$, at similar length exhibits a higher charge density than (BA)7. As already stated, B and A have the tendency to form a-helical structures, as is known from C. Nick Pace, J. Martin Scholtz, *Biophysical Journal* 1998, 75, 422-427. To obtain always a tandem of potential structure forming and non-structure forming peptides, as Table 1 shows, each (BA)n and $(BBA)_5$ had a (BG)n- and a $(BBG)_5$-partner, wherein the letter G stands for glycine. Glycine is known for interrupting any kind of structure formation.

In addition to the peptide motif, a tryptophan was labeled with a one letter code W, for UV detection and purification and a cysteine, marked with the one letter code C, bound to the N-terminal end of the peptide with two glycine. By applying the Michael-addition-chemistry, the cysteine was coupled to the maleimide-functionalized 10-kDa-starPEG. Synthesis and coupling of the peptide starPEG-conjugates were optimized regarding purity, speed and simple handling as FIG. 3 shows. This is the largest library of peptide-polymer-conjugates, for which each of the oligosaccharide dependent hydrogel formation was analyzed. To analyze the formation of hydrogels, all peptide-starPEG-conjugates were each mixed with 14-kDa-heparin in 50 µl phosphate buffer (1×PBS) to a final concentration of 5 mM. After overnight incubation the phosphate buffer (1×PBS) was added in order to check which mixtures formed a hydrogel. KA7-, KA5-, RA7- and RA5-starPEG-conjugates with heparin did not mix with 1×PBS but formed a stable, clear hydrogel as Table 2 shows. These are the shortest de novo produced peptides known in the literature to form heparin dependent hydrogels.

In Table 3 peptides from the peptide library are shown that do not form a heparin dependent hydrogel. All peptides are coupled to a 10-kDa-maleimide-starPEG. The gel formation was tested in a 50 µl mixture, which contains 5 mM 14-kDa-heparin and 5 mM peptide-starPEG-conjugate in 1×PBS at a pH value of 7.4.

TABLE 3

| Name | Sequence Identifier (SEQ ID NO) | Peptide Sequence | Molecular weight [10$^{-3}$ kg/mol] |
|---|---|---|---|
| Not formed with heparin | | | |
| KA1 | 2 | CWGGKA | 670.72 |
| KA3 | 3 | CWGGKAKAKA | 1019.22 |
| dKA7 | 7 | CWGGKAkAkAkAkAkAkA | 1816.22 |
| KdA7 | 8 | CWGGKaKaKaKaKaKaKa | 1816.22 |
| KA7-1a | 9 | CWGGKAKAKAKaKAKAKA | 1816.22 |
| KKA5 | 10 | CWGGKKAKKAKKAKKAKKA | 2058.57 |
| KG1 | 11 | CWGGKG | 606.69 |
| KG3 | 12 | CWGGKGKGKG | 977.13 |
| KG5 | 13 | CWGGKGKGKGKGKG | 1347.57 |
| KG7 | 14 | CWGGKGKGKGKGKGKGKG | 1718.01 |
| KKG5 | 15 | CWGKKGKKGKKGKKGKKG | 1988.42 |
| RA1 | 16 | CWGGRA | 648.74 |
| RA3 | 17 | CWGGRARARA | 1103.28 |
| RRA5 | 20 | CWGGRARRARRARRARRA | 2338.77 |
| RG1 | 21 | CWGGRG | 634.71 |
| RG3 | 22 | CWGGRGRGRG | 1061.19 |
| RG5 | 23 | CWGGRGRGRGRGRG | 1487.67 |
| RG7 | 24 | CWGGRGRGRGRGRG | 1914.15 |
| RRG5 | 25 | CWGRRGRRGRRGRRGRRG | 2268.62 |

It is remarkable, that the $(BBA)_5$ did not form a hydrogel with heparin although they exhibit a higher charge density as is shown in Table 3. This behavior must be based on the structure, which were analyzed with the unconjugated peptides.

The de novo produced heparin-binding peptides were analyzed through application of circular dichroism spectroscopy (CD) (J-810, REV. 1.00, Jasco Inc. Eaton, Md., USA). All CD spectra were taken at wave lengths from 185 to 260 nm in a quartz cuvette of 1 mm optical path length. The data points were recorded at each nanometer in a response time of 4.0 sec. All values of molar ellipticity [θ] are shown relative to the median number of peptide bonds in deg cm$^2$ dmol. FIGS. 4A to 4F contain the result of the analysis of heparin dependent structural change through circular dichroism spectroscopy (CD). Hereby the peptides were measured in MilliQ-water alone and together with 14-kDa-heparin in a mol ratio of 1:1. Only for RA7 and KA7 twice as much heparin than peptide was used. The graph for the peptides that were mixed with 14-kDa-heparin, were corrected with the CD spectra of pure 14-kDa-heparin at the same concentration. The range for the peptide concentration was at 74.5 µM to 137.6 µM.

In Milli-Q-water (Advantage A10; Millipore GmbH) not only do (BG)n- and $(BBG)_5$ motifs show a random coil structure, but also (BA)n- and $(BBA)_5$ motifs as shown in FIGS. 4A to 4F. During observation of hydrogel formation of peptide-starPEG-conjugate with heparin, the $(BA)_7$ motif and the $(BA)_5$ motif together with the heparin have shown a structural change. Due to the glycine, the (BG)n motif and $(BBG)_5$ motif cannot change the structure in significant ways, which is also confirmed in the lack of hydrogel formation. RRA7 is the only peptide, which underwent no formation of hydrogel although showing a structural change in the circular dichroism spectroscopy (CD). Due to the denser charge distribution, the optimal distance of the positive charge of the peptide is not given and thus an optimal interaction with the sulfate of the heparin is possible. In conclusion, the (BA)n peptide motif is preferred for heparin-binding peptides, although the (BBA)₅ peptide motif exhibits more positive charge at similar peptide length. This structure/activity relationship between the distance of the basic amino acids to alanine and the heparin binding capacity in the formation of hydrogels is in any event novel and surprising.

Figure 4D:
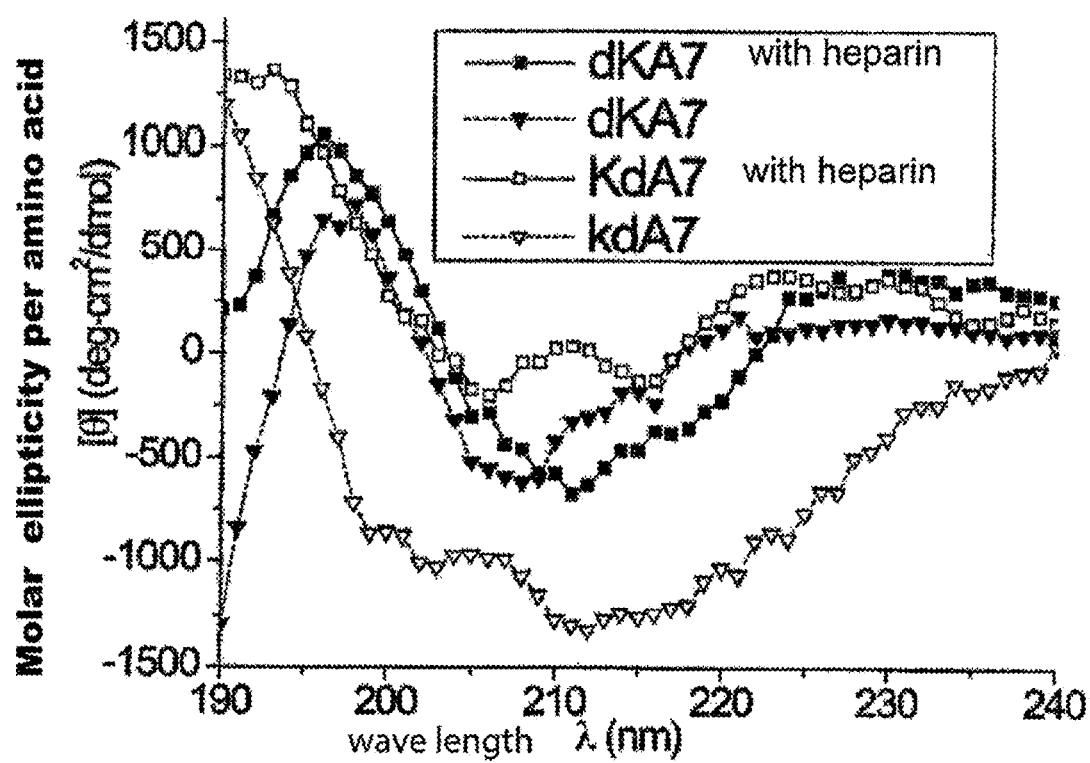
Figure 4E:
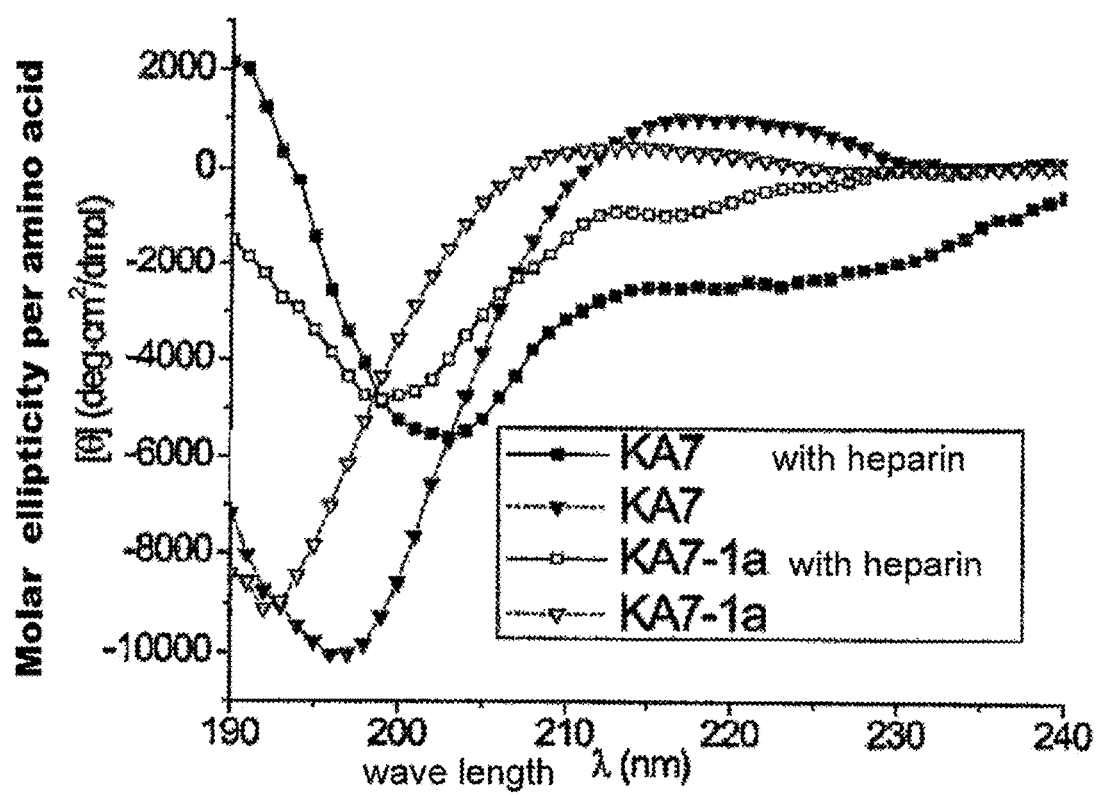
Figure 4F:
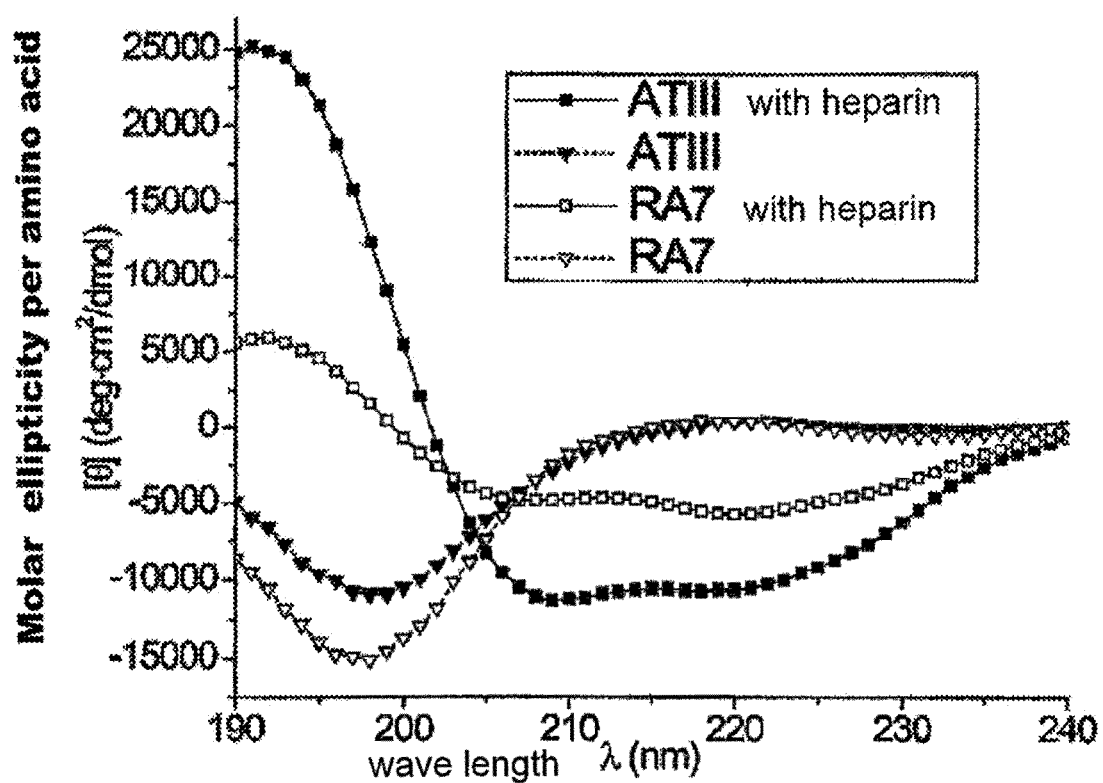

In order to underline the significance of the structure activity relationship of (BA)n motifs, the mutants dKA7 and KdA7 were synthesized (Table 3). By mixing L- and D-amino acids the structure formation was supposed to the hindered. The analysis showed that these mutants show neither formation of a hydrogel with 14-kDa heparin (see Table 3) nor does one of these mutants show a structural change similar as the KA7 exhibits. FIGS. 4D and 4E are illustrating the difference in structural change measured by CD. Likewise, the mutant KA7-1a having an D-alanine in exchange for the L-alanine, in the center of the peptide motif, doesn't form a hydrogel with heparin, as also shown in Table 3. Also no structural change occurs in the CD as shown by FIG. 4E.

A comparative high-throughput analysis was performed regarding the mechanical properties of the hydrogels. In order to provide a fast high-throughput method for comparing small amounts of hydrogel, a tabletop centrifuge (5424R, Eppendorf, Hamburg, Germany) was used. For this purpose, 50 µl of the hydrogel were formed by mixing the peptide-starPEG-conjugates and 14-kDa-heparin in phosphate buffer (1×PBS, pH 7.4) to a final concentration of 5 mM (once 2.5 mM for KA7-starPEG). The mixture was incubated in 0.2 ml reaction vessels overnight. The deformation of the hydrogel surface was determined in reference to the 45° centrifuge rotor and the penetration of 275 µm metal beads in dependence on the force that has to be produced by the centrifuge. All experiments were repeated three times.

Figures 5A, 5B, 5C:
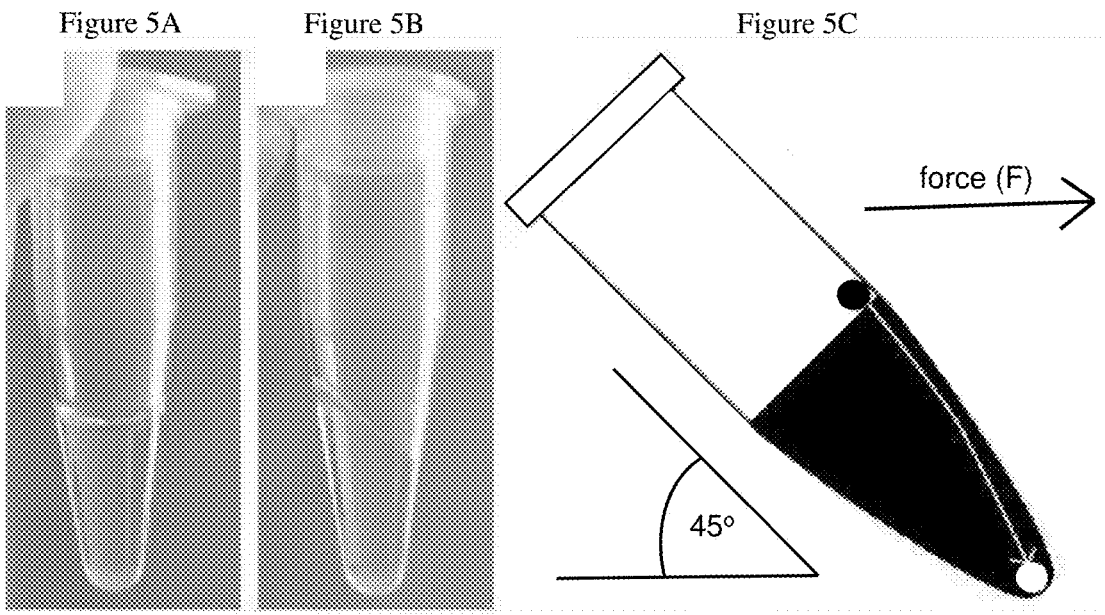
FIGS. 5A-5C are schematic illustration of a high throughput analysis of the mechanical properties of the hydrogels.

FIG. 5 schematically shows the high-throughput analysis regarding the mechanical properties of the hydrogels. Hereby FIGS. 5A and B show a deformation of the surface of the 50 µl hydrogel in a 0.2 ml reaction tube, more specifically FIG. 5A below the speed required for deforming the surface, and FIG. 5B at the speed required for deforming the surface. FIG. 5C is a schematic representation of the penetration of a small spheres through 50 µl hydrogel in a 0.2 ml reaction tube depending on the force exerted by the 45° centrifuge.

It was shown that the RA5-PEG-hydrogel with heparin produced similar results as the mixtures with RRA7-starPEG, which had not formed a hydrogel, see Tables 2 and 3. The RA7-, KA5- and KA7-based hydrogels are much stronger and according to Table 2 exhibit a broad range of stiffness. Arginine and lysine have different charge distributions on the side chain, which leads to different properties. The two different concentrations of KA7-starPEG with heparin resulted in hydrogels with different mechanical properties as can be seen in Table 2. This shows that the hydrogel, which is based on a non-covalent peptide-biomolecule-interaction, can be adjusted in different ways. It is possible to experiment with the concentration of the components and with the peptide sequence. Mixtures of different (BA)n-peptide-motifs on a starPEG-molecule or different peptide-starPEG-conjugates would even further improve the capability for adjustment in smaller steps.

Figure 6:
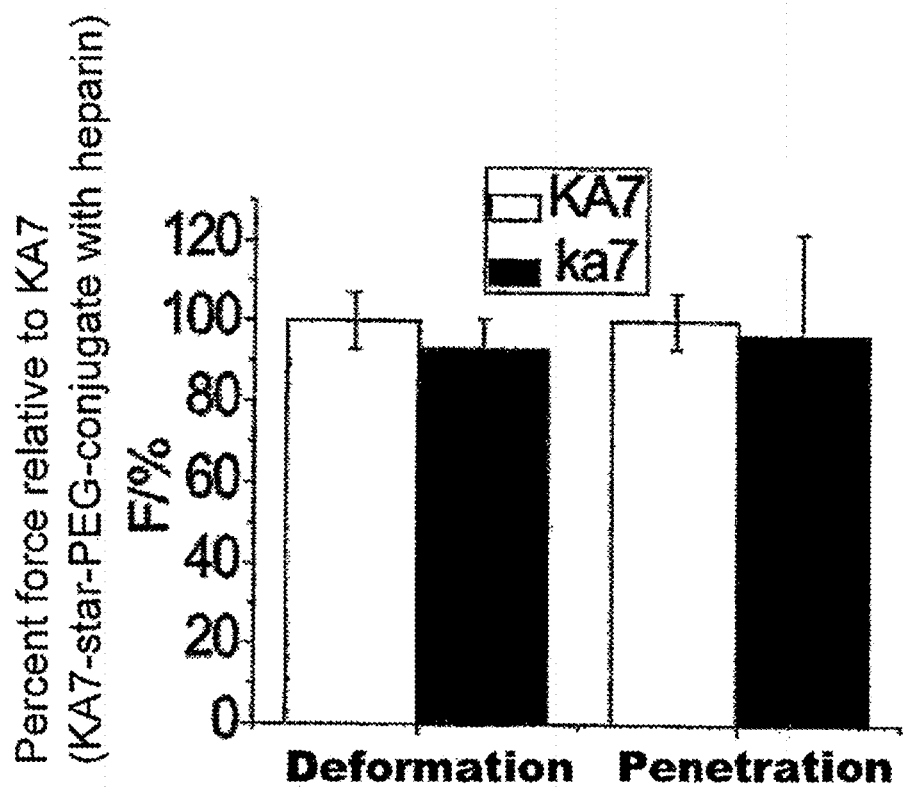
FIG. 6 shows the stability of a lysine and alanine-based hydrogel with comparison of L- and D-amino acids.

FIG. 6 shows the stability of a lysine and arginine based hydrogel in comparison to L- and D-amino acids. The hydrogels were formed by mixing peptide-starPEG-conjugate and 14-kDa-heparin at 5 mM final concentration in 50 µl phosphate buffer (1×PBS). The analysis was performed by centrifuging the hydrogels in a 45° tabletop centrifuge with 275 µm metal beads on the gel surface. The deformation of the surface and the penetration of the spheres were recorded in dependence on the exerted force.

An important result was that the complete change of the KA7 to D-amino acids has no influence on the hydrogel stiffness, as shown in FIG. 6. Due to the resistance of, D-amino acids against proteases it is possible to create non-covalent hydrogels that are very stable in biological environments. In this way the degradability can be adjusted by different amino acids.

In order to test the broad spectrum of the mechanical properties according to Table 2, a rheological test was performed. The flow behavior of the KA7-starPEG- and KA5-starPEG-hydrogels with heparin was determined via frequency sweep and load sampling experiments.

Figure 7A:
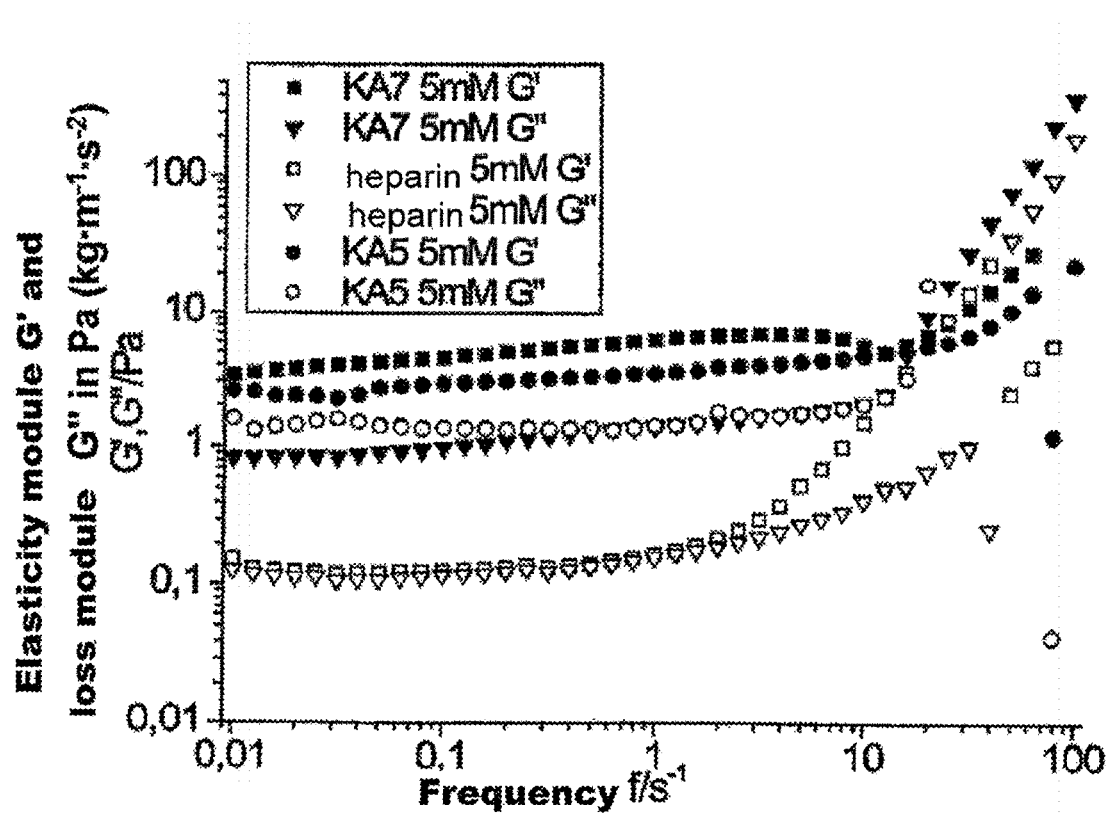
FIGS. 7A-7D show the flow behavior of the KA7-starPEG- and KA5-starPEG-hydrogels with heparin was determined via frequency sweep and load sampling experiments.
Figure 7B:
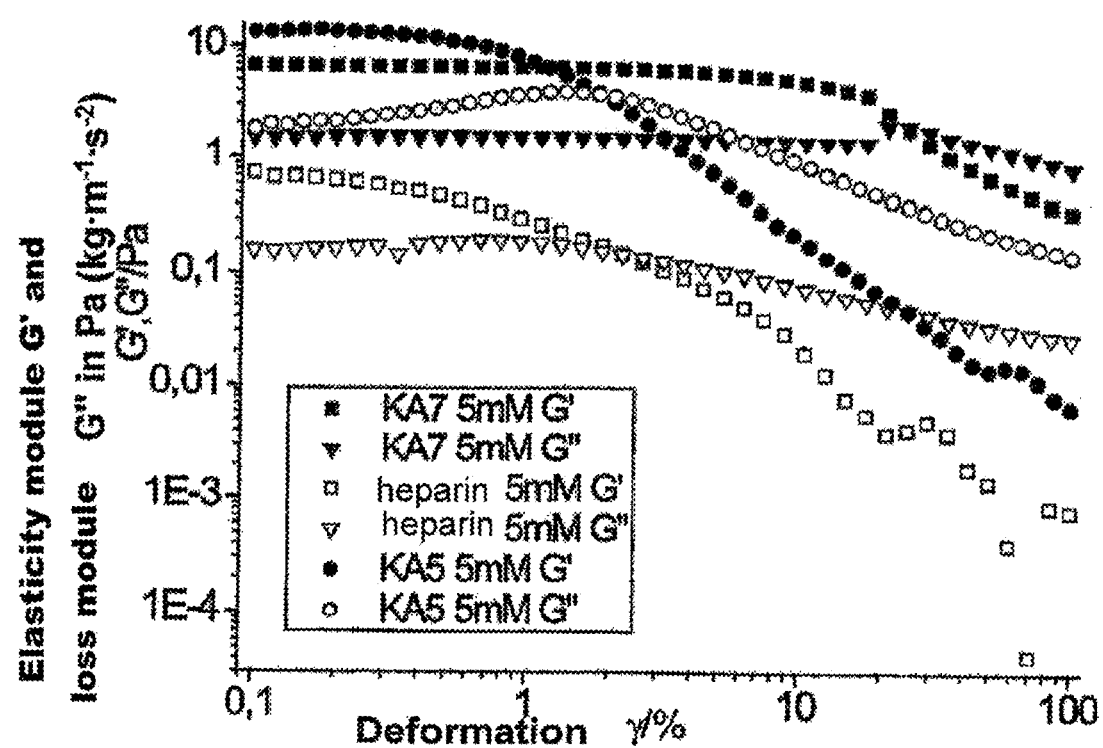
Figure 7C:
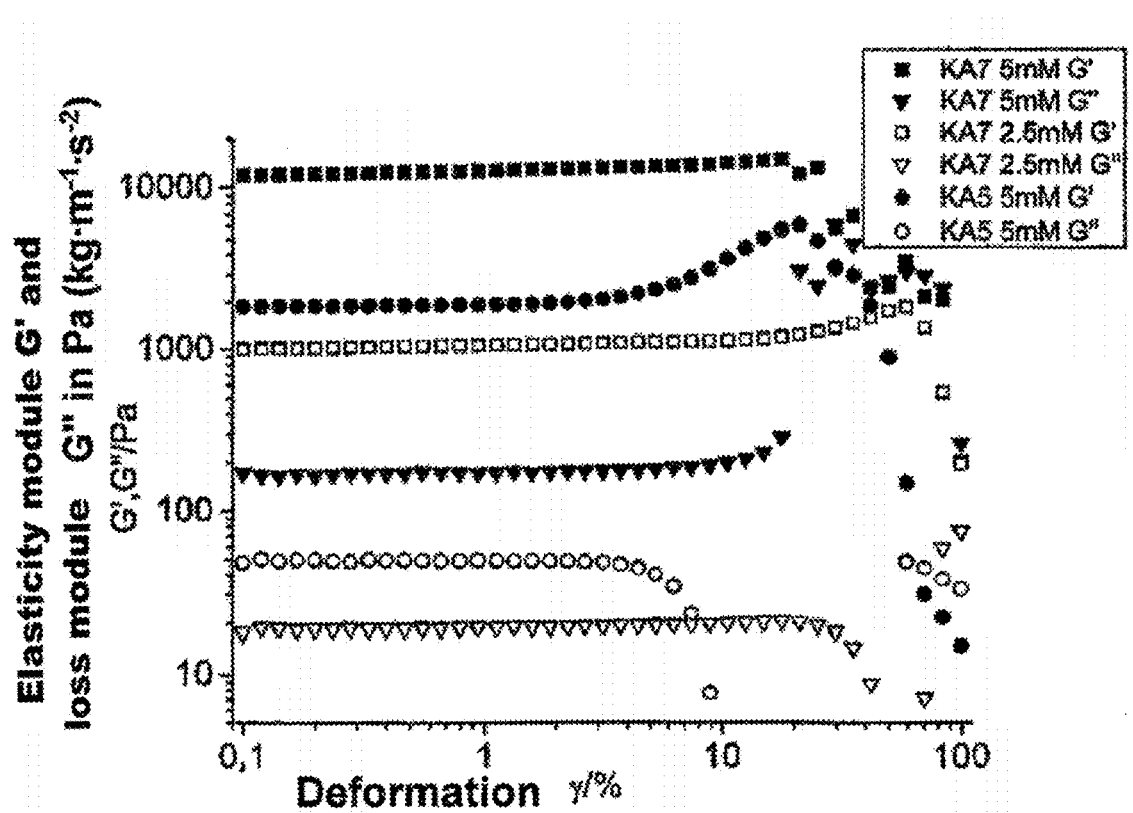
Figure 7D:
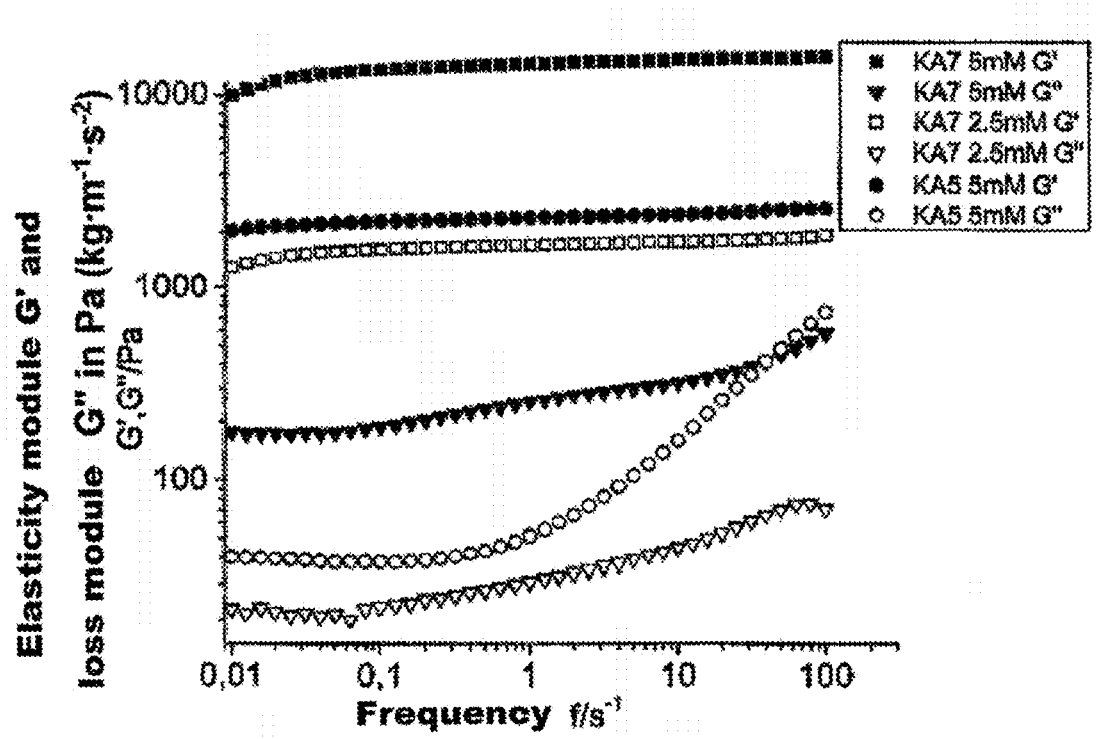

FIG. 7A shows the amplitude course of the pure peptide-starPEG-conjugate and the pure 14-kDa-heparin with a frequency of 1 Hz. FIG. 7B shows the frequency course of the pure peptide-starPEG-conjugate and the pure 14-kDa-heparin with 2% amplitude. FIGS. 7C and 7D show the flow behavior of peptide-starPEG-conjugate as mixture with 14-kDa-heparin. The final mixture in phosphate buffer solution (1×PBS) contains of both 5 mM or 2.5 mM peptide-starPEG-conjugate and 5 mM or 0.5 mM heparin. The solutions or the mixtures were analyzed by using a shear-stress controlled rheometer (MCR 301, Paar Physica, Anton Paar, Ashland, Va.) at 20° C. and a measuring unit with 39.979 mM diameter, an angle of 0.305° and a truncation of 24 µm.

The individual-component solutions of 14-kDa-heparin, KA5-starPEG and KA7-starPEG were analyzed in order to show the basic mechanical properties of the starting components in comparison to the mechanical properties of the mixtures. The individual-component-peptide-starPEG-solutions were treated identically to the mixtures containing 14-kDa-heparin. All mixtures and solutions were incubated in an environment that was completely closed to prevent evaporation. All incubation times were determined by gelation time experiments described below. The final mixture of 5 mM KA5-star-PEG and 5 mM 14-kDa-heparin was incubated for 1.5 hours. The final mixture of 2.5 mM KA7-starPEG and 5 mM 14-kDa-heparin was incubated for 3 hours. The final mixture of 5 mM KA5-starPEG and 5 mM 14-kDa-heparin was incubated for 15 hours. The amplitude course measurements were performed with a frequency of 1 Hz over a range from 0.1% to 100%. The frequency dependencies were detected by using a 1% amplitude and in a range of 0.01% to 100%. All experiments where repeated twice and the mean value plotted.

The storage modulus G' was significantly higher for all samples than the loss modulus G" (−2%). These viscoelastic properties confirm that the interaction between the (KA)n and heparin is very strong and stable. The stiffness of the pure 14 kDa-heparin or the pure peptide-star-conjugate is very low as shown in FIGS. 7A and 7B. The broad concentration spectrum of heparin that can be used ranges from 0.5 to 5 mM. Also the mechanical properties can be adjusted by a factor of more than 10 solely by changing the concentration of the components. The mixing of different peptide-starPEG-conjugates is an additional way to change the gel properties. This provides two dimensions, the concentration and the peptide sequence that can be changed individually or together in order to adjust the hydrogel properties to the application at hand. This is possible solely based on the interaction of the peptide-motif (BA)n with the biomolecule heparin.

In order to test the strength of the interaction between the peptide motif and the 14-kDa-heparin the formed hydrogels were tested with regard to different solvents. Table 4 shows the result of this test of stability against different solvents. For this the peptide-starPEG-conjugates were mixed with 14 kDa-heparin in 50 µl in physiological phosphate buffer solution (1×PBS) to a final concentration of respectively 5 mM. Each solvent, i.e., physiological phosphate buffer solution (1×PBS), Milli-0-water, 1 M hydrochloric acid (HCl) 1 M sodium hydroxide solution (NaOH), saturated sodium chloride solution (NaCl), dimethyl sulfoxide (DMSO), ethanol and cell culture medium with 2% fetal bovine serum (FBS) were respectively added as 200 µl supernatant to the hydrogel. The hydrogel was incubated at a room temperature of 24° C. and the supernatants where exchanged every day for at least three days. All experiments were performed three times. Under none of the tested conditions the KA7-hydrogel could be destroyed. No other known none-covalent heparin-dependent hydrogel possesses such a stability, which emphasizes the extraordinarily stable interaction between the KA7 and heparin. Even the hydrogel on the basis of the very short KA5 was only destroyed by 1 M HCl after more than one week incubation. 2,2,2-trifuourethanlol (TFE) is known to destroy any type of secondary structures. Even though KA7-starPEG-hydrogel with heparin appears indestructible, the structure can be destroyed by adding 2,2,2-trifuourethanol (TFE) to the supernatant. Freeze-drying of this 2,2,2-trifluourethanol (TFE)-, KA7-starPEG- or heparin-solution and the addition of phosphate buffer solution (1×PBS) resulted in a clear gel again.

TABLE 4

| Supernatant | KA7 | KA5 | RA7 |
| --- | --- | --- | --- |
| 1xPBS | Stable | Stable | Stable; the surface of the hydrogel was milky |
| Water | Stable | Stable | Stable |
| 1M HCl | Stable | Stable; hydrogel was destroyed only after one week | Stable; hydrogel was milky and thereafter clear again |
| 1M NaOH | Stable | Stable | Stable |
| Saturated NaCl solution | Stable | Stable | Not stable; hydrogel became milky |
| DMSO | Stable | Stable | Stable |
| Ethanol | Stable | Stable | Stable |
| Cell culture medium | Stable | Stable | Stable |

Three respective different cases were tested in the hydrogel-formation stability test. Table 5 shows the test for forming the hydrogels in different solvents. The hydrogels were formed by mixing the final concentrations of respectively 5 mM peptide-starPEG-conjugate and 5 mM 14-kDa-heparin in 50 µl physiological phosphate buffer solution (1×PBS), Milli-Q-water or cell culture medium with 2% fetal bovine serum (FBS). The stability of the hydrogels was tested with the same solvent in which it was formed in 200 µl supernatant. The hydrogels were incubated at room temperature (24° C.), the supernatants were changed every day for at least three days in a row and the result after at least 3 days analyzed.

TABLE 5

| Peptide-starPEG-conjugate | PBS | water | Cell culture medium |
| --- | --- | --- | --- |
| KA7 | formed | formed | formed |
| KA5 | formed | Formed | formed |
| RA7 | formed | formed | formed |

Cell culture medium with 2% fetal bovine serum (FBS) contains an amount of proteins and other components, which may potentially disrupt the interaction between the (BA)n-peptide-motif and 14-kDa-heparin if this interaction is not stable.

Further, an erosion experiment was conducted. For this purpose peptide-starPEG-conjugates were respectively mixed with TAMRA-marked 14-kDa-heparin. For the erosion experiment the TAMRA-marked 14-kDa-heparin had to be synthesized beforehand. Hereby 14-kDa-heparin was marked with 5-(and-6)-carboxytetramethylrhodamin (TAMRA, Invitrogen) by using the 1-ethyl-3-(3-dimethylaminopropyl)carbodiimide/N-hydroxysulfosuccinimide- (EDAC/sNHS)-chemistry. Heparin, TAMRA, EDAC, sNHS and $Na_2CO_3$ were mixed at a ratio of 1:2:5:4:20 in water and incubated overnight. Thereafter the mixture was dialyzed for two days against 10 liters of water in a dialysis membrane with an exclusion limit of 8 kDa with constant exchange of water. The dialyzed product was filtered through a 0.22 µm polyvinylidene fluoride filter (PVDF-filter) and freeze-dried to a red product.

Subsequently the peptide-starPEG-conjugates were respectively mixed with the TAMRA-labelled 14-kDa-heaprin in 50 µl cell culture medium to a final concentration of 5 mM. The hydrogels were formed at 37° C. at 95% humidity and 5% $CO_2$ overnight (15 hours) (Galaxy 170S, Eppendorf, Hamburg Germany). After an incubation overnight, 1 ml of the cell culture medium with 2% fetal bovine serum (FBS) was added. 200 µl of the supernatant was removed at each measuring time point and replaced with new cell culture medium with 2% fetal bovine serum (FBS). The fluorescence was measured at defined time points in the supernatant by using a plate reading device (BECKMAN COULTER PARADIGM Detection platform, BECKAMN COULTER, Brea, Calif., USA) and black 96-well-plates with clear bottom.

Figure 8A:
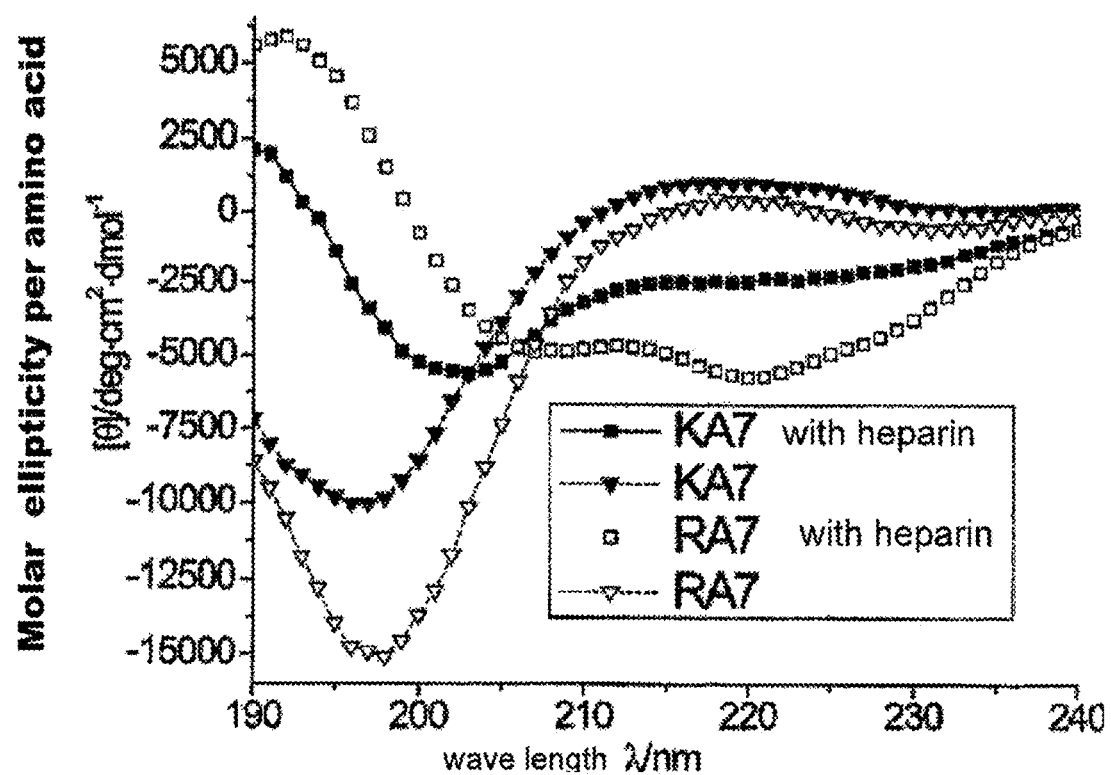
FIG. 8A shows the analysis of a heparin dependent structural change through circular dichroism-spectroscopy.
Figure 8B:
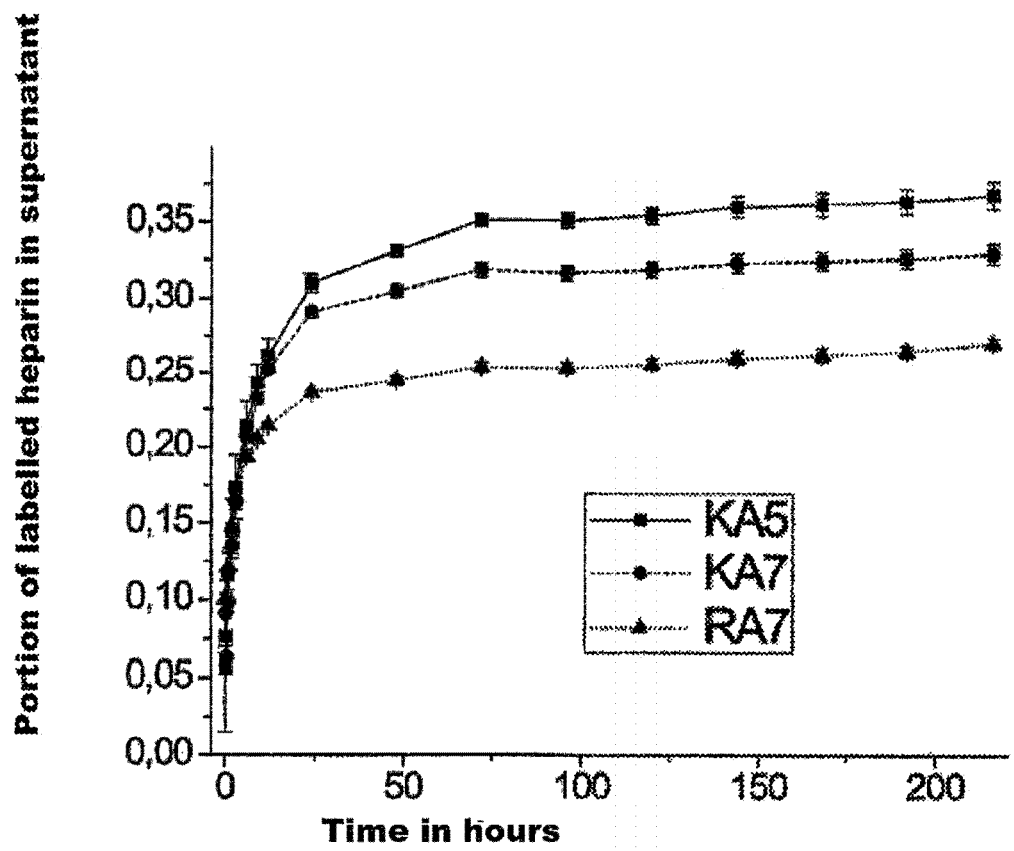
FIG. 8B shows the result of investigating the erosion of the hydrogel through mixing together of peptide-starPEG conjugate with a TAMRA labeled 14-kDa heparin.

FIG. 8A shows the analysis of a heparin dependent structural change by circular dichroism spectroscopy. Both peptides shoed without heparin a random coiled structure in Milli-Q-water. After addition of 14-kDa-heparin in a 2 molar concentration of the peptides a clear structural change occurred. FIG. 8B shows the result of the testing of the erosion of the hydrogel by the above-mentioned admixture of peptide-starPEG-conjugate and TAMRA-marked 14-kD-heparin in 50 µl cell culture medium with 2% fetal bovine serum (FBS) to a final concentration of 5 mM. The fluorescence was measured in 200 µl of 1 ml supernatant. These 200 µl were each replaced by 200 µl fresh medium.

As is known from the literature, inter alia from J R Fromm, R E Hileman, E B O Caldwell, J M Weiler, R J Linhardt, Archives of Biochemistry and Biophysics 1997, 343, 92-100, arginine binds to heparin stronger than lysine. RA7 is bound stronger to heparin so that less heparin is released from the hydrogel with RA7-starPEG than from the hydrogel with KA7-starPEG. KA5 possesses less charge than KA7, so that the bond is weaker, which leads to more erosion. The hydrogels lost mass to a negligible degree so that it is likely that most of the heparin, which was released, i.e., up to 35%, is not part of the hydrogel network. After the stabilization of the heparin-erosion out of the hydrogel the latter is more stable than protein-hydrogels. The fact that the hydrogel remains very stable against serum and its components shows the specificity of the interaction between the (BA)n-peptide-motif and heparin. Thus the hydrogel does not have to be pre-formed prior to application. This is a very significant advantage because it saves time and the concentration for example of the proteins is evenly distributed. In addition the reproducibility is greater because less production steps are involved.

For a scanning electron microscopic image, KA7-starPEG-conjugates were mixed with 14-kDa-heparin to a final concentration of 5 mM respectively in 50 µl physiological phosphate buffer solution (1×PBS) and incubated at room temperature for three days. The sample was taken by inserting a capillary tube into the gel, shock-freezing in liquid nitrogen and cutting though the sample with a very sharp knife. The surface-dried and cut sample was imaged with a scanning electron microscope (Supra 40VP, Zeiss, Jena, Germany).

Figure 9:
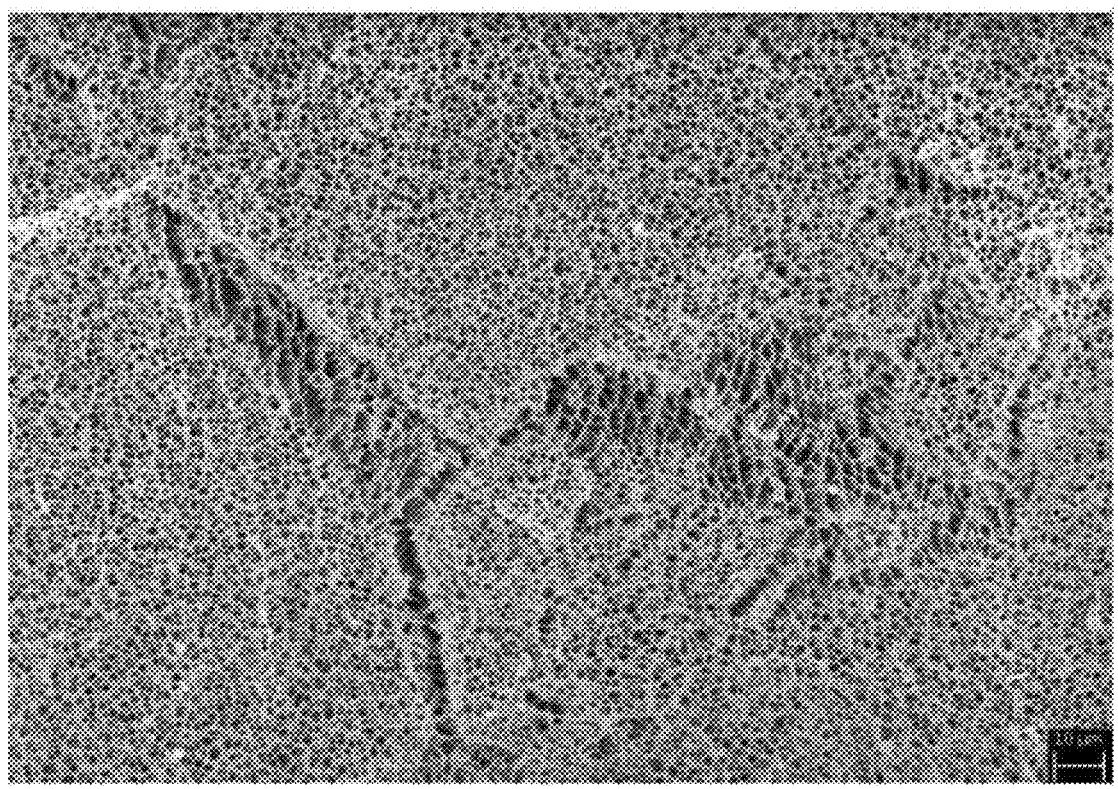
FIG. 9 shows a scanning microscopic image of KA7-starPEG-hydrogel with heparin.

FIG. 9 shows a scanning electron microscopic image of the KA7-starPEG-hydrogel with heparin. The sample was flash frozen in liquid nitrogen and analyzed after a short period of evaporation. The KA7-starPEG-hydrogel showed a clear network structure.

In respect of the hydrogel preparation the gelation time is an important parameter. At the beginning the gelation time was to be determined by using the shear stress controlled rheometer (MCR 301, Paar Physica, Anton Paar, Ashland, Va.) at 20° C. and a measuring unit with 39,979 mm diameter, an angle of 0.305° and a truncation of 24 µm. Disadvantageously the measuring with 2% amplitude and a frequency of 1 Hz changed the gelation time. The gelation occurred much faster than was previously observed in the laboratory. This behavior necessitated a different approach to measure the gelation time. A microchip-controlled machine capable to measure the time dependent hydrogel stiffness on a fine scale (XP 205 Feingewicht Delta Range, Mettler-Toledo GmbH Giessen, Germany) was constructed and programmed.

Figure 10:
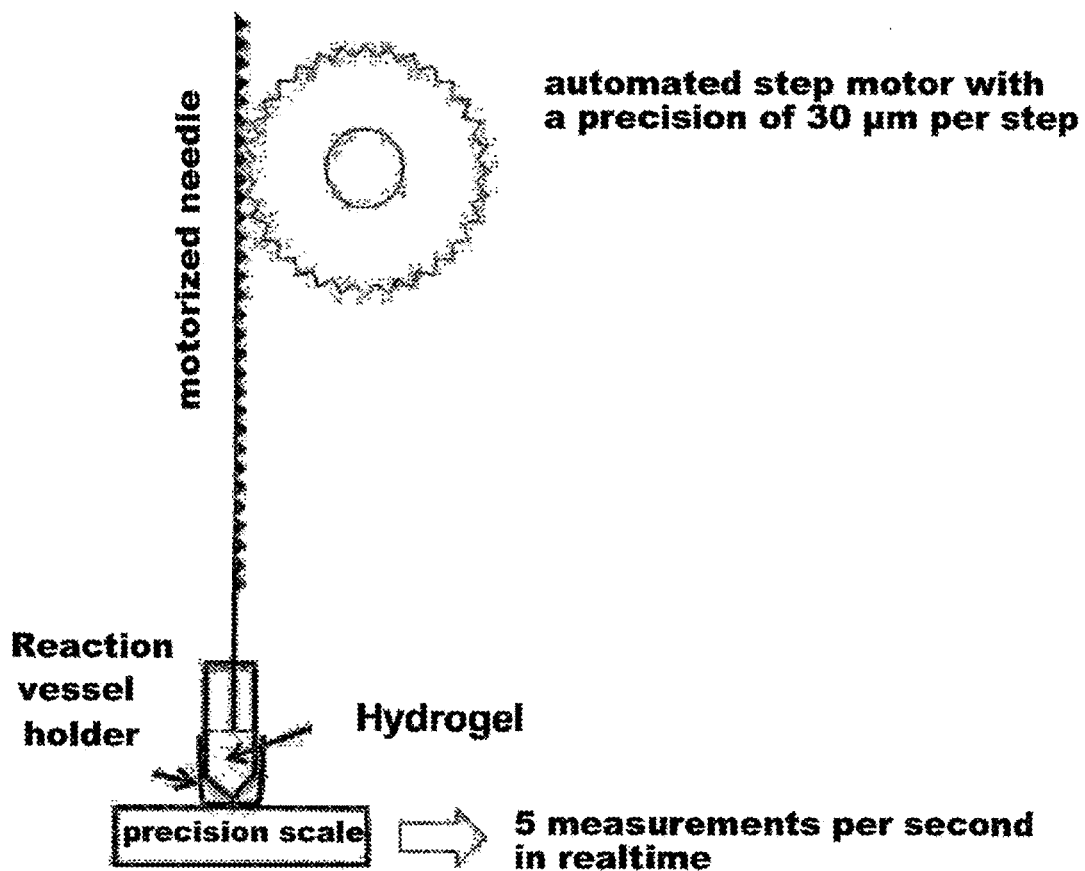
FIG. 10 shows a device for analysis of the gelation time of a hydrogel.

FIG. 10 shows a device for analyzing the gelation time of a hydrogel controlled by a programmable microchip and the use of a precision scale for measuring the gelation time of the hydrogels. Shown is a movable part on the precision scale consisting of a blunt needle and a holder for a 0.2 ml reaction vessel, which contains the hydrogel mixture. LabX-software was used to monitor and record the force.

Different concentrations of peptide-starPEG-conjugates were mixed at constant stirring with 14-kDa-heparin, to form 50 µl hydrogel in phosphate buffer solution (1×PBS) in the 0.2 ml reaction vessel. After the mixing the reaction vessel was closed with a lid having a 1.5 mm hole and the measuring started immediately. On the inside of the lid 10 µl of water protected the hydrogel surface from drying out. At the beginning of the measurement the blunt needle of 1 mm diameter is inserted 1 mm deep into the hydrogel viewed from above. Every 5 minutes the blunt needle moves 1 mm into the gel and after one second waiting time is moved upwards 30 µm below the original position. This 30 µm height difference ensures that the needle does not form a channel in the gel, which would not pose any resistance, but rather each measurement advances deeper and deeper into the gel (straight ahead from above) to always encounter an untouched hydrogel mixture, which can be measured. All data of the precision scale where monitored and documented by using the LabX software (Mettler-Toledo GmbH, Giessen, Germany), which was connected with the precision scale with an RS-232 serial connection. The amplitudes of the resistance of the hydrogel against the pressure after pushing down the needle, corrected by the baseline prior to recording a measuring point, were plotted.

Figure 11A:
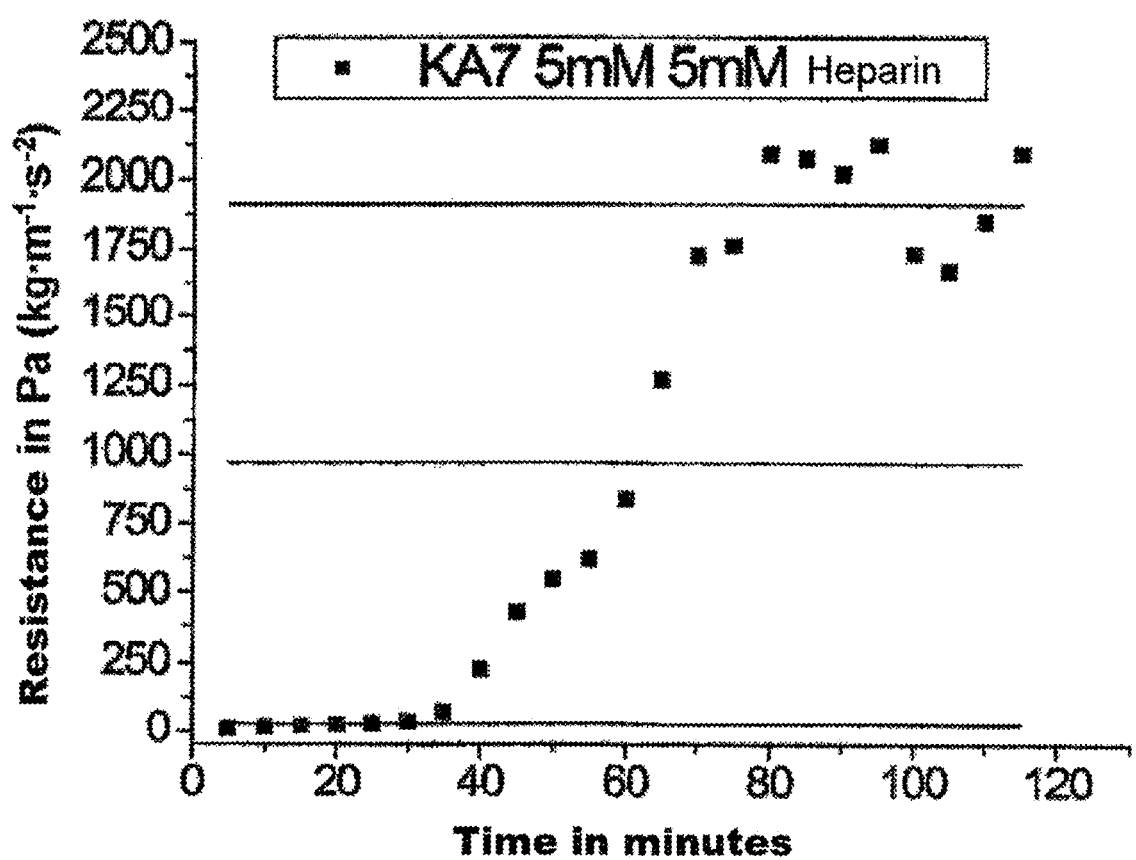
FIGS. 11A-11C show the result of the analysis of the gelation time of a hydrogel with 5 mM KA7 and 5 mM Heparin (FIG. 11A), 2.5 mM KA7 and 0.5 mM Heparin (FIG. 11B) and 5 mM KA5 and 5 mM Heparin (FIG. 11C)
Figure 11B:
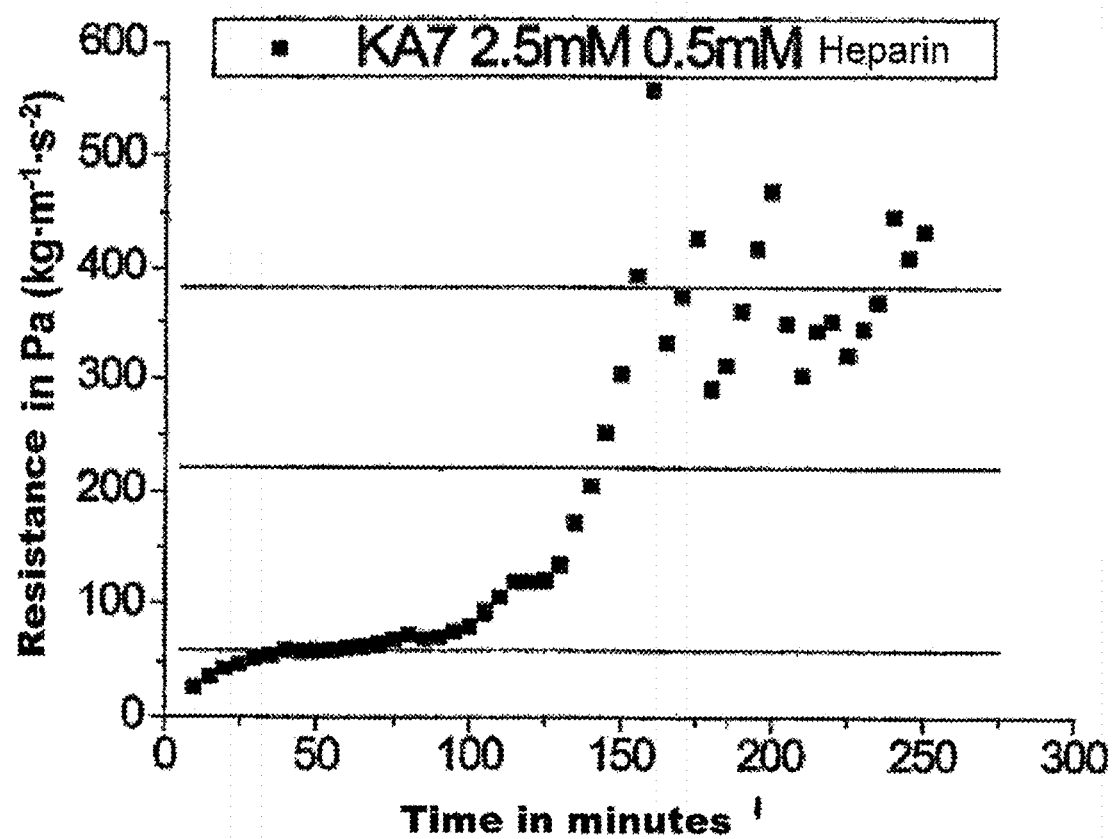
Figure 11C:
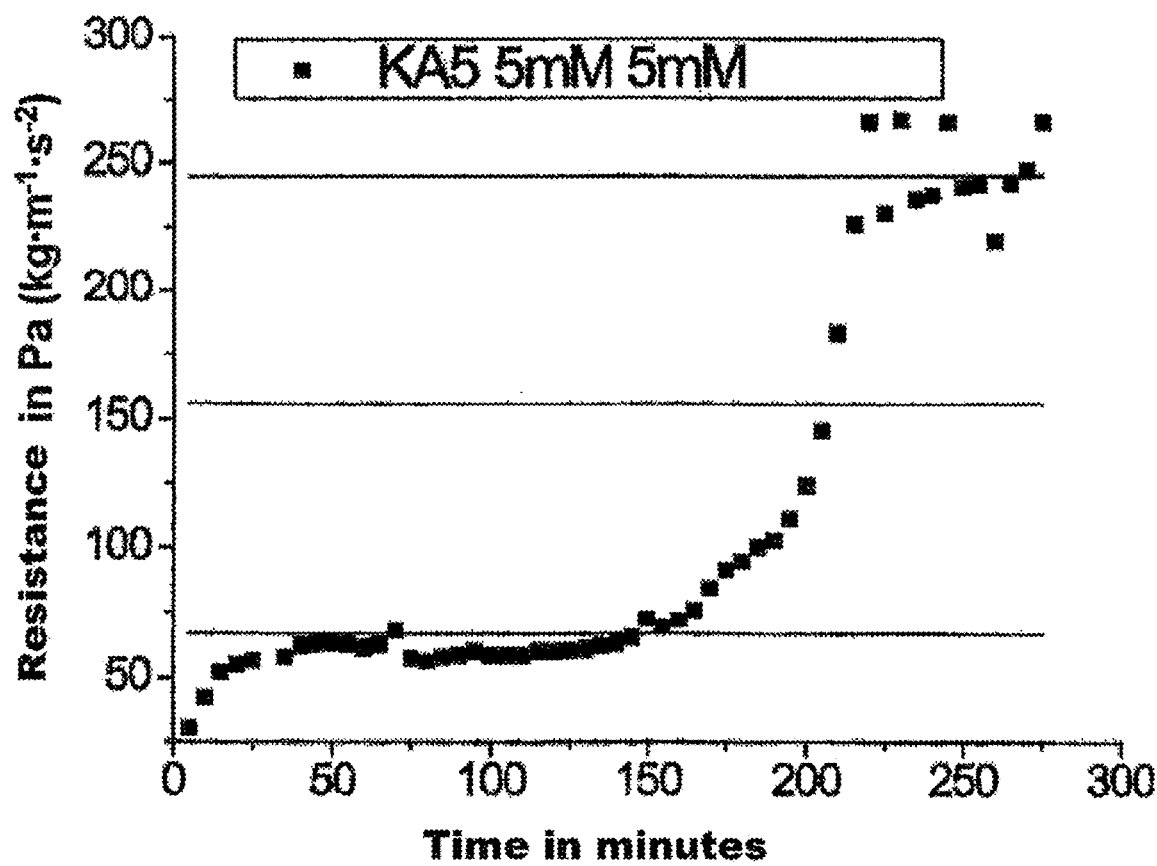
Figure 12A:
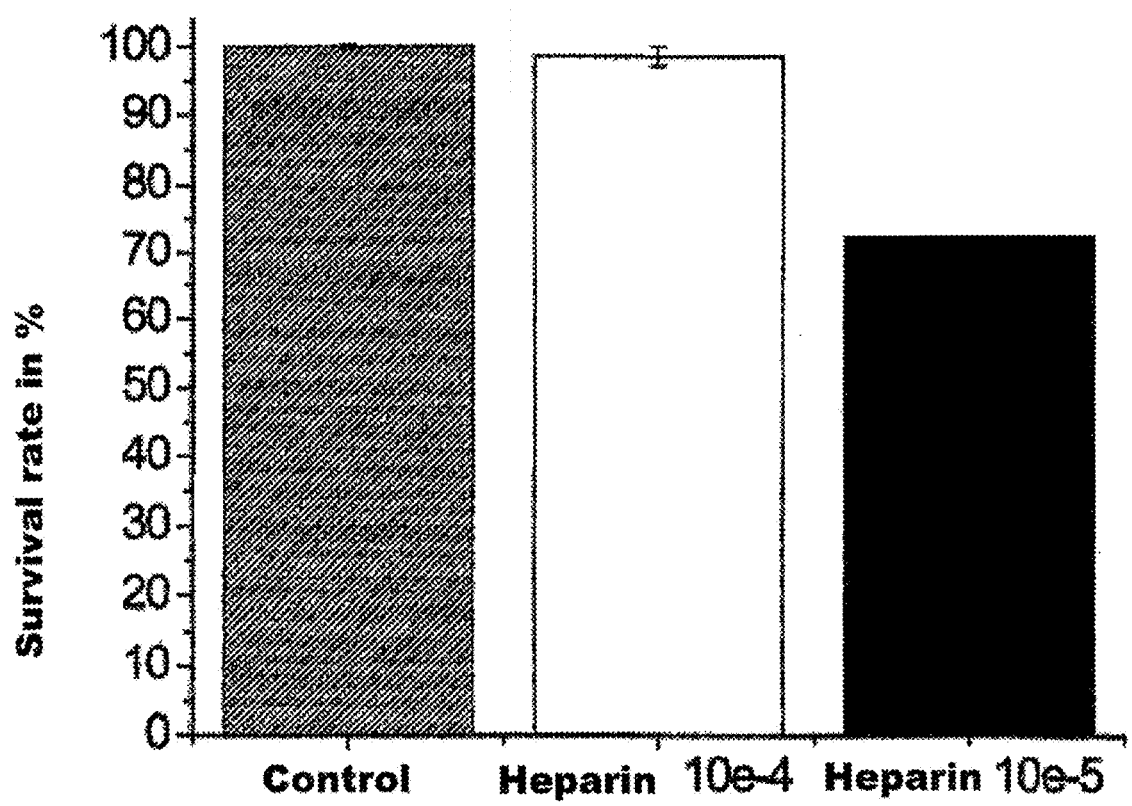
FIGS. 12A-12F show a toxicity test for various peptide-starPEG-conjugates and 14-kDa heparin and human fibroblasts (HDFn): In particular.
Figure 12B:
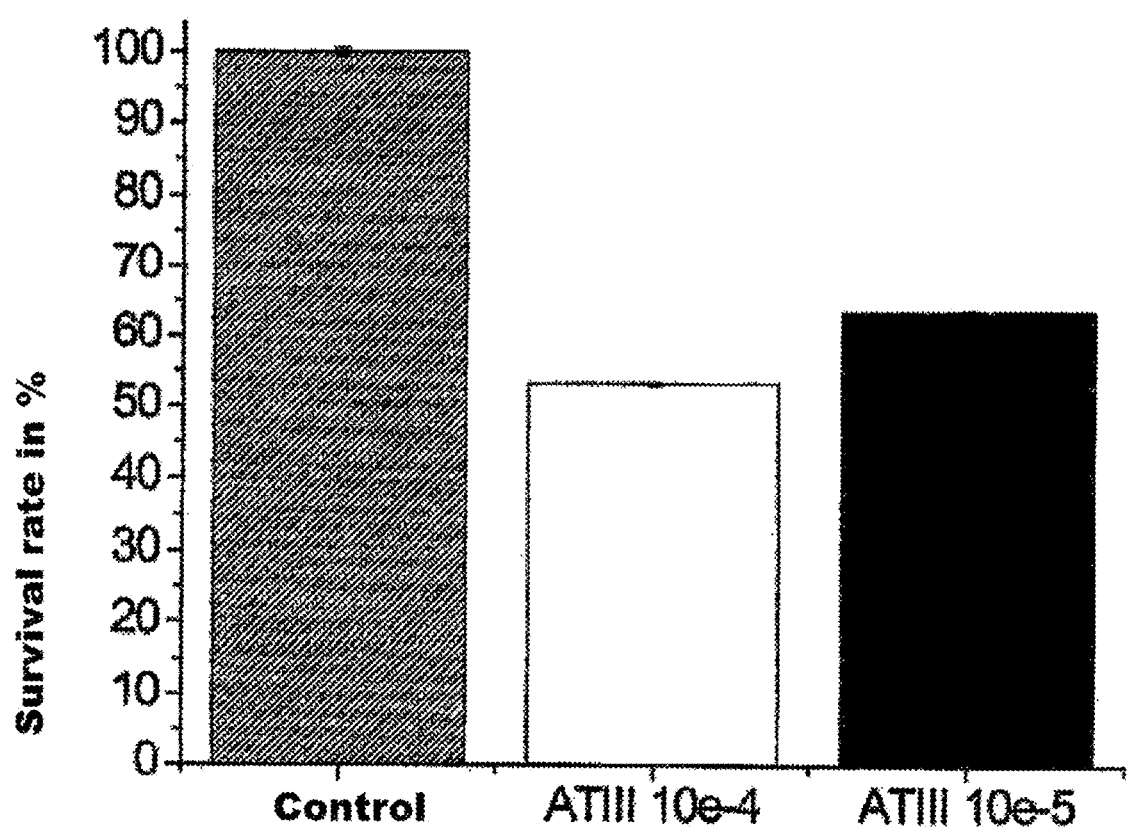
Figure 12C:
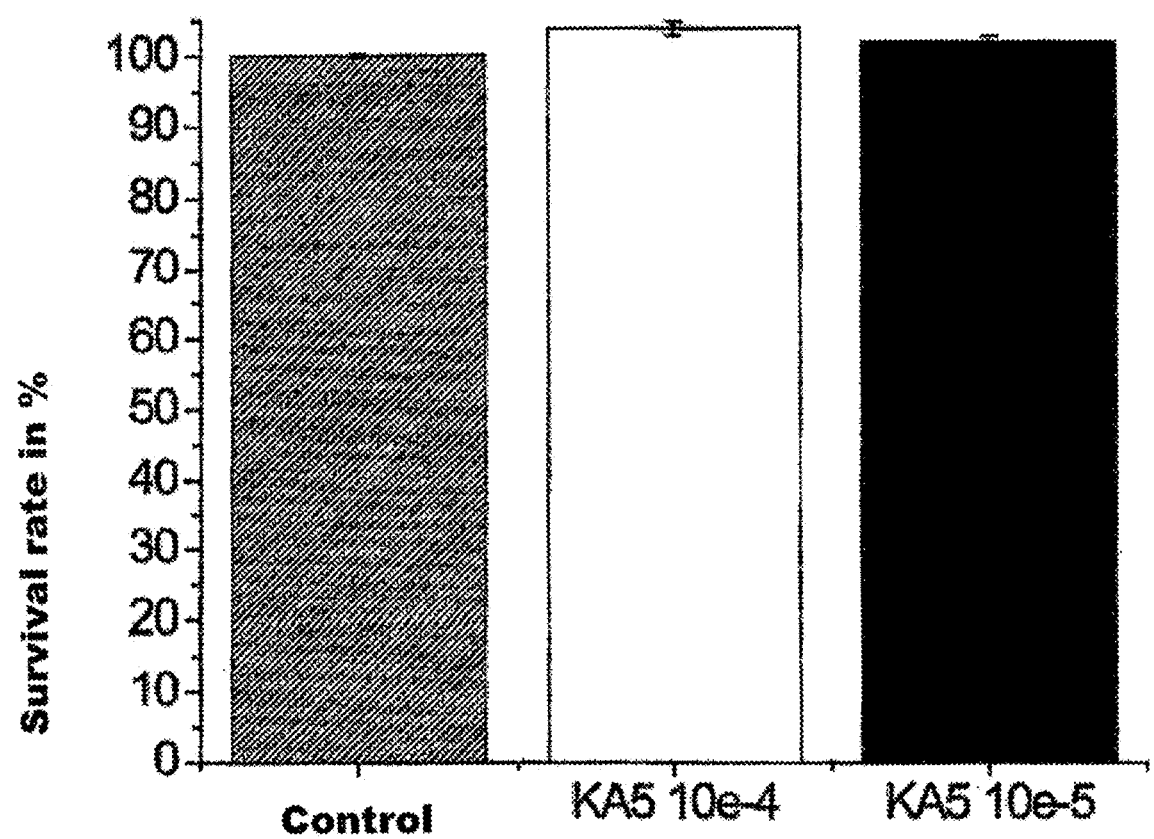
Figure 12D:
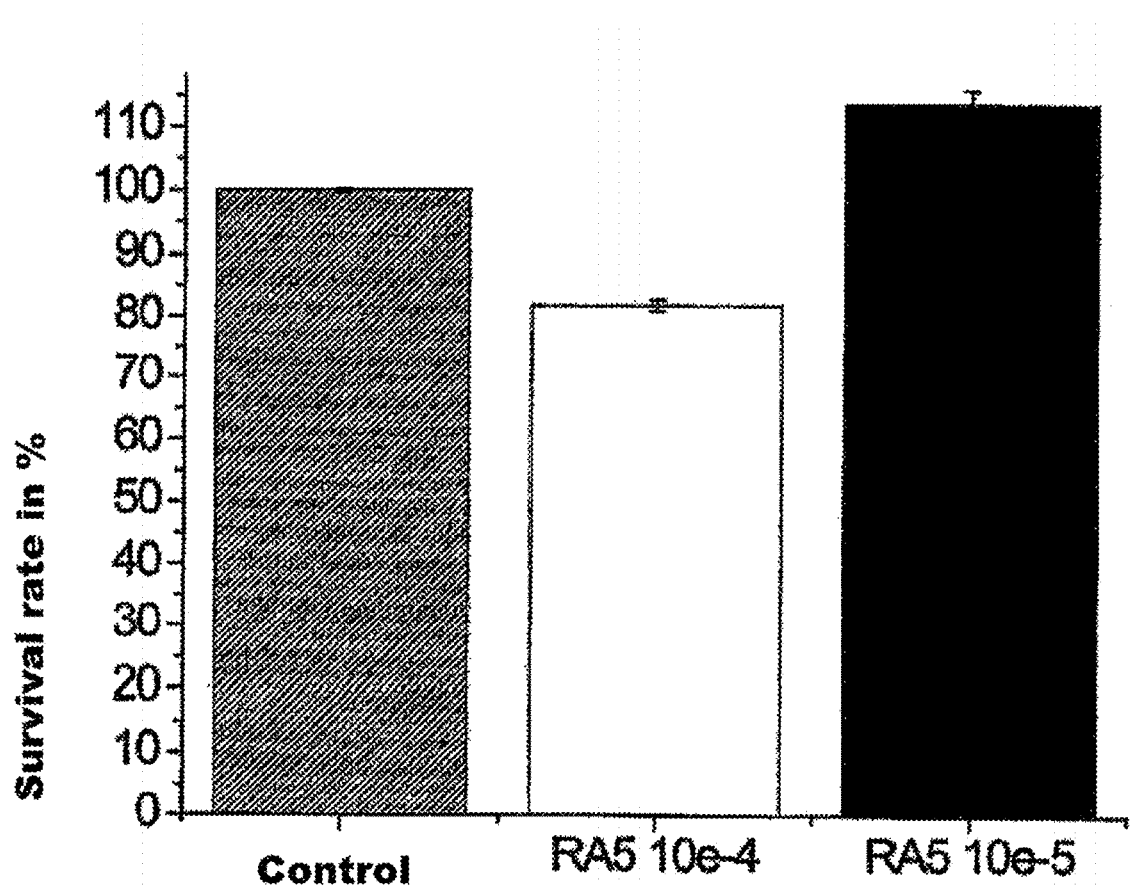
Figure 12E:
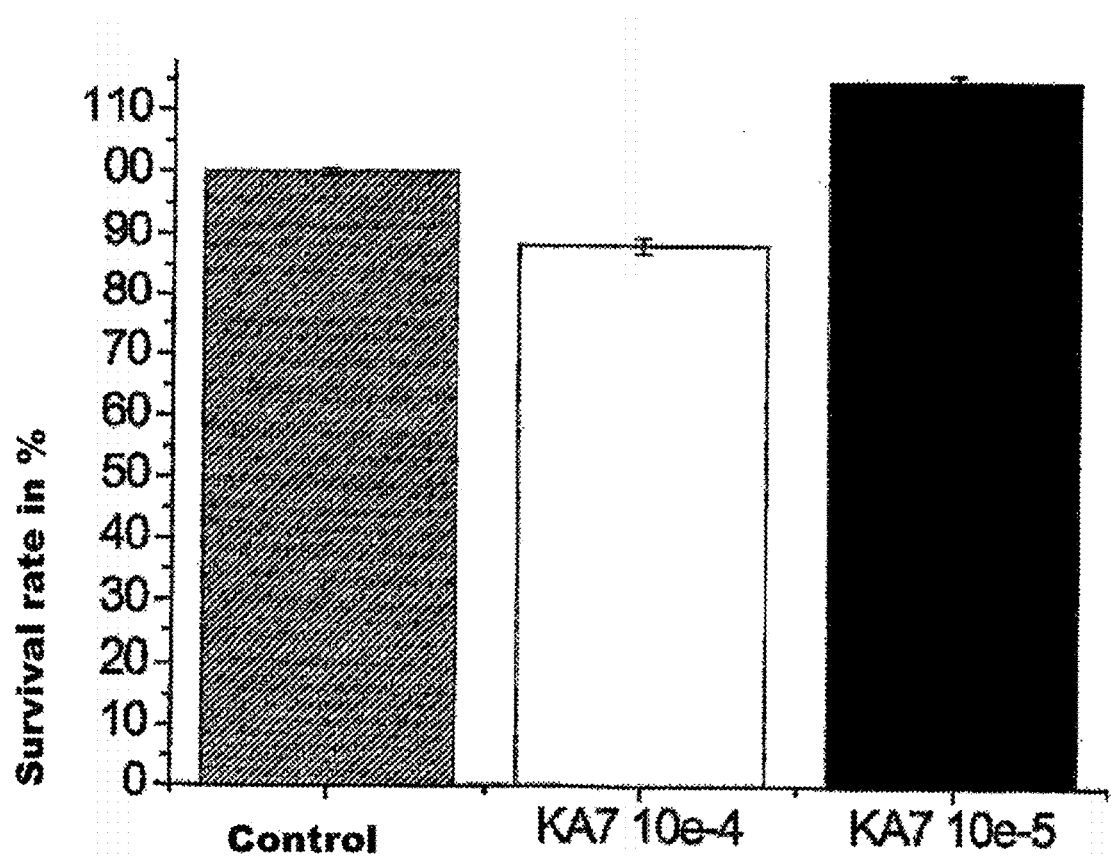
Figure 12F:
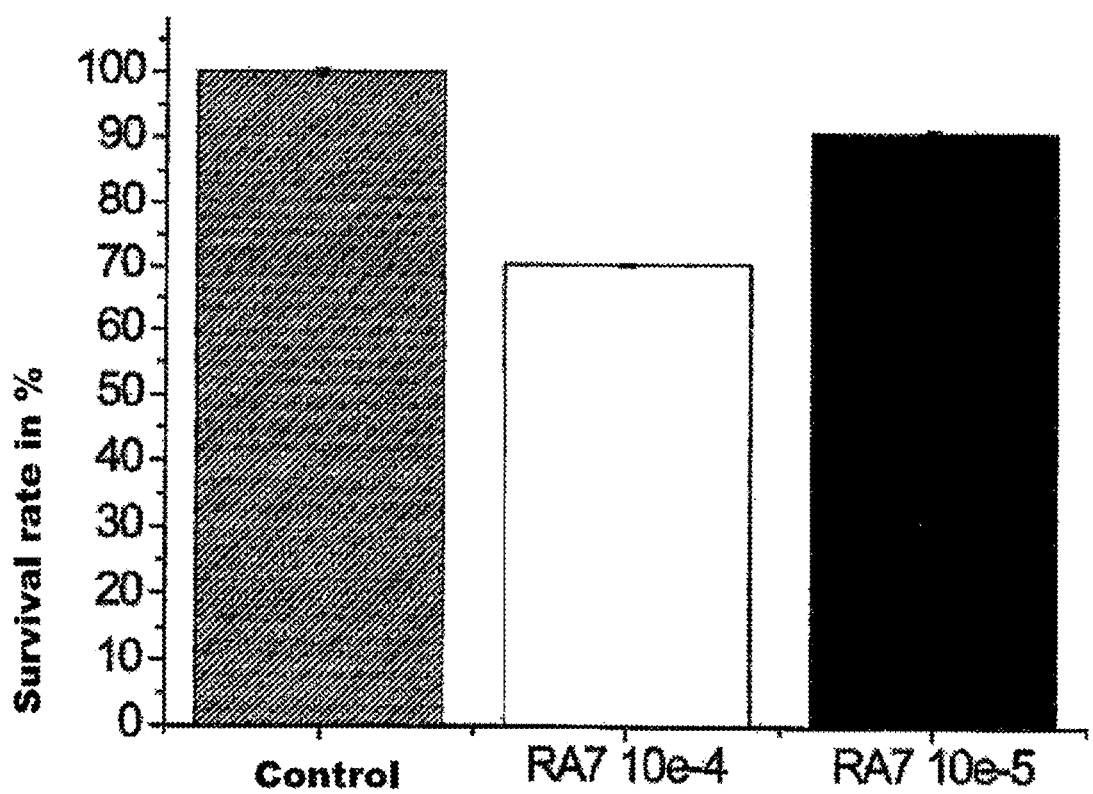

FIGS. 11A to 11C show the result of the analysis of the gelation time of the hydrogel by measuring the force required for inserting a needle with 1 mm diameter. Immediately after the mixing of the components the measurement was performed every 5 minutes. For each measurement the needle was moved downwards in the mixture by 1 mm and upwards by 0.970 mm. The force was measured by weighing and the amplitude, corrected by the baseline, was plotted.

Due to the different charge properties of RA7-starPEG, KA7-starPEG and KA5-starPEG the gelation time differs. RA7-starPEG-hydrogel forms with 14-kDa-heparin in phosphate buffer (1×PBS) immediately with a final concentration of 5 mM. KA7-starPEG requires about one hour for the formation of the hydrogel under the same conditions and KA5-starPEG several hours. By lowering the concentration of the components, the gelation time increases as a comparison of FIGS. 11A and 11B shows. The mixing of different (BA)n-peptide motifs, which are coupled to starPEG would make it possible to adjust stiffness and gelation time together. This provides a system for the user, with which the gelation time can be adjusted by changing the concentration of the components or the ratio of the different starPEG coupled (BA)n-peptide motifs while retaining the solids content.

The hydrogel consisting of the (BA)n-starPEG-conjugates with heparin is not toxic to mammalian cells shown by an in vitro cytotoxicity test of the hydrogel components (see FIGS. 12A to 12F). Fibroblasts were successfully cultured embedded for a 9 days in hydrogels made of KA7-starPEG or KA5-starPEG with heparin in cell culture medium with 2% fetal bovine serum (FBS).

A frozen vial with cells was thawed in a 37° C. water bath for 2 minutes. The cells were transferred into 5 ml complete cell culture medium 106 (with 2% fetal bovine serum (FBS)). This cell suspension was centrifuged at 700 g in a centrifuge (ROTINA 380 R, Hettich, Tuttlingen, Germany), the supernatant removed and the cells resuspended in 6 ml complete cell culture medium. After the mixing the suspension was transferred into a cell culture container and incubated at 37° C., 95% humidity and 5% $CO_2$. After 2 days the medium was changed until the cells were confluent. The cell culture medium of the confluent phase of the cells was removed and 1 ml trypsin/EDTA solution was added to the cell layer. After 5 minutes and occasional shaking the cells are in suspension and 3 ml of the new culture medium was added. This 4 ml of the cell suspension were centrifuged at 700 g in a centrifuge (ROTINA 380 R, Hettich, Tuttlingen, Germany) the supernatant removed and the cells suspended in an amount of complete cell culture medium to obtain the target concentration. The tests for toxicity of the peptide-starPEG-conjugates were performed by inoculating 5000 HDFn cells per well in a 96 well plate. After the transfer of the cells they were able to attach to the 96 well plates. The cells were incubated 24 hours prior to administering the samples at 37° C., 5% $CO_2$ and 95% humidity.

FIGS. 12A to 12F show a toxicity test for different peptide-starPEG-conjugates and 14-kDa-heparin. The cell medium was replaced after the 24 hours incubation by 200 µl of a solution containing fresh medium and $10^{-4}$ or $10^{-5}$ M peptide-starPEG-conjugate, which was filtered through 0.22 µm centrifuge tube filters. Thus $10^{-4}$ and $10^{-5}$ M peptide-starPEG-conjugate or heparin was added to the 5000 resuspended human fibroblasts in cell culture medium with serum. After the addition of the entire test samples the cells were incubated for 24 hours at 37° C., 5% $CO^2$ and 95% humidity in order to analyze the time-dependent and also the concentration-dependent cytotoxicity. At the end of each exposure the toxicity level of each test sample was evaluated by a test with 3-(4,5 dimethylazol-2-yl)-2,5-diphenyltetrazoliumbromide (MTT) in order to determine the cytotoxicity of the peptide-starPEG-conjugates compared to non-treated cells. Treatment control was done by addition of media instead of the MTT compound.

The MTT test enables judging the viability of the cells by measuring the enzymatic reduction of yellow tetrazolium to violet formazan. After incubation of the cells with the test solutions MTT was added and incubated for a further 4 hours. After 4 hours the medium was removed and 100 µl of dimethylsulfoxide (DMSO) was added. The absorption of the solubilized formazan crystals was measured at 570 nm by using a plate reader (BECKMAN COULTER PARAGIDM Detection platform, BECKMAN COULTER, Brea, Calif., USA). Because the absorption directly indicates the number of viable cells, the percentage of viability was calculated directly from the absorption values. The average toxicity was calculated by the mean value of 15 wells of the cells, which were treated with the same compound.

FIGS. 12A to 12F show the results of the MTT tests for A) 14-kDa-heparin B) ATIII-starPEG-conjugate, C) KA5-starPEG-conjugate, D) RA5-starPEG-conjugate, E) KA7-starPEG-conjugate and F) RA7-starPEG-conjugate.

For embedding of cells in the hydrogel the cell medium was first removed from the confluent layer of the cells and then 1 ml trypsin/EDTA solution added to the cell layer. After 5 minutes and occasional shaking the cells are in suspension, whereupon 3 ml of new cell culture medium were added. The amount of cells was counted by mixing of 50 µl of the cell suspension with 50 µl of trypan blue solution, wherein the cells were counted by using a hemocytometer. The 4 ml of cell suspension were centrifuged at 700 g in a centrifuge (ROTINA 380 R, Hettich, Tuttlingen, Germany) the supernatant removed and the cells resuspended in an amount of complete cell culture medium to obtain the target concentration. KA7-starPEG-conjugates were dissolved in the entire cell culture medium and filtered through a 0.22 µm centrifuge tube filter. The same was performed with 14-kDa-heparin. To the solution of KA7-starPEG-conjugate cells were correspondingly added to obtain a final concentration of $10^6$ cells per ml. Thereafter the KA7-starPEG-conjugat-cell-mixture was mixed with 14-kDa-heparin to a final concentration of 5 mM of both in 50 µl, pipetted onto the bottom of an 8-well-plate and incubated overnight at 37° C., 95% humidity and 5% $CO_2$. After 1 day, 0.5 ml of the entire cell culture medium was added (and changed every 2 days) and the cells were further incubated at 37° C., 95% humidity and 5% $CO_2$. The embedding of the cells in the KA5-starPEG-conjugate-mixture with 14-kDa-heaprin was performed in the same manner as in the case of the KA7-starPEG-conjugate and similar results were obtained.

The viability of the cells was determined by addition of 50 µl MTT 3-(4,5-dimethylazol-2-yl)-2,5-diphenyltetrazoliumbromide) into the 500 µl of the complete cell culture medium, as supernatant of the cells embedded in the hydrogel. The cells were imaged after 1 hour of incubation with a dissection microscope.

The viability of the cells was examined with a so-called Live/Dead® Assay. The cells-containing gels were rinsed twice with phosphate buffer solution (1×PBS). A solution of 10 µM propidium iodide (PI) (Molecular probes, Invitrogen, Germany) and 0.15 µM fluorescein diacetate (FDA) (Fluka, Germany) in phosphate buffer solution (1×PBS) were applied for three minutes onto the gels, followed by rinsing with 1×PBS. The cells were imaged with a confocal microscope (Leica SP5, 10×/04). The images were recorded for a gel section of 100 µm thickness and the maximum intensity projection (MIP) of the images shown.

Prior to the immuno-staining the samples were fixed with 4% paraformaldehyde (PFA) for 15 minutes at room temperature and blocked in 0.25% bovine serum albumin (BSA) (Sigma-Aldrich, Munich, Germany) and 1% Triton-X100 (Sigma-Aldrich, Munich Germany) in PBS). Next Phalloidin-CF488 (Biotrend, Germany) was applied in blocking buffer for 5 min. Thereafter 0.1 µg/ml 4',6-diamidino-2-phenylindol (DAPI, Sigma-Aldrich, Munich, Germany) was applied in 1×PBS for 5 min, followed by 3×15 min of washing with buffer. The samples were imaged with a confocal microscope (Leica SP5, 63×/1.4-0.6).

Figures 13A, 13B, 13C, 13D, 13E, 13F:
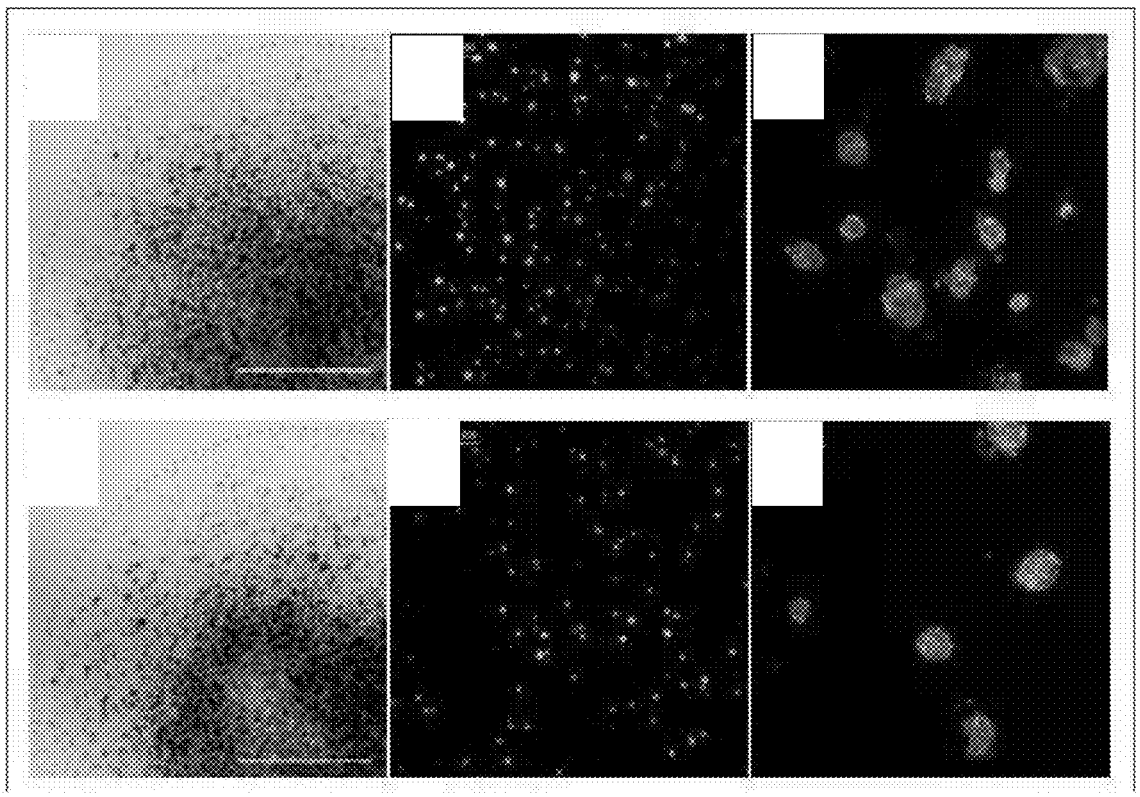
FIGS. 13A-13F show the results of a viability test and the structure of embedded human fibroblasts (HDFn) within a hydrogel. The final mixture in complete cell culture medium contains 5 mM KA5-starPEG-conjugate and 14-kDa-heparin for FIGS. 13A, 13B and 13C; and 2.5 mM KA7-starPEG-conjugate and 14-kDa-heparin for FIGS. 13D and 13F.

FIG. 13 shows in A) to F) the results of the viability test and the structure of the human fibroblasts (HDFn) from the skin of newborns in a hydrogel. The final mixture in complete cell culture medium contains 5 mM KA5-starPEG-conjugate and 14-kDa-heparin for the parts A) to C) and 2.5 mM KA7-starPEG-conjugate and 14-kDa-heparin for the parts D) and F) of FIG. 13. The concentration of the cells was $10^6$ cells per ml. The parts A) and D) of FIG. 13 show wide-field microscopic images, scale 1 mM, of HDFn stained with 3-(4,5-dimethylthiazol-2-yl)-2,5-diphenyltetrazoliumbromide) (MTT) in the hydrogel. The parts B) and E) of FIG. 13 show Live/Dead® Assay stained HDFn. Part B) of FIG. 13 shows a proportion of live cells of 99±1%. The parts C) and F) of FIG. 13 show actin filaments and the nucleus of HDFn stained with pholloidin-CF488 and DAPI. The parts B) and C) and also the parts E) and F) of FIG. 13 show microscopic confocal laser scanning images.

Comparison of Gel Formation by Using Modifications of the Peptide, Different Negatively Charged Oligosaccharides and Variations of the PEG Molecule Different components of KA7-PEG and oligosaccharides are compared for their ability to form a non-covalent hydrogel. The following parameters have been varied and compared: PEG polymers (linear and 4-arm star-shaped), size of PEG polymer (10 and 40 kDa), influence of additional peptide sequence insertions (KA7-RGDSP versus KA7), linear oligosaccharide (heparin and dextran sulfate) and cyclic oligosaccharides (α-cyclodextrin sulfate, β-cyclodextrin sulfate, γ-cyclodextrin sulfate).

TABLE 6

Peptides used.

| Peptide name | Peptide sequence | SEQ ID NO: |
|---|---|---|
| KA7 | CWGGKAKAKAKAKAKAKA | 5 |
| KA7-RGDSP | CWGGRGDSPGGKAKAKAKAKAKAKA | 26 |

Coupling of PEG and Peptide

The cysteine-terminated peptides were conjugated to maleimide-terminated PEG (all supplied from Jenkem) by Michael addition reaction. The required amounts were weighed out on a balance (balance Excellence Plus XP205

Delta Range, Mettler Toledo) and stored in suitable reaction tubes (Safe-Lock Tubes, Eppendorf). For this reaction 4-arm starPEG and linear PEG (for the used sizes see Table 7) were dissolved in Acetonitrile (VWR) and the peptide was dissolved in phosphate buffered saline (PBS, pH 7.4, Life Technologies). The dissolved PEG was added to the peptide and mixed overnight. Then the conjugated peptide-starPEG was purified by dialysis with a 3.5 kDa cut-off dialysis membrane (dialysis membrane MWCO 3,500; VWR) and deionized water. Whereas linearPEG was purified on a preparative high pressure liquid chromatography (HPLC; ProStar, Aligent Technologies) via reverse phase HPLC with a preparative C18 column and an isocratic gradient. The purified peptide-PEG (for library see Table 8) was flash frozen in liquid nitrogen (VWR) dried on the lyophilizer and stored air-tight at 4° C.

TABLE 7

PEGs for coupling: commercial and short names and sizes.

| Commercial PEG name | Abbreviation for PEG | Sizes |
|---|---|---|
| 4arm-PEG-Maleimide | starPEG | 10 kDa, 40 kDa |
| Maleimide-PEG-Maleimide | linearPEG | 10 kDa |

TABLE 8

Synthesized peptide-PEG conjugates and their molecular weight.

| Peptide-PEG | Molecular weight in Da |
|---|---|
| KA7-starPEG | 17,264 |
| KA7-RGDSP-starPEG(10 kDa) | 19,768 |
| KA7-RGDSP-starPEG(40 kDa) | 49,768 |
| KA7-RGDSP-linearPEG(10 kDa) | 14,884 |

Hydrogel Formation and Rheological Measurements

The oligosaccharides were purchased as given in Table 9 and weighed out as required prior each experiment. Oligosaccharides and peptide-starPEG conjugates were dissolved in PBS (oligosaccharides at five-fold and peptide-starPEG at 1.25-fold of the final concentration) and mixed thoroughly. The samples were applied directly onto the measuring system. First, 80% of the final sample volume was provided by the peptide-starPEG solution. Second, the oligosaccharide solution was added to complete to 100% of sample volume.

TABLE 9

Oligosaccharides used in this report to create a noncovalent hydrogel.

| Oligosaccharide | Abbreviation for the oligosaccharide | Molecular weight in Da | Sulfation degree |
|---|---|---|---|
| Dextran sulfate sodium salt | 5DexS | 5,000 | |
| Dextran sulfate sodium salt | 500DexS | 500,000 | |
| Heparin | Hep | 14,000 | |
| α-cyclodextrin sulfated sodium salt | α-cyclodextrin | 2095 | 10-12 |
| β-cyclodextrin sulfated sodium salt | β-cyclodextrin | 2461 | 12-14 |
| γ-cyclodextrin sulfated sodium salt | γ-cyclodextrin | 2726 | 13-16 |

The Modular Compact Rheometer MCR 302 (Anton Paar) was used with temperature control unit (P-PTD200+ H-PTD200, Anton Paar) and cone-plate measuring system (CP20-0.3 and INSET I-PP20/SS, Anton Paar) for assessment of the mechanical properties of the hydrogels of different composition. The gelation measurement was performed at 20° C. with 1% oscillatory shear strain and a frequency of 1 Hz every 5 min for 2 hours. The data was analyzed with Excel (Excel 2013, Microsoft).

Results

Figure 14:
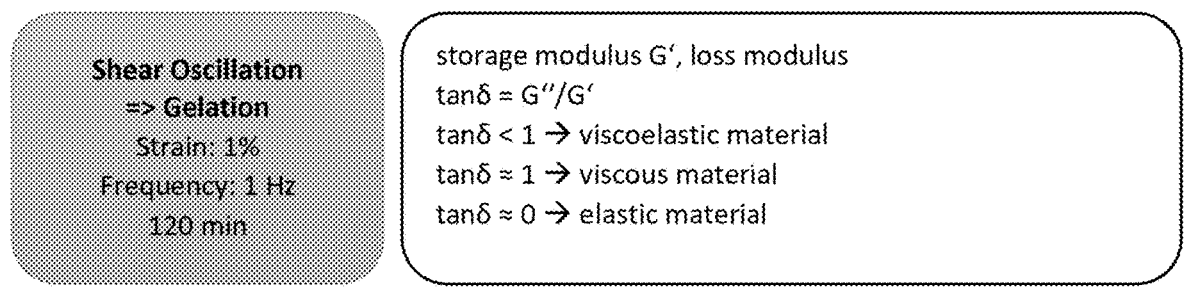
FIG. 14 shows a chart of the mechanical properties received from a shear oscillation measurement.

The following experiments studied the mechanical properties of hydrogels formed of different components. FIG. 14 summarizes the chosen parameters and measurement values. The storage modulus G' and loss modulus G" are calculated from the complex modulus G, which is recorded by the oscillating rheometer. The loss factor tan δ is further calculated by G" divided by G'.

Comparison of starPEG Conjugated with Different Peptide

Figure 15:
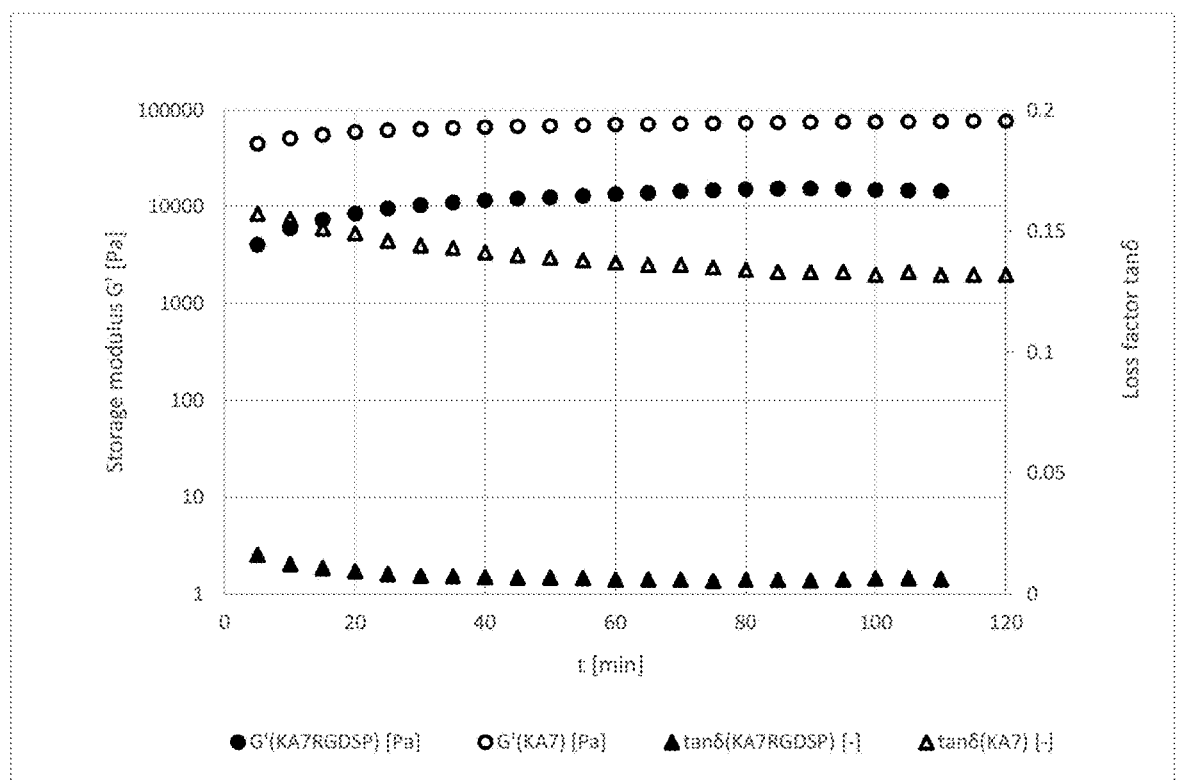
FIG. 15 shows the results of the Gelation measurement of KA7-RGDSP-starPEG and KA7-starPEG with 5 kD dextran sulfate.

The insertion of peptide sequences in addition the linker peptide could impact the gelation process. Hence, the gelation was compared using 2 mM KA7-RGDSP-starPEG and 2 mM KA7-RGDSP-starPEG, which was gelled with 2 mM 5DexS. FIG. 15 presents the storage modulus G' and the loss factor tan δ of the gelation measurement. Details are provided by Table 10.

The measurement curves of G' and tan δ show similar shape and provided proof for gel formation in both groups as indicated by tan δ<0.2. The lower storage modulus G' of KA7-RGDSP-starPEG indicate a softer gel than the one formed by KA7-starPEG. The low tan δ values of KA7-RGDSP-starPEG represents a domination of elastic properties. It can be concluded that the inserted RGDSP (SEQ ID NO: 27) sequence influences the gel properties by making it softer and more elastic. In both conditions tested, hydrogel formation is occurring.

TABLE 10

Parameters and results of KA7 versus RGD-KA7 conjugate.

| Parameter | RGDSP-KA7 | KA7 |
|---|---|---|
| Peptide-starPEG | 2 mM KA7-RGDSP-starPEG | 2 mM KA7-starPEG |
| Oligosaccharide | 2 mM 5DexS | 2 mM 5DexS |
| End point $t_e$ [min] of measurement | 110 | 120 |
| Storage modulus G' [Pa] at $t_e$ | 14,486 | 76,977 |
| Loss Factor [—] at $t_e$ | 0.00611 | 0.132 |

LinearPEG Versus starPEG

Figure 16:
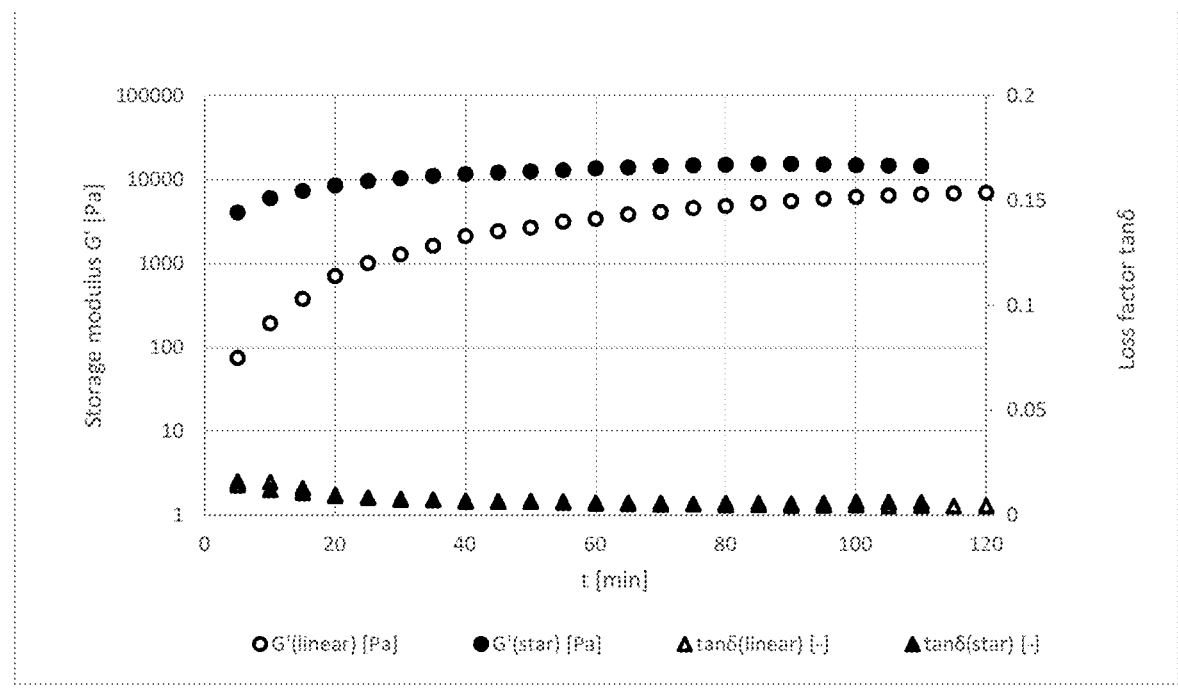
FIG. 16 shows the results of the gelation measurement of linearPEG-RGDSP-KA7 and KA7-RGDSP-starPEG with 5 kD dextran sulfate.

Next, linearPEG and starPEG were directly compared for their hydrogel formation properties. The linearPEG polymers was applied at 10 kDa and conjugated to KA7 linker peptide with RGDSP peptide insertion. For comparison reason, data for KA7-RGDSP-starPEG of FIG. 2 were re-plotted. The results of the gelation measurement are given by FIG. 16. Details are provided by Table 11.

The calculated loss factor tan δ is nearly identical throughout the measurement. The storage moduli G' showed different time points of equilibrium. The linearPEG needs longer to reach a plateau than the starPEG indicating slower gel formation. Nevertheless, both compositions formed hydrogel as indicated by the low loss factors tan δ.

TABLE 11

Parameters and results of linearPEG versus starPEG conjugate.

| Parameter | linearPEG | starPEG |
|---|---|---|
| Peptide-PEG | 2 mM KA7-RGDSP-linearPEG | 2 mM KA7-RGDSP-starPEG |
| Oligosaccharide | 2 mM 5DexS | 2 mM 5DexS |
| End point $t_e$ [min] of measurement | 120 | 110 |
| Storage modulus G' [Pa] at $t_e$ | 6,951 | 14,486 |
| Loss Factor [—] at $t_e$ | 0.00439 | 0.00611 | starPEG 10 kDa Versus 40 kDa

Figure 17:
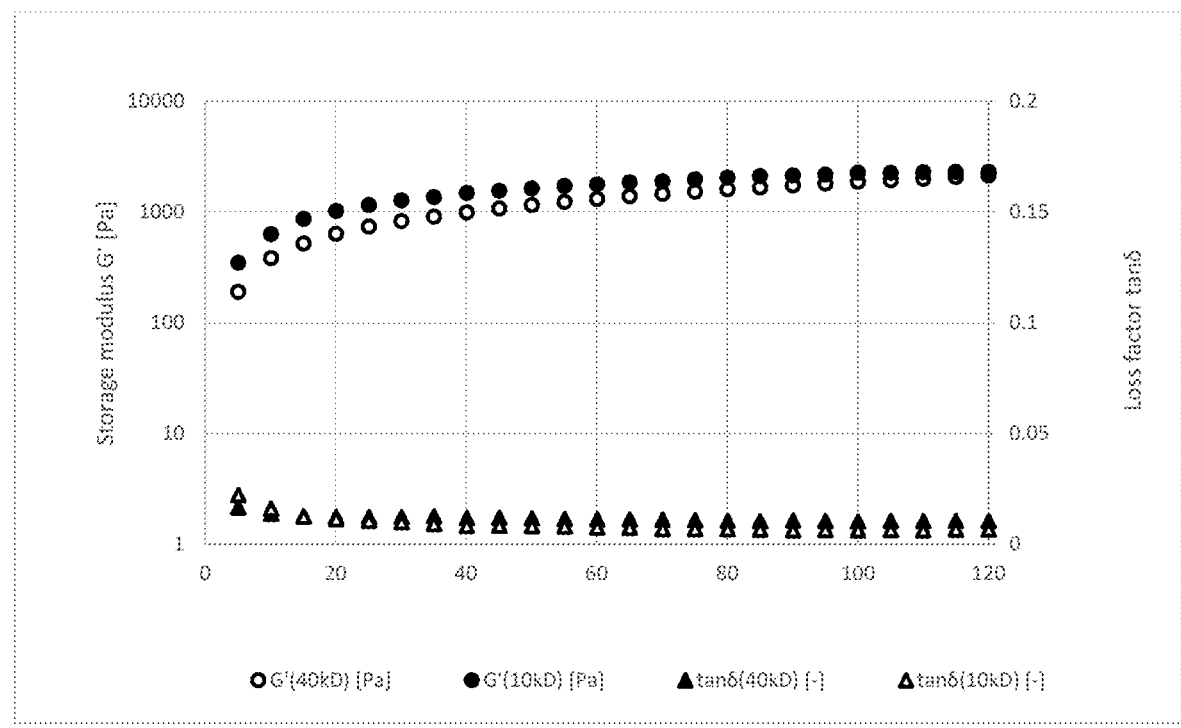
FIG. 17 shows the results of the gelation measurement of starPEG with a molecular size of 10 kDa and 40 kDa brought into reaction with dextran sulfate.

The molecular size of the PEG polymer is another potential influencing parameter to be considered. Two starPEG polymers of different weight, 10 and 40 kDa, were selected as representative candidates, conjugated to RGDSP-KA7 and brought into reaction with 5DexS. Results of the gelation measurements are given in FIG. 17 and Table 12.

StarPEG molecules of 10 and 40 kDa gave very similar curves for the storage modulus and loss factor with similar values for G' and tan δ at the $t_e$. The loss factor tan δ was lower than 0.2 for both curves indication proper hydrogel formation. These results show that the gel formation is not dependent on the size of the PEG polymer.

TABLE 12

Parameters and results of 10 kDa starPEG versus 40 kDa starPEG.

| Parameter | 10 kD | 40 kD |
|---|---|---|
| Peptide-starPEG | 1 mM KA7-RGDSP-starPEG (10 kDa) | 1 mM KA7-RGDSP-starPEG(40 kD) |
| Oligosaccharide | 1 mM 5DexS | 1 mM 5DexS |
| End point $t_e$ [min] of measurement | 120 | 120 |
| Storage modulus G' [Pa] at $t_e$ | 2,295 | 2,137 |
| Loss Factor [—] at $t_e$ | 0.00681 | 0.0105 |

5DexS Versus 500DexS

Further, the molecular size of the oligosaccharide was considered as important gelation factor. Previously, gel formation was shown for dextran sulfate of 5 kDa. In this experiment dextran sulfate was applied at 500 kDa and brought into reaction with KA7-RGDSP-starPEG. In addition, the measurements were repeated with KA7-starPEG. The results were compared and plotted side-by-side with the previous obtained data.

Figure 18:
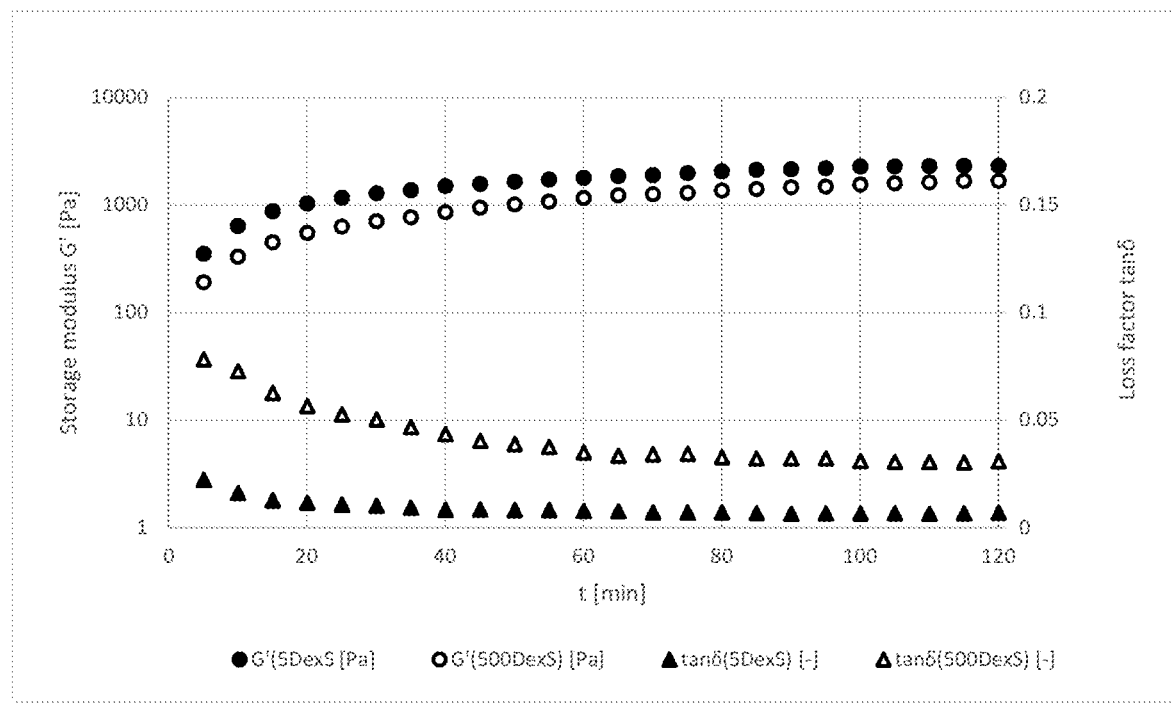
FIG. 18 shows the results of the gelation measurement using dextran sulfate of a molecular size of 5 kDa and 500 kDa with KA7-RGDSP-starPEG.
Figure 19:
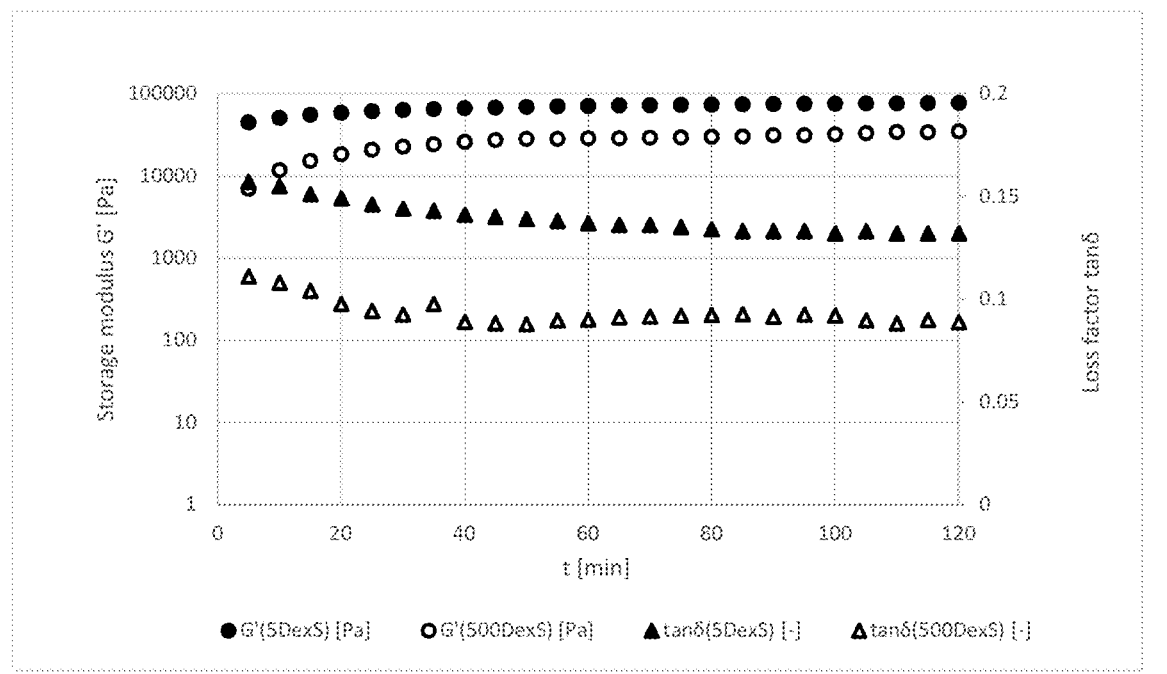
FIG. 19 shows the results of the gelation measurement using dextran sulfate of a molecular size of 5 kDa and 500 kDa with KA7-starPEG.

FIG. 18 and Table 13 present the results of the gelation of KA7-RGDSP-starPEG with 5 kDa and 500 kDa dextran sulfate. At constant mass concentration of dextran sulfate, the G' curves are nearly identical. The loss factor tan δ is slightly more elastic for the 5DexS. The data show that dextran sulfate of both molecular sizes forms stable hydrogels.

TABLE 13

Parameters and results of dextran sulfate of 5 kDa and 500 kDa with KA7-RGDSP-starPEG.

| Parameter | 5DexS | 500DexS |
|---|---|---|
| Peptide-starPEG | 1 mM KA7-RGDSP-starPEG | 1 mM KA7-RGDSP-starPEG |
| Oligosaccharide | 1 mM 5DexS | 0.01 mM 500DexS |
| End point $t_e$ [min] of measurement | 120 | 120 |
| Storage modulus G' [Pa] at $t_e$ | 2,295 | 1,658 |
| Loss Factor [—] at $t_e$ | 0.00681 | 0.0307 |

Figure 20:
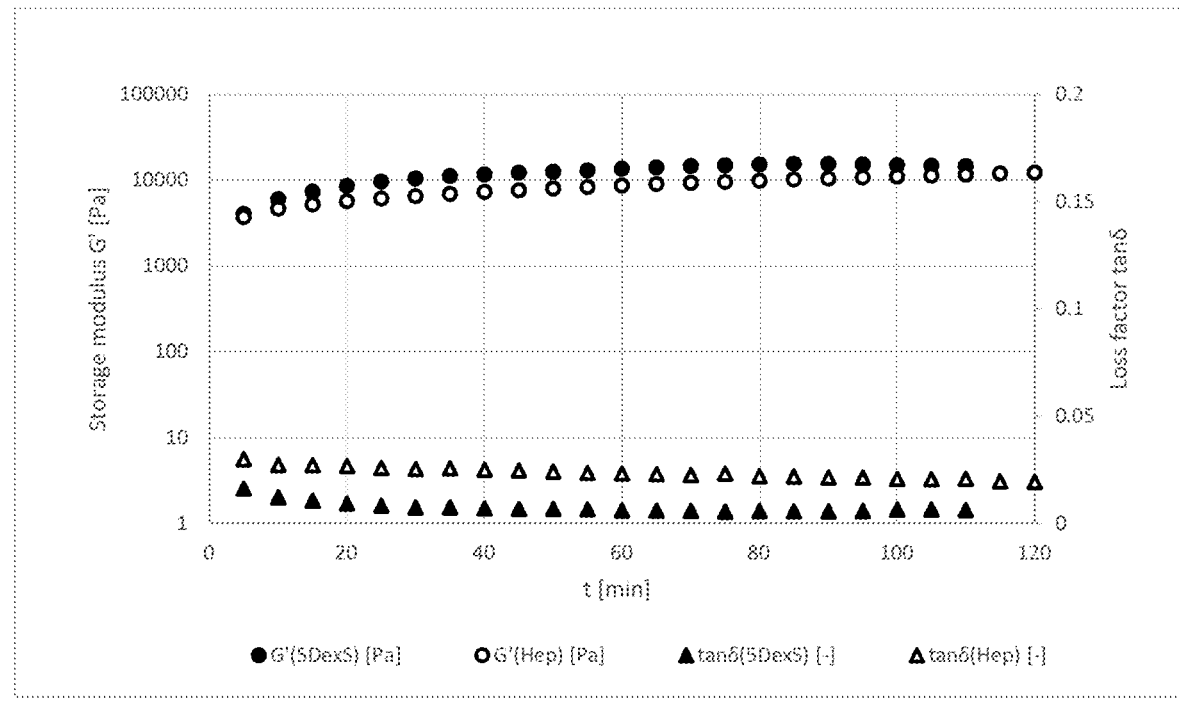
FIG. 20 shows the results of the gelation measurement using dextran sulfate and heparin with KA7-RGDSP-starPEG (10 kDa).

The insertion of the RGDSP peptide sequence to the KA7-starPEG conjugate provides softer gels than KA7-starPEG when brought into reaction with 5DexS. The measurement of 500DexS were repeated with KA7-starPEG. The results are given in FIG. 20 and Table 14. For reason of comparison, the data for 5DexS and KA7-starPEG presented in FIG. 15 are re-presented side-by-side. As reported for the 5DexS, also the 500DexS hydrogel got stiffer when KA7-starPEG was used.

The data indicates that KA7-starPEG can form stable hydrogels with dextran sulfate of different sizes. As shown before, KA7-starPEG forms gels with storage moduli above 10 kPa and loss factors greater than 0.05. 5DexS appeared to result in slightly stiffer yet more viscous hydrogels. Hence, the different sizes of dextran sulfate had a weak impact on the mechanical properties of the formed hydrogels but the gel formation was reliable.

KA7-RGDSP-starPEG components provided in general softer and more elastic gels than KA7-starPEG, which had a stronger impact than molecular size of the selected oligosaccharides.

TABLE 14

Parameters and results of dextran sulfate of 5 kDa versus 500 kDa with KA7-starPEG.

| Parameter | 5DexS | 500DexS |
|---|---|---|
| KA7-starPEG | 2 mM KA7-starPEG | 2 mM KA7-starPEG |
| Oligosaccharide | 2 mM 5DexS | 0.02 mM 500DexS |
| End point $t_e$ [min] of measurement | 120 | 120 |
| Storage modulus G' [Pa] at time point | 76,977 | 34,694 |
| Loss Factor [—] at time point | 0.132 | 0.0887 |

5DexS Versus Hep

Figure 21:
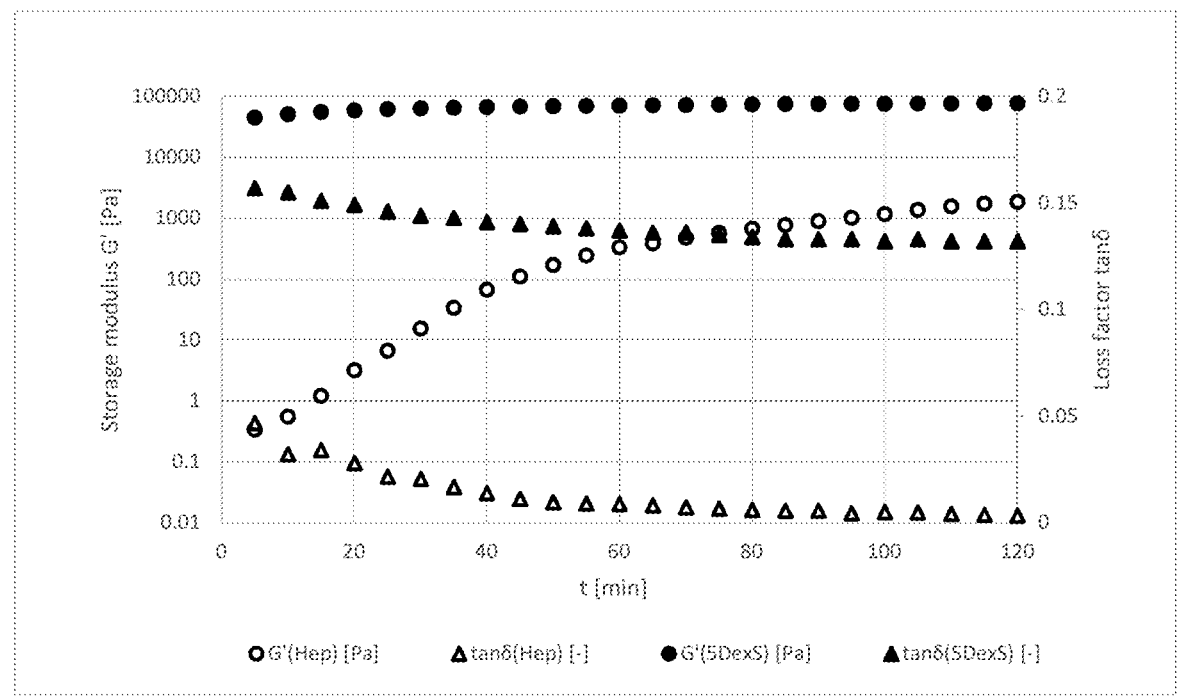
FIG. 21 shows the results of the gelation measurement using dextran sulfate and heparin with KA7-RGDSP-starPEG (10 kDa).
Figure 22:
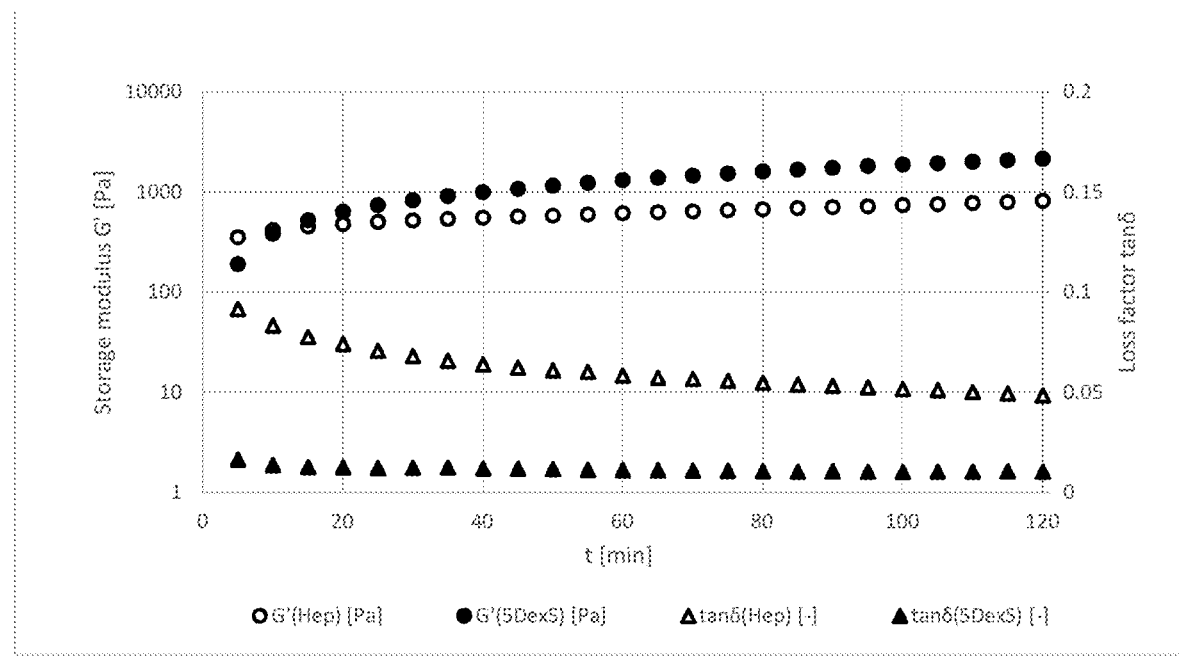
FIG. 22 shows the results of the gelation measurement using dextran sulfate and heparin with KA7-RGDSP-starPEG (40 kDa).

It has been shown that different negatively charged oligosaccharides form a hydrogel with the PEG-KA7 conjugate (Wieduwild et al., 2015, 2013). In this study the gel formation with heparin and dextran sulfate was repeated with KA7-RGDSP-starPEG (FIG. 21 and Table 15) and KA7-starPEG (FIG. 9 and table 12). For a side-by-side comparison with heparin, data for 5DexS from FIG. 2 were re-printed in FIG. 21 and Table 15 (KA7-RGDSP-starPEG) and FIG. 22 and Table 16 (KA7-starPEG).

Both oligosaccharides formed hydrogels with a loss factor tan δ<0.02 indicating highly elastic gel properties. The Hep gel was slightly more elastic than the 5DexS gel. The storage moduli G' developed similar and reached 14.5 kPa and 12.1 kPa after 110 min of gelation.

TABLE 15

Parameters and results of dextran sulfate and heparin reacting with KA7-RGDSP-starPEG(10 kDa).

| Parameter | 5DexS | Hep |
|---|---|---|
| Peptide-starPEG | 2 mM KA7-RGDSP-starPEG | 2 mM KA7-RGDSP-starPEG |
| Oligosaccharide | 2 mM 5DexS | 2 mM Hep |
| End point $t_e$ [min] of measurement | 110 | 120 |
| Storage modulus G' [Pa] at time point | 14,486 | 12,104 |
| Loss Factor [—] at time point | 0.00611 | 0.0193 |

Using KA7-starPEG with additional peptide sequence led to enhanced differences. The gelation with Hep takes longer than with 5DexS as indicated by the steady increase of the G' curve. After 120 min of gelation the storage modulus G' is lower by a factor of 40 for Hep gels than for 5DexS gels. Nonetheless, heparin and dextran sulfate enabled formation of stable hydrogels with starPEG polymers through the KA7 peptide linker.

TABLE 16

Parameters and results of dextran sulfate and heparin reacting with KA7-starPEG(10 kDa).

| Parameter | 5DexS | Hep |
|---|---|---|
| KA7-starPEG | 2 mM KA7-starPEG | 2 mM KA7-starPEG |
| Oligosaccharide | 2 mM 5DexS | 2 mM Hep |
| End point $t_e$ [min] of measurement | 120 | 120 |
| Storage modulus G' [Pa] at time point | 76,977 | 1,849 |
| Loss Factor [—] at time point | 0.132 | 0.0131 |

Finally, hydrogels made of 5DexS and Hep and crosslinked with larger KA7-RGDSP-starPEG (40 kDa) were compared. All components were brought into reaction at equimolar concentration of 1 mM.

Both conditions formed hydrogels. In comparison to FIG. 9, the gels became softer and more viscous as indicated by lower storage moduli G' and loss factor tan δ. The G' of 5DexS gels decreased to 2.140 Pa (see direct comparison of 10 kDa to 40 kDa in FIG. 17). Heparin and 40 kDa KA7-RGDSP-starPEG formed gels of G'=811 Pa, which reassembles soft tissue in the human body. In can be concluded that 5DexS and heparin can be employed for non-covalent hydrogel formation via a PEG-coupled KA7 linker peptide.

TABLE 17

Parameters and results of dextran sulfate and heparin reacting with KA7-RGDSP-starPEG(40 kDa).

| Parameter | 5DexS | Hep |
|---|---|---|
| Peptide-starPEG | 1 mM KA7-RGDSP-starPEG(40kD) | 1 mM KA7-RGDSP-starPEG(40kD) |
| Oligosaccharide | 1 mM 5DexS | 1 mM Hep |
| End point $t_e$ [min] of measurement | 120 | 120 |
| Storage modulus G' [Pa] at time point | 2,137 | 811 |
| Loss Factor [—] at time point | 0.0105 | 0.0486 |

Cyclodextrins

Figure 23:
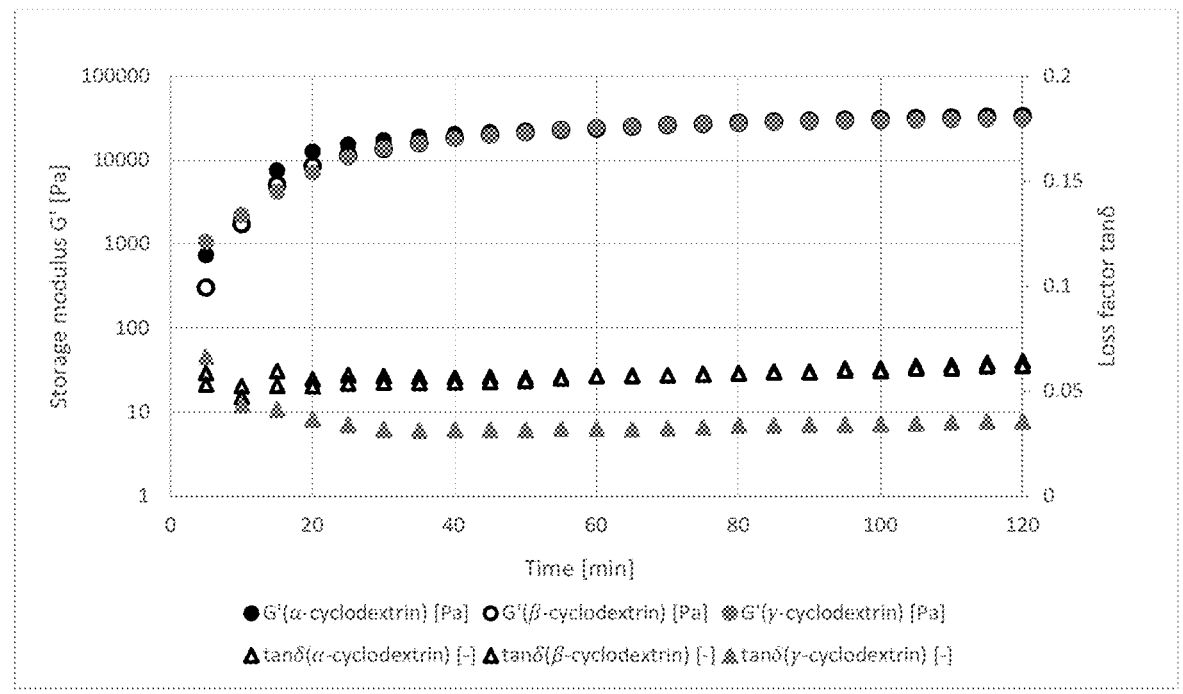
FIG. 23 shows the results of the gelation measurement for α-cyclodextrin sulfate, β-cyclodextrin sulfate and γ-cyclodextrin sulfate brought into reaction with KA7-starPEG.

It has been proposed that sulfated cyclodextrins can different ring size can be used to create non-covalent hydrogels with PEG-(BA)n conjugate. In this study, α-cyclodextrin sulfate, β-cyclodextrin sulfate, γ-cyclodextrin sulfate was employed with KA7-starPEG and compared for hydrogel formation and mechanical properties (FIG. 23 and Table 18).

The gel formation experiments show a uniform gelation within 40 min after mixing the components. All three sulfated cyclodextrins reached a storage modulus of about 30 kPa after 120 min, which are softer gels than with 2 mM 5DexS but stiffer than with 1 mM 5DexS or 2 mM heparin. Low loss factors indicate elastic over viscous properties. In conclusion, these numbers provide evidence that sulfated cyclodextrins are suitable oligosaccharides to form a non-covalent self-organizing hydrogel with starPEG-(BA)n conjugate.

TABLE 18

Parameters and results of α-cyclodextrin sulfate, β-cyclodextrin sulfate and γ-cyclodextrin sulfate reacting with KA7-starPEG.

| Parameter | α-cyclodextrin | β-cyclodextrin | γ-cyclodextrin |
|---|---|---|---|
| KA7-starPEG | 1.5 mM KA7-starPEG(10 kD) | 1.5 mM KA7-starPEG(10 kD) | 1.5 mM KA7-starPEG(10 kD) |
| Oligosaccharide | 3 mM α-cyclodextrin | 3 mM β-cyclodextrin | 3 mM γ-cyclodextrin |
| End point $t_e$ [min] of measurement | 120 | 120 | 120 |
| Storage modulus G' [Pa] at time point | 30,561 | 33,169 | 30,749 |
| Loss Factor [—] at time point | 0.0641 | 0.062 | 0.0355 |

In further preferred embodiments of the invention, the hydrogel matrix further comprises therapeutic agents embedded in the hydrogel gel matrix. Moreover, the hydrogel matrix may be provided in the form of hydrogel beads. These embodiments are exemplified with experimental data below.

Release of Labelled Peptides, IgG Antibody and Tagged Cyclosporin A

In this experimental setting, the binding and release of fluorescein labelled heparin binding peptides from a non-covalent heparin KA7-starPEG hydrogel was analyzed. Ten peptides according to the (BA)n motif scheme and an antithrombin III derived sequence were selected as tags and fluorescently labelled with fluorescein. Peptides and peptide-starPEG were synthesized as described hereinbefore.

The fluorescein labelled peptides tags were mixed with 14 kDa heparin and KA7-starPEG to yield final concentrations of 2 mM (peptide), 2.5 mM (heparin) and 2.5 mM (KA7-starPEG), in 10 μL hydrogel. The formed hydrogel was covered with 200 μL PBS and incubated at room temperature. The release of the peptides was monitored at the indicated time points with fluorescence spectroscopy (FIG. 24A-B).

The (BA)n tags showed a strong initial release but a continuous decrease in peptide release (FIG. 24C-D). Shorter peptides showed a stronger initial release than longer version. Peptides of KAn pattern showed similar profile as the RAn tags. In contrast, the ATIII tag provided a constant release within the measurement period. The results indicate that the sequence of the peptide influences the release pattern, whereas the length of the peptide tag contributes to the binding strength.

In a control experiment, a FITC-labelled IgG antibody (4 mg/ml) was encapsulated into the hydrogel and the release monitored by fluorescent spectroscopy. In contrast to the smaller peptide tags, the 150 kDa protein was completely released within 24 h (FIG. 24E). This indicates a diffusion-dependent equilibration in absence of specific binding to the hydrogel. Hydrogel porosity and diffusion constants were not inhibiting factors. Hence, it can be assumed that the release of the smaller peptides is primarily dependent on the specific heparin-peptide interaction and not limited by the porosity or diffusion.

Next, the release of the drug cyclosporin A has been analyzed. Cyclosporin A is applied as immunosuppressive drug but also an efficient inhibitor of cyclophilin. The ATIII tag has been selected to realize a stable release of cyclosporin A from the hydrogel. After conjugation with an ATIII tag, the immunosuppression was found to be impaired while the inhibition of cyclophilin was preserved. Hence, an cyclophilin enzyme (PPlase) activity assay could be applied to indirectly quantify the cyclosporin A concentration in the supernatant. This assay was applied to monitor the release of ATIII tagged cyclosporin A over the time course of 5 weeks (FIG. 24F). The results demonstrate that the hydrogel provide a stable and constant release of drug conjugates over the measurement period.

In summary, it has been shown that peptides as well as drugs can be released at tag-dependent rates from the non-covalent hydrogel.

Release of Captured IgG Antibodies from Dextran KA7-starPEG Hydrogel Beads

The non-covalent hydrogel can utilized to form micro-carriers (beads). These beads can be applied to deliver compounds and drugs like antibodies.

Monodisperse hydrogel beads were made of dextran sulfate and KA7-starPEG and formed by a microfluidic system (FIG. 25A). Therefore, 4.2 mM peptide-starPEG conjugate and 70 mM 5 kDa dextran sulfate were dissolved separately in PBS. After filtering, the peptide-starPEG conjugate was filled in a 250 μl syringe and the dextran sulfate in a 100 μl syringe. These two syringes have been inserted in an microfluidic mixing tee (FIG. 25B). The mixed solution was further taken up by an oil crossflow with 0.5 ml/min velocity. The adjacent tubing had a length of 10 m to ensure bead separation during the hydrogel formation for a minimum of 10 minutes. The beads were collected in 15 ml tubes and the oil was removed by washing. Images of rhodamine labelled beads are provided in FIG. 25C.

An IgG antibody, fluorescently labeled with FITC, was premixed at 20 mg/ml with the KA7-starPEG solution. After hydrogel formation, beads were washed once and then re-suspended into cell culture media. The antibody concentration in the supernatant was measured every 5 min for an hour with fluorescent spectroscopy. FIG. 25D shows a complete release of the encapsulated antibody within 50 min. This result is in line with the previous release study of IgG antibody from heparin based hydrogel. Hence, it provides evidence, that the hydrogel does not inhibit the diffusion of large proteins. Only after conjugation of a binding tag, molecules are retained within the hydrogel as shown for the cyclosporin A with the ATIII-tag.

Storage and Release of Antibody Mediated by Antibody-specific Epitopes Conjugated to the starPEG The impact of an antibody binding sequence coupled to the starPEG-conjugate of the hydrogel was analyzed.

An epitope sequence binding an anti-VEGF antibody was synthesized with KA7 tag and conjugated to starPEG as previously described. The non-antibody control was prepared by mixing 2 mM KA7-epitope-starPEG with 2 mM of 5 kDa dextran sulfate to form a non-covalent hydrogel. The antibody loaded hydrogel was prepared by dilution of 100 μg/mL antibody with 4 mM dextran sulfate solution followed by addition of 4 mM KA7-epitope-starPEG in a volume ration of 1:1:2 (antibody:KA7-starPEG conjugate: dextran sulfate) to yield 1 mM of starPEG/dextran sulfate hydrogel. KA7-starPEG conjugate without the epitope sequence was used as control.

Figure 26:
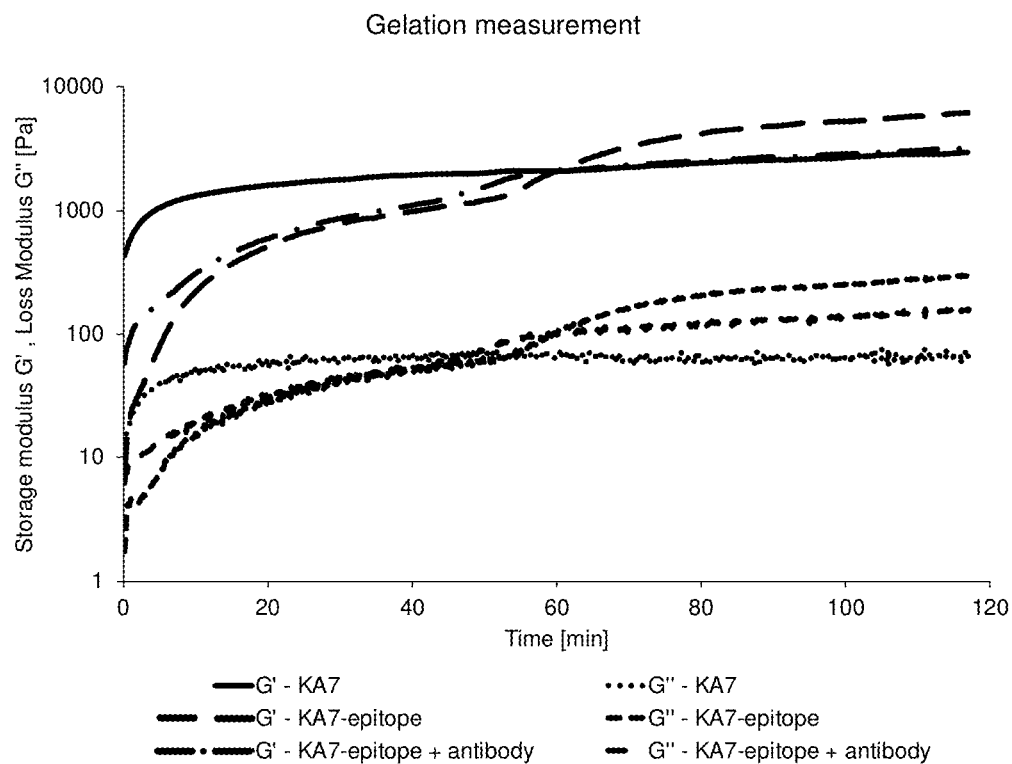
FIG. 26 shows the storage (G') and loss (G") modulus of KA7-hydrogel and KA7-epitpope hydrogel. The hydrogel was formed by mixing 2 mM KA7-starPEG (KA7) or KA7-epitope-starPEG (KA7-epitope) or KA7-epitope-starPEG premixed with the anti-VEGF antibody (KA7-epitope+antibody) with 2 mM 5 kDa Dextran sulfate. All components have been dissolved in PBS, pH 7. The gelation analysis of the formed hydrogels was conducted using a rheometer with a conical plate geometry. The storage and loss modulus was measured every 5 min.

Analysis of the gel formation by time dependent recording of G' and G" showed stable hydrogel formation within 60 min for all conditions. Further, hydrogels made of KA7-starPEG or KA7-epitope and KA7-epitope with or without encapsulated antibody showed similar viscoelastic properties (FIG. 26). These results provided evidence that the gel formation is reliable and not inhibited by introduction of additional binding sequences nor encapsulation of antibody molecules.

For conduction of the release analysis, samples were prepared as follows: 50 μl of the mixed hydrogel solutions were pipetted into a 500 μl reaction tube and incubated overnight. 500 μl of PBS was added and 100 μl of sample was taken at time points $t_i$ to $t_{i+n}$. The concentration of the anti-VEGF antibody was analyzed with ELISA.

Figure 27:
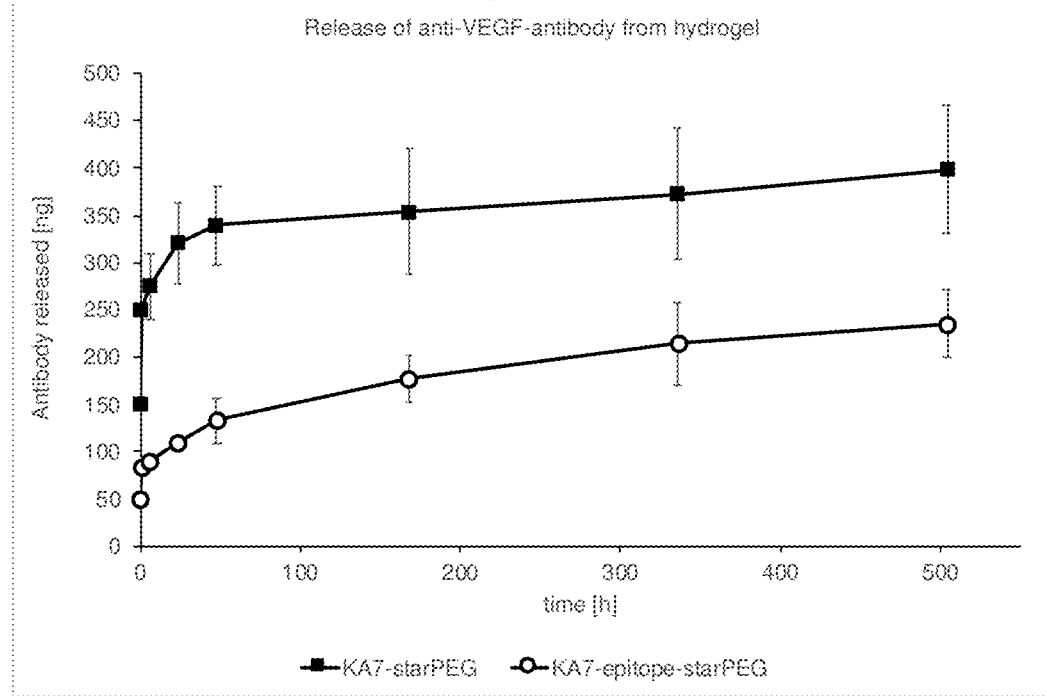
FIG. 27 shows the cumulative release profile of the anti-VEGF antibody from KA7-starPEG hydrogel and KA7-epitope-starPEG hydrogel. The hydrogel was formed with 5 kDa dextran sulfate.

The cumulative values are provided in FIG. 27. The data show a burst release of the antibody from the control hydrogel without the epitope sequence. However, hydrogel containing the epitope better retains the antibody. The release development after the initial 48 hours is similar in both groups and not reaching full release within 21 days of sampling. It can be concluded, that the insertion of the antibody binding sequence provided a functional and effective to retained and release an antibody from the no-covalent hydrogel in a controlled fashion.

In summary, the hydrogel matrix according to the invention enables biological functions, as well as non-toxicity for human cells, protein binding and release, adjustable enzymatic degradability together with flexible physical properties, such as adjustability of the gelation time and flow behavior by variation of the oligosaccharides and peptides (peptide-starPEG-conjugates) and their concentration and broad chemical modifiability purely by non-covalent interaction of the hydrogel matrix components without any chemical reaction during the gel formation.

In particular heparin is a highly sulfated oligosaccharide, which binds growth factors, which are for example used in cell culture. Non-covalent hydrogels that are based on heparin and paring binding peptides were developed, however they are not adjustable. De novo produced heparin-binding peptides whose properties can be changed by adjusting their length, solve this problem. All properly functioning peptides that have been produced de novo so far are longer than 20 amino acids. This would lead to synthesis problems when additional properties are to be introduced. Here, the variety of the properties of the newly configured (BA)n-peptide-motif was demonstrated by using a designed peptide-starPEG-library for non-covalent hydrogel formation. Not only do these peptides undergo structural changes after binding to heparin as reported for peptide of natural origin, but they also represent the shortest artificial heparin binding peptides that are known from the literature. The adjustability of the non, covalent hydrogel with (BA)n-starPEG-conjugates and heparin is surprising. It is possible to adjust the stiffness, the gelation time and the biological and chemical stability solely by changing the length, the concentration or the type of basic amino acid of the (BA)n peptide-motif. In this way, it is possible to change the properties while retaining the solids content or to change the solids content while keeping the properties stable.

Cell culture of adhesive cells requires the incorporation of bioactive peptide sequences. The data show that insertion of a model sequences (RGDSP) to the KA7 linker does not interfere with the hydrogel formation. However, the hydrogels were becoming softer as indicated by lower storage moduli.

The PEG polymer can be applied at different shapes. Both, linear and 4-arm (star)PEG form stable hydrogels. The linearPEG makes softer gels, which can be explained by the lower crosslinking potency of a linear versus a 4-arm molecule.

Further, the starPEG can be employed at molecular sizes of 10 and 40 kDa. Both sizes enable non-covalent cross-linking with larger starPEG is leading to more viscous gels and softer gels.

The size of the oligosaccharide can be varied as well. In this report, dextran sulfate have been applied at 5 kDa and 500 kDa. Both sizes of dextran sulfate forms stable hydrogels. Larger molecular sizes provide softer and more viscous gels.

Negatively charged oligosaccharide of different structure enable non-covalent hydrogel formation. It was shown that heparin and dextran sulfate reliably form hydrogels with KA7-RGDSP-starPEG and KA7-starPEG. Heparin tends to form softer gels. In addition, cyclodextrin sulfates of different ring sizes (alpha, beta and gamma) were applied too. All cyclodextrin sulfates formed stable hydrogel, with higher stiffness than dextran sulfate or heparin. It can be concluded, that negatively charged oligosaccharides are generally suitable components for hydrogel formation.

In summary, the non-covalent hydrogel formation is taking place with PEG polymers of different shape (linear and 4-arm star-shaped) and size (10 and 40 kDa) and negatively charged oligo-saccharides (heparin, dextran sulfate, α-cyclodextrin sulfate, β-cyclodextrin sulfate, γ-cyclodextrin sulfate) of different molecular size. Insertion of additional peptide sequences to the linker was also guaranteeing stable hydrogel formation (KA7 compared to KA7-RGDSP or KA7 compared to KA7-epitope). All variation have impact on the mechanical properties of the resulting hydrogel, which provides a large parameter spacer of optimization and tailored solutions for biotechnological applications.

We claim:

1. A hydrogel matrix comprising a mixture of covalent peptide-polymer conjugates and an oligosaccharide;
    wherein said oligosaccharide is a highly negatively-charged, sulfated oligosaccharide selected from the group consisting of heparin, dextran sulfate, α-cyclodextrin sulfate, β-cyclodextrin sulfate and γ-cyclodextrin sulfate;
    wherein said polymer comprised in said peptide-polymer conjugates is a linear or star polyethylene glycol;
    wherein said peptide comprised in said peptide-polymer conjugates consists of an amino acid sequence of SEQ ID NO.5; and
    wherein said hydrogel matrix is configured in the form of an oligosaccharide/peptide/polymer system, in which said peptide is chemically conjugated to the polymer such that the hydrogel is obtained by mixing the peptide-polymer conjugate and the oligosaccharide, and
    wherein the linear or star polyethylene glycol is 10 kDa or 40 kDa.

2. The hydrogel matrix according to claim 1, wherein the polymer chain is a star polyethylene glycol.

3. The hydrogel matrix according to claim 1, wherein the said oligosaccharide is dextran sulfate having a molecular weight of 4 kDa to 600 kDa.

4. The hydrogel matrix according to claim 1, wherein the degree of sulfation in the α-cyclodextrin sulfate, β-cyclodextrin sulfate or γ-cyclodextrin ranges from three sulfates per molecule to a complete sulfation.

5. The hydrogel matrix of claim 1, further comprising a pH-sensitive chemical linker between the polymer chain and the peptide sequence.

6. The hydrogel matrix according to claim 1, having an elasticity modulus of at least 10 Pa.

7. The hydrogel matrix according to claim 1, further comprising cells embedded in the hydrogel matrix.

8. The hydrogel matrix according to claim 7, wherein said cells are selected from the group consisting of mammalian cells, insect cells, bacterial cells, and yeast cells.

9. The hydrogel matrix according to claim 8, wherein the mammalian cells are selected from the group consisting of cancer cell lines, fibroblast cells, embryonic stem cells, pluripotent stem cells, induced pluripotent stem cells, mesenchymal stroma cells, human T.cells, and human B.cells.

10. The hydrogel matrix of claim 1, wherein said hydrogel matrix is in the form of hydrogel beads.

\* \* \* \* \*

SEQUENCE LISTING

```
<160> NUMBER OF SEQ ID NOS: 27

<210> SEQ ID NO 1
<211> LENGTH: 18
<212> TYPE: PRT
<213> ORGANISM: Human

<400> SEQUENCE: 1

Cys Trp Gly Gly Lys Ala Phe Ala Lys Leu Ala Ala Arg Leu Tyr Arg
1               5                   10                  15

Lys Ala

<210> SEQ ID NO 2
<211> LENGTH: 6
<212> TYPE: PRT
<213> ORGANISM: Artificial sequence
<220> FEATURE:
<223> OTHER INFORMATION: Synthetic peptide

<400> SEQUENCE: 2

Cys Trp Gly Gly Lys Ala
1               5

<210> SEQ ID NO 3
<211> LENGTH: 10
<212> TYPE: PRT
<213> ORGANISM: Artificial sequence
<220> FEATURE:
<223> OTHER INFORMATION: Synthetic peptide

<400> SEQUENCE: 3
```

```
Cys Trp Gly Gly Lys Ala Lys Ala Lys Ala
1               5                   10
```

<210> SEQ ID NO 4
<211> LENGTH: 14
<212> TYPE: PRT
<213> ORGANISM: Artificial sequence
<220> FEATURE:
<223> OTHER INFORMATION: Synthetic peptide

<400> SEQUENCE: 4

```
Cys Trp Gly Gly Lys Ala Lys Ala Lys Ala Lys Ala Lys Ala
1               5                   10
```

<210> SEQ ID NO 5
<211> LENGTH: 16
<212> TYPE: PRT
<213> ORGANISM: Artificial sequence
<220> FEATURE:
<223> OTHER INFORMATION: Synthetic peptide

<400> SEQUENCE: 5

```
Cys Trp Gly Gly Lys Ala Lys Ala Lys Ala Lys Ala Lys Ala Lys Ala
1               5                   10                  15
```

<210> SEQ ID NO 6
<211> LENGTH: 18
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(2)
<223> OTHER INFORMATION: D-amino acid
<220> FEATURE:
<221> NAME/KEY: MISC_FEATURE
<222> LOCATION: (5)..(18)
<223> OTHER INFORMATION: D-amino acid

<400> SEQUENCE: 6

```
Cys Trp Gly Gly Lys Ala Lys Ala Lys Ala Lys Ala Lys Ala Lys Ala
1               5                   10                  15

Lys Ala
```

<210> SEQ ID NO 7
<211> LENGTH: 18
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (7)..(7)
<223> OTHER INFORMATION: D-amino acid
<220> FEATURE:
<221> NAME/KEY: MISC_FEATURE
<222> LOCATION: (9)..(9)
<223> OTHER INFORMATION: D-amino acid
<220> FEATURE:
<221> NAME/KEY: MISC_FEATURE
<222> LOCATION: (11)..(11)
<223> OTHER INFORMATION: D-amino acid
<220> FEATURE:
<221> NAME/KEY: MISC_FEATURE
<222> LOCATION: (13)..(13)
<223> OTHER INFORMATION: D-amino acid

```
<220> FEATURE:
<221> NAME/KEY: MISC_FEATURE
<222> LOCATION: (15)..(15)
<223> OTHER INFORMATION: D-amino acid
<220> FEATURE:
<221> NAME/KEY: MISC_FEATURE
<222> LOCATION: (17)..(17)
<223> OTHER INFORMATION: D-amino acid

<400> SEQUENCE: 7

Cys Trp Gly Gly Lys Ala Lys Ala Lys Ala Lys Ala Lys Ala Lys Ala
1               5                   10                  15

Lys Ala

<210> SEQ ID NO 8
<211> LENGTH: 18
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (10)..(10)
<223> OTHER INFORMATION: D-amino acid
<220> FEATURE:
<221> NAME/KEY: MISC_FEATURE
<222> LOCATION: (12)..(12)
<223> OTHER INFORMATION: D-amino acid
<220> FEATURE:
<221> NAME/KEY: MISC_FEATURE
<222> LOCATION: (14)..(14)
<223> OTHER INFORMATION: D-amino acid
<220> FEATURE:
<221> NAME/KEY: MISC_FEATURE
<222> LOCATION: (16)..(16)
<223> OTHER INFORMATION: D-amino acid
<220> FEATURE:
<221> NAME/KEY: MISC_FEATURE
<222> LOCATION: (18)..(18)
<223> OTHER INFORMATION: D-amino acid

<400> SEQUENCE: 8

Cys Trp Gly Gly Lys Ala Lys Ala Lys Ala Lys Ala Lys Ala Lys Ala
1               5                   10                  15

Lys Ala

<210> SEQ ID NO 9
<211> LENGTH: 18
<212> TYPE: PRT
<213> ORGANISM: Artificial sequence
<220> FEATURE:
<223> OTHER INFORMATION: Synthetic peptide

<400> SEQUENCE: 9

Cys Trp Gly Gly Lys Ala Lys Ala Lys Ala Lys Ala Lys Ala Lys Ala
1               5                   10                  15

Lys Ala

<210> SEQ ID NO 10
<211> LENGTH: 19
<212> TYPE: PRT
<213> ORGANISM: Artificial sequence
```

<220> FEATURE:
<223> OTHER INFORMATION: Synthetic peptide

<400> SEQUENCE: 10

Cys Trp Gly Gly Lys Lys Ala Lys Lys Ala Lys Lys Ala Lys Lys Ala
1               5                   10                  15

Lys Lys Ala

<210> SEQ ID NO 11
<211> LENGTH: 6
<212> TYPE: PRT
<213> ORGANISM: Artificial sequence
<220> FEATURE:
<223> OTHER INFORMATION: Synthetic peptide

<400> SEQUENCE: 11

Cys Trp Gly Gly Lys Gly
1               5

<210> SEQ ID NO 12
<211> LENGTH: 10
<212> TYPE: PRT
<213> ORGANISM: Artificial sequence
<220> FEATURE:
<223> OTHER INFORMATION: Synthetic peptide

<400> SEQUENCE: 12

Cys Trp Gly Gly Lys Gly Lys Gly Lys Gly
1               5                   10

<210> SEQ ID NO 13
<211> LENGTH: 14
<212> TYPE: PRT
<213> ORGANISM: Artificial sequence
<220> FEATURE:
<223> OTHER INFORMATION: Synthteic peptide

<400> SEQUENCE: 13

Cys Trp Gly Gly Lys Gly Lys Gly Lys Gly Lys Gly Lys Gly
1               5                   10

<210> SEQ ID NO 14
<211> LENGTH: 18
<212> TYPE: PRT
<213> ORGANISM: Artificial sequence
<220> FEATURE:
<223> OTHER INFORMATION: Synthetic peptide

<400> SEQUENCE: 14

Cys Trp Gly Gly Lys Gly Lys Gly Lys Gly Lys Gly Lys Gly Lys Gly
1               5                   10                  15

Lys Gly

<210> SEQ ID NO 15
<211> LENGTH: 18
<212> TYPE: PRT
<213> ORGANISM: Artificial sequence
<220> FEATURE:
<223> OTHER INFORMATION: Synthetic peptide

<400> SEQUENCE: 15

Cys Trp Gly Lys Lys Gly Lys Lys Gly Lys Lys Gly Lys Lys Gly Lys
1               5                   10                  15

Lys Gly

<210> SEQ ID NO 16
<211> LENGTH: 6
<212> TYPE: PRT
<213> ORGANISM: Artificial sequence
<220> FEATURE:
<223> OTHER INFORMATION: Synthetic peptide

<400> SEQUENCE: 16

Cys Trp Gly Gly Arg Ala
1               5

<210> SEQ ID NO 17
<211> LENGTH: 10
<212> TYPE: PRT
<213> ORGANISM: Artificial sequence
<220> FEATURE:
<223> OTHER INFORMATION: Synthetic peptide

<400> SEQUENCE: 17

Cys Trp Gly Gly Arg Ala Arg Ala Arg Ala
1               5                   10

<210> SEQ ID NO 18
<211> LENGTH: 14
<212> TYPE: PRT
<213> ORGANISM: Artificial sequence
<220> FEATURE:
<223> OTHER INFORMATION: Synthetic peptide

<400> SEQUENCE: 18

Cys Trp Gly Gly Arg Ala Arg Ala Arg Ala Arg Ala Arg Ala
1               5                   10

<210> SEQ ID NO 19
<211> LENGTH: 18
<212> TYPE: PRT
<213> ORGANISM: Artificial sequence
<220> FEATURE:
<223> OTHER INFORMATION: Synthetic peptide

<400> SEQUENCE: 19

Cys Trp Gly Gly Arg Ala Arg Ala Arg Ala Arg Ala Arg Ala Arg Ala
1               5                   10                  15

Arg Ala

<210> SEQ ID NO 20
<211> LENGTH: 18
<212> TYPE: PRT
<213> ORGANISM: Artificial sequence
<220> FEATURE:
<223> OTHER INFORMATION: Synthetic peptide

<400> SEQUENCE: 20

Cys Trp Gly Gly Arg Ala Arg Arg Ala Arg Arg Ala Arg Arg Ala Arg
1               5                   10                  15

Arg Ala

<210> SEQ ID NO 21
<211> LENGTH: 6
<212> TYPE: PRT
<213> ORGANISM: Artificial sequence
<220> FEATURE:
<223> OTHER INFORMATION: Synthetic peptide

<400> SEQUENCE: 21

Cys Trp Gly Gly Arg Gly
1               5

<210> SEQ ID NO 22
<211> LENGTH: 10
<212> TYPE: PRT
<213> ORGANISM: Artificial sequence
<220> FEATURE:
<223> OTHER INFORMATION: Synthetic peptide

<400> SEQUENCE: 22

Cys Trp Gly Gly Arg Gly Arg Gly Arg Gly
1               5                   10

<210> SEQ ID NO 23
<211> LENGTH: 14
<212> TYPE: PRT
<213> ORGANISM: Artificial sequece
<220> FEATURE:
<223> OTHER INFORMATION: Synthetic peptide

<400> SEQUENCE: 23

Cys Trp Gly Gly Arg Gly Arg Gly Arg Gly Arg Gly Arg Gly
1               5                   10

<210> SEQ ID NO 24
<211> LENGTH: 18
<212> TYPE: PRT
<213> ORGANISM: Artificial sequence
<220> FEATURE:
<223> OTHER INFORMATION: Synthetic peptide

<400> SEQUENCE: 24

Cys Trp Gly Gly Arg Gly Arg Gly Arg Gly Arg Gly Arg Gly Arg Gly
1               5                   10                  15

Arg Gly

<210> SEQ ID NO 25
<211> LENGTH: 18
<212> TYPE: PRT
<213> ORGANISM: Artificial sequence
<220> FEATURE:
<223> OTHER INFORMATION: Synthetic peptide

<400> SEQUENCE: 25

Cys Trp Gly Arg Arg Gly Arg Arg Gly Arg Arg Gly Arg Arg Gly Arg
1               5                   10                  15

Arg Gly

<210> SEQ ID NO 26
<211> LENGTH: 25
<212> TYPE: PRT
<213> ORGANISM: Artificial sequence
<220> FEATURE:
<223> OTHER INFORMATION: Synthetic peptide

<400> SEQUENCE: 26

Cys Trp Gly Gly Arg Gly Asp Ser Pro Gly Gly Lys Ala Lys Ala Lys
1               5                   10                  15

Ala Lys Ala Lys Ala Lys Ala Lys Ala
            20                  25

<210> SEQ ID NO 27
<211> LENGTH: 5
<212> TYPE: PRT

```
<213> ORGANISM: Human

<400> SEQUENCE: 27

Arg Gly Asp Ser Pro
1               5
```